(12) United States Patent
Zhi et al.

(10) Patent No.: US 12,208,071 B2
(45) Date of Patent: Jan. 28, 2025

(54) GLUCAGON RECEPTOR ANTAGONISTS

(71) Applicant: LIGAND PHARMACEUTICALS INCORPORATED, San Diego, CA (US)

(72) Inventors: Lin Zhi, Austin, TX (US); Ian Henderson, Plainsboro, NJ (US); Joseph Kaloko, Durham, NC (US); Martin Osterhout, Raleigh, NC (US)

(73) Assignee: Ligand Pharmaceuticals Incorporated, San Diego, CA (US)

( * ) Notice: Subject to any disclaimer, the term of this patent is extended or adjusted under 35 U.S.C. 154(b) by 1004 days.

(21) Appl. No.: 16/969,521

(22) PCT Filed: Feb. 13, 2019

(86) PCT No.: PCT/US2019/017833
§ 371 (c)(1),
(2) Date: Aug. 12, 2020

(87) PCT Pub. No.: WO2019/160940
PCT Pub. Date: Aug. 22, 2019

(65) Prior Publication Data
US 2021/0121422 A1    Apr. 29, 2021

Related U.S. Application Data

(60) Provisional application No. 62/635,461, filed on Feb. 26, 2018, provisional application No. 62/630,190, filed on Feb. 13, 2018.

(51) Int. Cl.
| | | |
|---|---|---|
| A61K 31/185 | (2006.01) | |
| A61K 31/155 | (2006.01) | |
| A61K 31/366 | (2006.01) | |
| A61K 31/427 | (2006.01) | |
| A61K 31/4439 | (2006.01) | |
| A61K 31/455 | (2006.01) | |
| A61K 31/64 | (2006.01) | |
| A61K 31/702 | (2006.01) | |
| A61K 31/7032 | (2006.01) | |
| A61K 38/28 | (2006.01) | |
| A61K 38/31 | (2006.01) | |
| A61K 45/06 | (2006.01) | |
| C07C 67/00 | (2006.01) | |
| C07C 67/343 | (2006.01) | |
| C07C 201/12 | (2006.01) | |
| C07C 209/36 | (2006.01) | |
| C07C 231/02 | (2006.01) | |
| C07C 231/12 | (2006.01) | |
| C07C 309/24 | (2006.01) | |
| C07C 315/04 | (2006.01) | |
| C07C 315/06 | (2006.01) | |

(52) U.S. Cl.
CPC .......... *A61K 31/185* (2013.01); *A61K 31/155* (2013.01); *A61K 31/366* (2013.01); *A61K 31/427* (2013.01); *A61K 31/4439* (2013.01); *A61K 31/455* (2013.01); *A61K 31/64* (2013.01); *A61K 31/702* (2013.01); *A61K 31/7032* (2013.01); *A61K 38/28* (2013.01); *A61K 38/31* (2013.01); *A61K 45/06* (2013.01); *C07C 67/00* (2013.01); *C07C 67/343* (2013.01); *C07C 201/12* (2013.01); *C07C 209/36* (2013.01); *C07C 231/02* (2013.01); *C07C 231/12* (2013.01); *C07C 309/24* (2013.01); *C07C 315/04* (2013.01); *C07C 315/06* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 3,524,846 | A | 8/1970 | Moffatt et al. |
| 3,536,809 | A | 10/1970 | Applezweig |
| 3,598,123 | A | 8/1971 | Zaffaroni |
| 3,845,770 | A | 11/1974 | Theeuwes et al. |

(Continued)

FOREIGN PATENT DOCUMENTS

| | | |
|---|---|---|
| EP | 0 284 240 B2 | 6/1993 |
| EP | 0 632 048 A1 | 1/1995 |

(Continued)

OTHER PUBLICATIONS

Caira et al. (Crystalline Polymorphism of Organic Compounds. In: Weber, E., et al. Design of Organic Solids. Topics in Current Chemistry, vol. 198. Springer, Berlin, Heidelberg. https://doi.org/10.1007/3-540-69178-2_5, 1998) (Year: 1998).*
Nidirect (downloaded from URL:<https://www.nidirect.gov.uk/news/preventing-diabetes-and-recognising-its-symptoms#toc-1>) ( Year: 2024).*
Cleveland Clinic (downloaded from URL:<Neurodegenerative Diseases: What They Are & Types (clevelandclinic.org)>) (Year: 2024 ).*
Shirahata et al. (Transplant Int., 16, pp. 2760-279, (2003) (Year: 2003).*
Farmer et al. (Cur. Atheroscler. Rep., 4, pp. 92-98, (2002)) (Year: 2002).*

(Continued)

*Primary Examiner* — Sergio Coffa
(74) *Attorney, Agent, or Firm* — Knobbe, Martens, Olson & Bear LLP

(57) ABSTRACT

Provided herein are solid state forms of compounds, including enantiomerically pure forms thereof, and pharmaceutically acceptable salts or co-crystals and prodrugs thereof which have glucagon receptor antagonist or inverse agonist activity. Further, provided herein are pharmaceutical compositions and methods of treating, preventing, ameliorating, delaying the time to onset or reducing the risk for the development or progression of at least one condition, disease, or disorder for which one or more glucagon receptor antagonist is indicated, including Type I and II diabetes, insulin resistance, hyperglycemia, ketoacidosis, or ketosis.

20 Claims, 38 Drawing Sheets

(56) References Cited

U.S. PATENT DOCUMENTS

| | | | |
|---|---|---|---|
| 3,916,899 | A | 11/1975 | Theeuwes et al. |
| 4,008,719 | A | 2/1977 | Theeuwes et al. |
| 5,059,595 | A | 10/1991 | Le Grazie |
| 5,073,543 | A | 12/1991 | Marshall et al. |
| 5,120,548 | A | 6/1992 | McClelland et al. |
| 5,157,027 | A | 10/1992 | Biller et al. |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,733,566 | A | 3/1998 | Lewis |
| 6,132,420 | A | 10/2000 | Dionne et al. |
| 6,245,357 | B1 | 6/2001 | Edgren et al. |
| 6,270,787 | B1 | 8/2001 | Ayer |
| 6,283,953 | B1 | 9/2001 | Ayer et al. |
| 6,287,295 | B1 | 9/2001 | Chen et al. |
| 6,333,050 | B2 | 12/2001 | Wong et al. |
| 6,342,249 | B1 | 1/2002 | Wong et al. |
| 6,365,185 | B1 | 4/2002 | Ritschel et al. |
| 6,368,626 | B1 | 4/2002 | Bhatt et al. |
| 6,375,975 | B1 | 4/2002 | Modi |
| 6,375,978 | B1 | 4/2002 | Kleiner et al. |
| 6,503,949 | B1 | 1/2003 | Lau et al. |
| 6,875,760 | B2 | 4/2005 | Lau et al. |
| 6,881,746 | B2 | 4/2005 | Lau et al. |
| 7,301,036 | B2 | 11/2007 | Parmee et al. |
| 8,519,145 | B2 | 8/2013 | Kang et al. |
| 8,710,236 | B2 | 4/2014 | Gomez-Galeno et al. |
| 8,907,103 | B2 | 12/2014 | Gomez-Galeno et al. |
| 9,169,201 | B2 | 10/2015 | Gomez-Galeno et al. |
| 9,701,626 | B2 | 7/2017 | Gomez-Galeno et al. |
| 9,783,494 | B2 | 10/2017 | Gomez-Galeno et al. |
| 10,076,504 | B2 | 9/2018 | Zhi |
| 10,221,130 | B2 | 3/2019 | Gomez-Galeno et al. |
| 10,239,829 | B2 | 3/2019 | Gomez-Galeno et al. |
| 2003/0212119 | A1 | 11/2003 | Lau et al. |
| 2003/0236292 | A1 | 12/2003 | Kodra et al. |
| 2004/0014789 | A1 | 1/2004 | Lau et al. |
| 2004/0152750 | A1 | 8/2004 | Kodra et al. |
| 2005/0153890 | A1 | 1/2005 | Pan et al. |
| 2005/0288329 | A1 | 12/2005 | Yao et al. |
| 2006/0003935 | A1 | 1/2006 | Pan et al. |
| 2006/0084681 | A1 | 4/2006 | Parmee et al. |
| 2006/0116366 | A1 | 6/2006 | Parmee et al. |
| 2007/0015757 | A1 | 1/2007 | Madsen et al. |
| 2007/0054902 | A1 | 3/2007 | Fukui et al. |
| 2007/0087987 | A1 | 4/2007 | Monia et al. |
| 2007/0088071 | A1 | 4/2007 | Kim et al. |
| 2007/0105930 | A1 | 5/2007 | Parmee et al. |
| 2007/0203186 | A1 | 8/2007 | Beeson et al. |
| 2007/0249688 | A1 | 10/2007 | Conner et al. |
| 2008/0085926 | A1 | 4/2008 | Stelmach et al. |
| 2008/0108620 | A1 | 5/2008 | Brockunier et al. |
| 2008/0125468 | A1 | 5/2008 | Chappell et al. |

FOREIGN PATENT DOCUMENTS

| | | |
|---|---|---|
| JP | 63-32538 | 2/1988 |
| JP | 09-241284 A | 9/1997 |
| JP | 11-97740 A | 4/1999 |
| WO | WO 90/08155 A1 | 7/1990 |
| WO | WO 90/10636 A1 | 9/1990 |
| WO | WO 91/19721 A1 | 12/1991 |
| WO | WO 00/069810 A1 | 11/2000 |
| WO | WO 00/071510 A2 | 11/2000 |
| WO | WO 01/019830 A1 | 3/2001 |
| WO | WO 01/062717 A1 | 8/2001 |
| WO | WO 02/00612 A1 | 1/2002 |
| WO | WO 02/040444 A1 | 5/2002 |
| WO | WO 03/048109 A1 | 6/2003 |
| WO | WO 03/053938 A1 | 7/2003 |
| WO | WO 04/002480 A1 | 1/2004 |
| WO | WO 04/050039 A2 | 6/2004 |
| WO | WO 04/052869 A1 | 6/2004 |
| WO | WO 04/069158 A2 | 8/2004 |
| WO | WO 04/092156 A1 | 10/2004 |
| WO | WO 04/100875 A2 | 11/2004 |
| WO | WO 05/051298 A1 | 6/2005 |
| WO | WO 05/054213 A1 | 6/2005 |
| WO | WO 05/065680 A1 | 7/2005 |
| WO | WO 05/118542 A1 | 12/2005 |
| WO | WO 05/121097 A2 | 12/2005 |
| WO | WO 05/123668 A1 | 12/2005 |
| WO | WO 06/086488 A2 | 8/2006 |
| WO | WO 06/102067 A1 | 9/2006 |
| WO | WO 06/104826 A2 | 10/2006 |
| WO | WO 07/015999 A2 | 2/2007 |
| WO | WO 07/047177 A1 | 4/2007 |
| WO | WO 07/106181 A2 | 9/2007 |
| WO | WO 07/111864 A2 | 10/2007 |
| WO | WO 07/114855 A2 | 10/2007 |
| WO | WO 07/120270 A2 | 10/2007 |
| WO | WO 07/120284 A2 | 10/2007 |
| WO | WO 07/123581 A1 | 11/2007 |
| WO | WO 07/136577 A2 | 11/2007 |
| WO | WO 08/001883 A1 | 1/2008 |
| WO | WO 08/042223 A1 | 4/2008 |
| WO | WO 08/066356 A1 | 6/2008 |
| WO | WO 08/098244 A1 | 8/2008 |
| WO | WO 10/019830 A1 | 2/2010 |
| WO | WO 13/012959 A1 | 1/2013 |
| WO | WO 15/191900 A1 | 12/2015 |
| WO | WO-2015191900 A1 * | 12/2015 ........... A61K 31/167 |
| WO | WO 2017/008681 | 1/2017 |
| WO | WO 19/160940 | 8/2020 |

OTHER PUBLICATIONS

U.S. Appl. No. 12/526,458, filed Aug. 7, 2009, Gomez-Galeno et al.
Alexander, P., et al., "Preparation of 9-(2-Phosphonomethoxyethyl) Adenine Esters as Potential Prodrugs," Col/ect. Czech. Chem. Commun. (in prior U.S. Appln. No. 12/526,45859), 1853-1869, Nakladatelstvi Ceskoslovenski Akademie Ved. (1994).
Alza Corporation, "L-Oros™ Technology—Advancing New Therapies Through ALZA's Liquid Drug Formation," Delivery Times, vol. II, Issue II, 2002, 12 pages.
American Heart Association, "Metabolic Syndrome" <http://www.americanheart.org/presenter.jhtml?identifier=4756>, Accessed Mar. 31, 2009.
Ash and Ash, Eds., Handbook of Pharmaceutical Additives, 3rd ed, Gower Publishing Company, 2007, 3 pages.
Baddiley et al., "Structure of Coenzyme A," Nature 171:76 (1953).
Benzaria et al., "Synthesis, in Vitro Antiviral Evaluation, and Stability Studies of Bis(S-acyl-2-thioethyl) Ester Derivatives of 9-[2-(Phosphonomethoxy)ethyl] adenine (PMEA) as Potential PMEA Prodrugs with Improved Oral Bioavailability," J. Med. Chem. 39(25):4958-4965 (1996).
Bhongle et al., "Expedient and High-Yield Synthesis of Alkylphosphonyl Cichlorides Under Mile, Neutral Conditions: Reaction of BIS (Trimethylsilyl) Slkyl Phosphonates with Oxalyl Chloridel Dimethylformarnide," Synth. Commu. 17:1071-1706 (1987).
Blackburn et al., "Specific Dealkylation of Phosphonate Esters using Iodotrimethylsilanc," J. Chem. Soc., Chem. Commun. 870-871 (1978).
Brand et al., "Evidence for a Major Role of Glucagon in the Hyperglycemia of Experimental Diabetes," A Journal of the American Diabetes Association, 1994, 43 (Suppl. 1), 172A.
Brand et al., "Immunoneutralization of endogenous glucagon with monoclonal glucagon antibody normalizes hyperglycemia in moderately streptozotocin-diabetic rats," Diabetologia 1994, vol. 37, pp. 985-993.
Brechbühler et al., "Die Reaktion von Carbonsauren mit Acetalen des N, N-Dimethylformmids: eine Veresterungsmethode," Helv. Chim. Acta. 48(7):1746-1771 (1965).
Bundgaaard, ed., Design of Prodrugs, Elsevier Science, Amsterdam, 1985.
Busch-Peterson et al., "Lithium N-trityl-N-(R)-I-phenethylamide, a readily available and useful base for the enantioselective formation of chiral cnolates from achiral ketones," Tetrahedron Letters 41(36):6941-6944 (2000).

(56) References Cited

OTHER PUBLICATIONS

Caira, "Crystalline Polymorphism of Organic Compounds," Topics in Current Chemistry, vol. 198, pp. 163-208, Jan. 1998.
Campagne, J.-M. et al., "Synthesis of Mixed Phosphonate Diester Analogues of Dipeptides using BOP or PyBOP Reagents," Tetrahedron Left. 34(42), 6743-6744, Pergamon Press Ltd. (1993).
Campbell, DA, "The Synthesis of Phosphonate Esters, an Extension of the Mitsunobu Reaction," J. Org. Chem. 57,6331-6335, American Chemical Society (1992).
CAS Registry No. 852460-16-3, STN Entry Date Jun. 17, 2005.
CAS Registry No. 131055-48-6, STN Entry Date Dec. 14, 1990.
CAS Registry No. 127192-35-2, STN Entry Date May 18, 1990.
CAS Registry No. 141740-28-5, STN Entry Date Jun. 12, 1992.
CAS Registry No. 141220-32-8, STN Entry Date May 8, 1992.
CAS Registry No. 127192-36-3, STN Entry Date May 18, 1990.
CAS Registry 699001-74-6, STN Entry Date Jun. 25, 2004.
Casara, P.J. et al., Synthesis of Acid Stable 5'-O-Fluoromethyl Phosphonates of Nucleosides. Evaluation as Inhibitors of Reverse Transcriptase, • Bioorg. Med. Chem. Left. 2(2), 145-148, Pergamon Press pic. (1992).
Cereda et al., "Solid-phase synthesis of 3-hydroxymethyl isoxazoles via resin bound nitrile oxides," Tetrahedron Lett. 42(30):4951-4953(2001).
Coppi et al., "Lewis Acid Mediated Condensation of Alkenols and Aldehydes. A Selective Synthesis of Tetrahydropyrans and Oxepanes," J. Org. Chern. 53(4) 911-913 (1988).
Curran et al., "Thermolysis ofbis[2-[(trimethylsilyl)oxy]prop-2-yl] furoxan (TOP-furoxan). The First Practical Method for Intermolecular Cycloaddition of an in Situ Generated Nitrile Oxide with 1, 2-Di- and Trisubstituted Olefins," J. Am. Chem. Soc. 107(21):6023-6028 (1985).
DeLambert et al., "N-Phosphonomethyl Dipeptides and Their Phosphonate Prodrugs, a New Generation of Neutral Endopeptidase (NEP, TIC3.4.24.11) Inhibitors," J. Med. Chem. 37(7):498-511 (1994).
Egron et al., "Synthesis and Anti-HIV Activity of Some S-Acyl-2-thioethyl (SATE) Phosphoramidate Derivatives of3' -Acido-2' 3' -dideoxythymidine," Nucleosides & Nucleotides 18(4):981-982 (1999).
Elhaddadi et al., "A Convenient Synthesis of Alkyl and Dialkyl 1-benzyloxyamino alkyl phosphonates and phosphinates," Phosphorus, Sulfur and Silicon 54:143-150 (1990).
Elliott, RL. et al., "Synthesis and Biological Evaluation of Phosphonamidate Peptide Inhibitors of Enkephalinase and Angiotensin-Converting Enzyme," J. Med. Chem. 28: 1208-1216, American Chemical Society (1985).
Farquhar et al., "Biologically Reversible Phosphate-Protective Groups," J. Pharm. Sci. 72(3):324-325 (1983).
Faulon, J-L., et al.: "The Signature Molecular Descriptor. 2. Enumerating Molecules from Their Extended Valence Sequences," Journal of Chemical Information and Computer Sciences, 2003, vol. 43, No. 3, pp. 721-734.
Federal Register 2011, 76 (27), p. 7166.
Ferres, "Pro-Drugs of B-Lactam Antibiotics," Drugs of Today 19(9):499-538 (1983).
Franchetti, P. et al.: Potent and selective inhibitors of human Immunodeficiency virus protease structurally related toL-694,746, Antiviral Chemistry and Chemotherapy, 1998, vol. 9, No. 4, pp. 303-309.
Freed et al., "Evidence for Acyloxymethyl Esters of Pyrimidine 5'-Deoxyribonucleotides as Extracellular Sources of Active 5'-Deoxyribonucleotides in Cultured Cells," Biochem. Pharmac. 38:3193-3198 (1989).
Garbisch et al., "Conformations. IV. The Conformational Preference of the Phenyl Group in Cyclohexane," J. Am. Chem. Soc., 1963, vol. 85, pp. 3228-3231.
Gibson, Ed., Pharmaceutical Preformulation and Formulation, CRC Press LLC, Boca Raton, FL, 2004.
Greene et al., Protective Groups in Organic Synthesis, John Wiley, New York, 1990.

Grundy et al., "Diagnosis and Management of the Metabolic Syndrome," Circulation, 112 (2005), p. 2735-2752.
Gupta et al., "An Improved Synthesis of Vinylic Phosphonates from Ketones," Synth. Commun. 10(4):299-304 (1980).
Hoffman, "A Simple Efficient Synthesis of Dibenzyl and Di-p-nitrobenzyl 1-Hydroxyalkanephosphonates," Synthesis 1988(1):62-64 (1988).
Huang et al., "a-Hypervalent Iodine Functionalized Phosphonium and Arsonium Ylides and Their Tandem Reaction as Umpolung Reagents," J Org. Chem. 67(23):8261-8264 (2002).
Inanaga et al., "A Rapid Esterification by Means of Mixed Anydride and Its Application to Large-ring Lactonization," Bulletin of the Chemical Society of Japan 52(7):1989-1993 (1979).
Johnson et al., "The Regulation of Gluconeogenesis in Isolated Rat Liver Cells by Glucagon, Insulan, Dibutyrl Cyclic Adenosine Monophosphate, and Fatty Acids," J. Biol. Chem., 1972, vol. 247, No. 10, pp. 3229-3235.
Juliano, Ed., Drug Delivery Systems, Oxford Univ. Press, Oxford, 1980.
Kerns et al., "Selective N-Sulfation of Glucosamine Derivatives Using Phenyl Chlorosulfate in Non-Qqueous Solvent," Synthetic Communications., 26:2671-2680, 1996.
Khamnei, S. et al., "Neighboring Group Catalysis in the Design of Nucleotide Prodrugs," J. Med. Chem. 39, 4109-4115, American Chemical Society (1996).
Kim, Cherug-ju, Controlled Release Dosage Form Design, 231-238, Technomic Publishing, Lancaster PA 2000.
Kozma, CRC Handbook of Optical resolutions via Diastereomeric Salt Formation, CRC Press, 2001.
Kurti et al., Strategic Applications of Named Reactions in Organic Synthesis, Elsvier, 340-342, 2005.
Kurukulasuriya et al., "Biaryl amide glucagon receptor antagonists," Bioorg. Med. Chem. Lett. 14(9):2047-2050 (2004).
Larock, Comprehensive Organic transformations, VCH, New York, 1989.
Latour et al., "Simple Syntheses of 2-Hydroxymethy-1, 3-propanediol and Related Compounds," Synthesis 1987(8):742-745 (1987).
Lee et al., "Synthesis and In Vitro Activity of Novel Isoxazolyl Tetrahydropyridinyl Oxazolidinone Antibacterial Agents," Bioorg. Med. Chern. Lett. 13(22):4117-4120 (2003).
Lejczak et al., Transcstcrification ofDiphenyl Phosphonates Using the Potassium Fluoride/Crown Ether/ Alcohol System; Part 2. The Use of Diphenyl 1-Aminoalkanephosphonates in Phosphonopeptide Synthesis 1982(5):412-414 (1982).
Li et al.: "Chiral Drug Separation," Encyclopedia of Chemical Processing (2006), pp. 449-458.
Lyapkalo et al., (Enantioselective Synthesis of Cyclohexenylalkenes by Asymmetric Depprotonation of 4-tert-Butylcyclohexanone Followed by O-Nonatlation and Heck Couplings, SynZett 1292-1295 (2001).
Martin et al., "Synthesis and Antiviral Activity of Various Esters of 9-[(1 ,3-Dihydroxy-2-propoxy)methyl]guanine," J. Pharm. Sci. 76(2):180-184 (1987).
Mathur, "Metabolic Syndrome" see section "How is metabolic syndrome defined?"<http://www.medicinenet.com/metabolic syndrome/article.htm>, pp. 2-3, Accessed Mar. 31, 2009.
McGuigan, C. et al., "Kinase Bypass: A New Strategy for Anti-HIV Drug Design, "Bioorganic & Medicinal Chemistry Letters 3(6): 1207-1210, Pergamon Press Ltd. (1993).
McKenna et al., "The facile dealkylation of phosphonic acid dialkyl esters by bromotrimethylsilanc," Tetrahedron Lett. 2:155-158 (1977).
Meier, C. et al., "Cyclic Saligenyl Phosphotriesters of 2',3'-Dideoxy-2',3'- didehydrothymidine (d4T)—A New Pro-Nucleotide Approach," Bioorganic Med. Chem. Lett. 7(2), 99-104, Elsevier Science Ltd. (1997).
Mitchell, A.G. et al., "Bioreversible Protection for the Phospho Group: Bioactivation of the Di(4-acyloxybenzyl) and Mono(4-acyloxybenzyl) Phosphoesters of Methylphosphonate and Phosphonacetate," J. Chem. Soc. Perkin Trans. 1 38:2345-2353, Chemical Society, London (1992).
Mitsunobu, 0., "The Use of Diethyl Azodicarboxylate and Triphenylphosphine in Synthesis and Transformation of Natural Products," Synthesis 1-28, Georg Thieme Verlag (1981).

(56) References Cited

OTHER PUBLICATIONS

Moriarty et al., "Diphenyl Methylphosphonate as a Phosphonylation Reagent with High Diastereoselectivity at Phosphorus," Tetrahedron Lett. 38(15):2597-2600 (1997).
Mukalyama et al., "Synthesis of Oligothymidylates and Nucleoside Cyclic Phosphates by Oxidation-Reduction Condensation," J. Am. Chem. Soc. 94(24):8528-8532 (1972).
Nishimura et al., "Orally Active 1-(Cyclohexyloxycarbonyloxy)alkyl Ester Prodrugs of Cefotiam," J. Antibiotics 40(1):81-90 (1987).
Ogg, M.S. et al., "A Reporter Gene Assay to Assess the Molecular Mechanisms of Xenobiotic-dependent Induction of the Human CYP3A4 Gene in Vitro," Xenobiotica 29(3), 269-279, Taylor & Francis Ltd. (Mar. 1999).
Ohashi, K. et al., "Synthesis of Phosphonosphingoglycolipid Found in Marine Snail Turbo Cornutus," Tetrahedron Lett. 29(10), 1189-1192, Pergamon Press pic. (1988).
Patois et al., "Easy preparation of alkylphosphonyl dichlorides," Bull. Soc. Chim Fr. 130:485-487 (1993).
Pelchowicz, "Organic Phosphorus Compounds. Part 1.The Reaction of Dialkyl Mthylphosphnates and Methylphosphonothianates with Inorganic Acid Chlorides," J Chern. Soc. 238-240 (1961).
Petasis et al., "The boronic acid mannich reaction: A new method for the synthesis of geometrically pure allylarnines," Tetrahedron Lett. 34(4):583-586 (1993).
Posner et al., "3-bromo-2-pyrone: an easily prepared chameleon diene and a synthetic equivalent of 2-pyrone in thermal diels-alder cycloadditions," Tetrahedron Letters 32(39):5295-5298 (1991).
PubMed Health, "Type 1 diabetes" Jun. 28, 2011.
Puech et al., "Intracellular delivery ofnucleoside monophosphates through a reductase-mediated activation process," Antiviral Res. 22(2-3):155-174 (1993).
Quast et al., "Herstellung von Methylphosphonsaure-dichlorid," Synthesis 1974(7):490 (1974).
Rabinowitz, "The Reactions of Phosphonic Acid Esters with Acid Chlorides. A Very Mild Ilydrolytic Route," J. Org. Chem. 28(11):2975-2978 (1963).
Ramachandran et al., "Efficient General Synthesis of 1,2- and 1,3-diols in High Enantiomeric Excess via the Intramolecular Asymmetric Reduction of the Corresponding Ketoalkyl Diisopinocampheylborinate Intermediates," Tetrahedron, 38(5):761-764 (1997).
Rao et al., "Studies directed towards the synthesis of immunosuppressive agent FK-506: synthesis of the entire top-half," Tetrahedron Letters 32(4):547-550 (1991).
Rathbone et al., Eds., Modified-Release Drug Deliver Technology, Drugs and the Pharmaceutical Science, Marcel Dekker, Inc.: New York, NY, vol. 126, 2003.
Remington: The Science and Practice of Pharmacy, 21st Ed., Lippincott Williams & Wilkins, Philadephia, PA, 2005.
Remington's Pharmaceutical Sciences, 18th ed., Mack Publishing, Easton PA, 173, 1990, and pp. 172-174.
Roche, Ed., Design of Biopharmaceutical Properties through Prodrugs and Analogs, American Pharmaceutical Association, Washington, 1977.
Roden et al., "The Roles of Insulin and Glucagon in the Regulation of Hepatic Glycogen Synthesis and Turnover in Humans," J. Clin. Invest. 1996, vol. 97, No. 3, pp. 642-648.
Rosowsky et al., "Methotrexate Analogues. 32. Chain Extension, a-Carboxyl Delection, and y-Carboxyl Replacement by Sulfonate and Phosphonate: Effect on Enzyme Binding and Cell-Growth Inhibition," J. Med. Chem. 31: 1326-1331 (1988).
Rowe et al., Eds., Handbook of Pharmaceutical Excipients, 5th Ed., The Pharmaceutical Press and the Merican Pharmaceutical Association, 2006.
Sakamoto et al., "The palladium-catalyzed arylation of 4H-1,3-dioxin," Tetrahedron Lett. 33(45):6845-6848 (1992).
San Diego, "Ligand Initiates Phase 1 Trial with Glucagon Receptor Antagonist for Type 2 Diatests," Diabetes Week, Nov. 25, 2013.

Schoeller, et al., "Measurement of energy expenditure in humans by doubly labeled water method," J. Appl Physiol., 53(4), pp. 955-959, (1982).
Serafinowska et al., "Synthesis and in Vivo Evaluation of Prodrugs of 9-[2-(Phosphonomethoxy)ethoxy]adenine," J. Med. Chem. 38(8):1372-1379 (1995).
Shafer et al., "On the Mechanism of Reductive Cleavage of Aryl Phosphates," J. Am. Chem. Soc. 99(15):5118-5123 (1977).
Shaw-Ponter et al., "New synthesis of both D- and L-3-O-Carbamoyl-2-deoxy-4-thioribosides, Substrates for I)-selective Glycosylations," Tetrahedron Letters 37:1871-1874 (1981).
Shono et al., "Electroreductive Elimination of Phenolic Hydroxyl Groups and a New Synthesis of Olivetol," J. Org. Chem. 44(25):4508-4511.
Siddiqui et al., "The Presence of Substituents on the Aryl Moeity of the Aryl Phosphoramidate Derivative of d4T Enhances Anti-HIV Efficacy in Cell Culture: A Structure-Activity Relationship," J. Med. Chem. 42: 393-399 (1999).
Silverman, Chapter 8: "Prodrugs and Drug Delivery Systems", The Organic Chemistry of Drug Design and Drug Action, Academic Press, 1992, pp. 352-401.
Singh et al., "Design and Synthesis oflsoxazole Containing Bioisosteres of Epihatidine as Potent Nicotinic Acetylcholine Receptor Agonists," Chem. Pharm. Bull. 47(10):1501-1505 (1999).
Slavica et al., "Systhesis and Biological Activities of a New Set of Irreversibly Acting 2-(4'-Isothiocyanatobenzyl)imidazoline Analogs in Rat Thoracic Aorta," J. Med. Chem. 1994, vol. 37, No. 12, pp. 1874-1881.
Starrett, Jr. et al., "Synthesis, Oral Bioavailability Determination, and in Vitro Evaluation of Prodrugs of the Antiviral Agent 9-[2-(Phosphonomethoxy)ethyl]adenine (PMEA)," J. Med, Chem 37:1857-1864 (1994).
Still et al., "Direct synthesis of Z-unsaturated esters. A useful modification of the hormer-emmons olefination," Tetrahedron Letters 24(41):4405-4408 (1983).
Stowell et al., "The Mild Preparation of Synthetically Useful Phosphonic Dichlorides: Applicationt to the Synthesis of Cyclic Phosphonic Diesters and Diamides," Tetrahedron Letters 31(23):3261-3262 (1990).
Tawfik et al., "1,8-Diazabicyclo[5.4.0]undecene Mediated Transesterification ofp-Nitrophenyl Phosphonates: A Novel Route to Phosphono Esters," Synthesis 1993(10):968-972 (1993).
Toke et al., "A Versatile Building Block for the Synthesis of Substituted Cyclopropanephosphonic Acid Esters," Tetrahedron Letters 51(33):9167-9178 (1995).
Turner, JA, "A General Approach to the Synthesis of 1,6-,1,7-, and 1,8- Naphthyridines," J. Org. Chem. 55(15),4744-4750, American Chemical Society (1990).
United States Pharmacopeia, The, 23rd ed., pp. 1843-1844, 1995.
Vajda et al., "Pharmacokinetics and pharmacodynamics of single and multiple doses of the glucagon receptor antagonist LGD-6972 in healthy subjects and subjects with type 2 diabetes mellitus," Diabetes, Obesity and Metabolism, vol. 19, No. 1, Aug. 31, 2016.
Valette et al., "Decomposition Pathways and in Vitro HIV Inhibitory Effects of IsoddA Pronucleotides: Toward a Rational Approach for Intracellular Delivery of Nucleotide 5'-Monophosphates," J. Med. Chem. 39(10):1981-1990 (1996).
Vanderwal et al., "An Enantioslcctivc Synthesis of FR182877 Provides a Chemical Rationalization oflts Structure and Affords Multigram Quantities of Its Direct Precursor," J. Am. Chem. Soc. 125(18):5393- 5407.
Xu et al., "A General Route to the Synthesis of N-Protected 1-Substituted and 1,2-Disubstituted Taurines," Synthesis 2004(2):276-282 (2004).
Yamamoto et al., "Synthesis of Pyridine N-Oxide-SbCls Complexes and Their Intramolecular and Oxygen-Transfer Reaction," Tetrahedron 37:1871-1873 (1981).
Yan et al., "Preparation, Properties, Reactions, and Adenosine Receptor Affinities of Sulfophenylxanthine Nitrophenyl Esters: Toward the Development of Sulfonic Acid Prodrugs with Peroral Bioavailability," J. Med. Chem. 47(4):1031-1043 (2004).

(56) References Cited

OTHER PUBLICATIONS

Yao et al., "Generation of Nitroalkanes, Hydroximoyl Halides and Nitrile Oxides from the Reactions of B-Nitrostyrenes with Grignard or Organolithium Reagents," Tetrahedron Letters 54(5/6):791-822 (1998).

Younker et al., "A mechanistic Study of the Alkaline Hydrolysis of Diaryl Sulfate Diesters," J. Org. Chem. 69(26):9043-9048 (2004).

Ballatore: "Carboxylic Acid (Bio)Isosteres in Drug Design," ChemMedChem 8.3 (2013): 385-395.

R. Jason Herr: "5-Substituted-1H-tetrazoles as Carboxylic Acid Isosteres: Medicinal Chemistry and Synthetic Methods," Bioorg. Med. Chem. 10 (2002) 3379-3393.

Macchiarulo, et al.: "Exploring the other side of bilogically relevant chemical space: Insights into carboxylic, sulfonic and phosphonic acid bioisosteric relationships Roberto Pellicciari," Journal of Molecular Graphics and Modelling 26 (2007) 728-739.

Lidia Moerira Lima, et al.: "Bioisosterism: A Useful Strategy for Molecular Modificaion and Drug Design, Current Medicinal Chemistry," 2005, 12, 23-49.

International Invitation to Pay Additional Fees, re PCT Application No. PCT/US2019/017833, dated Apr. 17, 2019.

International Search Report, re PCT Application No. PCT/US2019/017833, dated Aug. 22, 2019.

International Preliminary Report on Patentability, re PCT Application No. PCT/US2019/017833, dated Aug. 18, 2020.

Braga, et al., "Crystal Polymorphism and Multiple Crystal Forms," Struct Bond (2009) 132: 25-50.

Cruz-Cabeza et al., "Chamical Society Reviews", Facts and fictgions about polymorphism, Chemical Society Reviews (RSC Publishing), Issue 23, 2015.

Dunitz, et al., "Disappearing Polymorphs," Acc. Chem. Res. 1995, 28, 193-200.

Hilfiker, et al., "Relevance of Solid-state properties for Pharmaceutical Products," Polymorphism in the Pharmaceutical Industry, Jan. 1, 2006, pp. 1-19.

Hursthouse, et al., "Why Do Organic Compounds Crystallise Well or Badly or Ever so Slowly? Why Is Crystallisation Nevertheless Such a Good Purification Technique?" Organic Process Research and Development 2009, 13, 1231-1240.

\* cited by examiner

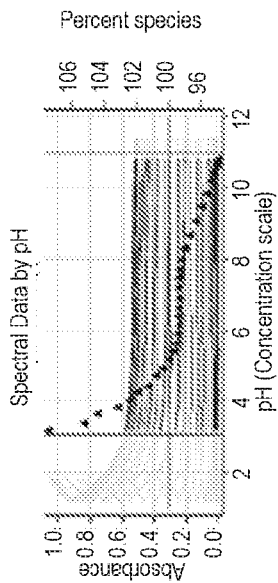
FIG. 10A
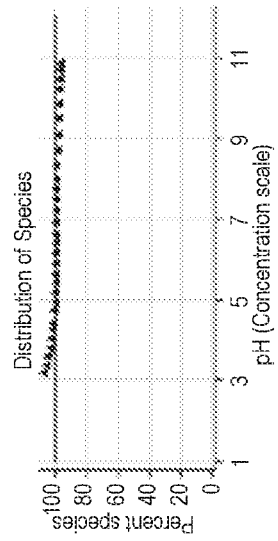
FIG. 10B
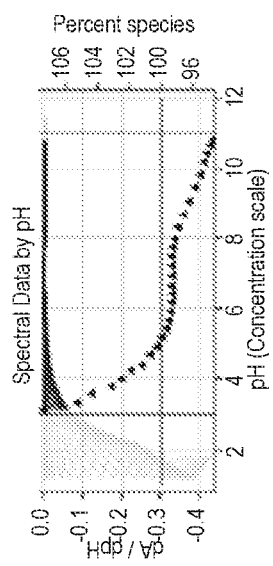
FIG. 10C
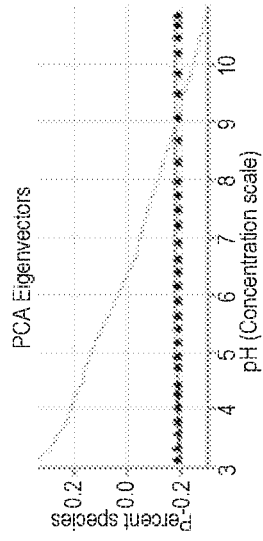
FIG. 10D
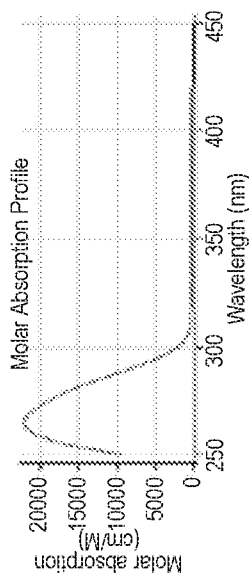
FIG. 10E
FIG. 10F

GLUCAGON RECEPTOR ANTAGONISTS

CROSS-REFERENCE TO RELATED APPLICATIONS

The present application claims the benefit of U.S. Provisional Application No. 62/630,190, filed on Feb. 13, 2018, and U.S. Provisional Application No. 62/635,461, filed on Feb. 26, 2018, each of which is incorporated herein by reference in its entirety.

FIELD

Provided are compounds capable of acting as antagonists of receptors. Some embodiments relate to antagonists of glucagon receptors. In some embodiments, sulfonate compounds and compositions are provided for use in treatment, prevention or amelioration of one or more symptoms, causes or effects of a glucoregulatory or glucagon receptor-mediated disease or disorder.

BACKGROUND

Glucagon is believed to be a 29-amino acid pancreatic hormone which is secreted from the pancreatic α cells into the portal blood supply in response to hypoglycemia. It has been observed to act as a counterregulatory hormone to insulin. Some physiological effects of glucagon are mediated by its interaction with glucagon receptors in the liver, followed by activation of adenylate cyclase to increase intracellular cAMP levels. The observed result is an increase in glycogenolysis and gluconeogenesis, with attenuations of the ability of insulin to inhibit these metabolic processes (Johnson et al., J. Biol. Chem. 1972, 247, 3229-3235). Overall rates of hepatic glucose synthesis and glycogen metabolism may be controlled by the systemic ratio of insulin and glucagon (Roden et al., J. Clin. Invest. 1996, 97, 642-648; Brand et al., Diabetologia 1994, 37, 985-993).

Diabetes is a disease characterized by elevated levels of plasma glucose. Uncontrolled hyperglycemia is associated with an increased risk for microvascular and macrovascular diseases, including nephropathy, retinopathy, hypertension, stroke, and heart disease, for example. Control of glucose homeostasis is a major approach to the treatment of diabetes. It has been demonstrated in healthy animals as well as in animal models of types I and II diabetes that removal of circulating glucagon with selective and specific antibodies results in reduction of the glycemic level. One potential treatment for diabetes and other diseases involving impaired glycemia is to block a glucagon receptor with a glucagon receptor antagonist to improve insulin responsiveness, and decrease the rate of gluconeogenesis, and/or to lower plasma glucose levels by reducing the rate of hepatic glucose output in a patient.

Diabetic ketoacidosis is a complex disordered metabolic state characterized by hyperglycemia, acidosis, and ketonaemia and continues to have high rates of morbidity and mortality despite advances in the treatment of diabetes mellitus. DKA usually occurs as a consequence of absolute or relative insulin deficiency that is accompanied by an increase in counter regulatory hormones (i.e., glucagon, cortisol, growth hormone, catecholamines). DKA accounts for the majority of hospitalizations due to diabetes, especially in children, and accounts for 20% of all deaths related to diabetes (Krane, 1988). DKA is characterized by hyperglycemia (blood glucose levels greater than 250 mg/dL), acidosis (pH less than 7.3), and the presence of ketones in the urine. DKA has been considered to be indicative, or even diagnostic, of type 1 diabetes, but increasingly there are cases of ketone-prone type 2 diabetes being recognized.

Some glucagon receptor antagonists that demonstrate highly potent biological activities are carboxylic compounds and bind to glucagon receptors at an allosteric site at the edge of transmembrane. The carboxylic group of the antagonists plays a role in the binding affinity and the conformation of the glucagon receptor, where the two oxygen atoms of the carboxylic acid have hydrogen bond interactions with the receptor based on the bond distances in the resolved X-ray structure of glucagon receptor and the inhibitor compound MK-0893. Sulfonate compounds have chemical and physical properties that are quite different from the carboxylate compounds and, as a result, sulfonic acid is not generally considered as a biostere of carboxylic acid by medicinal chemists. Not all compounds that are glucagon antagonists have characteristics affording the best potential to become useful therapeutics. Some of these characteristics include high affinity at the glucagon receptor, certain conformations of the antagonized glucagon receptor, duration of receptor deactivation, oral bioavailability, tissue distribution, and stability (e.g., ability to formulate or crystallize, shelf life). Favorable characteristics can lead to improved safety, tolerability, efficacy, therapeutic index, patient compliance, cost efficiency, manufacturing ease, etc.

SUMMARY

Provided herein are compounds, including enantiomerically pure and substantially enantiomerically pure forms thereof, polymorphs, crystal forms and pharmaceutically acceptable salts or co-crystals and prodrugs thereof which have glucagon receptor antagonist or inverse agonist activity. Further, provided herein are pharmaceutical compositions comprising the same, as well as methods of treating, preventing, delaying the time to onset or reducing the risk for the development or progression of a disease or condition for which one or more glucagon receptor antagonist is indicated, including without limitation Type I and II diabetes, insulin resistance, hyperglycemia, ketoacidosis, or ketosis. Moreover, provided herein are methods of making or manufacturing compounds disclosed herein, including enantiomerically pure forms thereof, and pharmaceutically acceptable salts or co-crystals and prodrugs thereof. It has been unexpectedly discovered that specific stereochemistry and functional groups of the compounds of the present embodiments exhibit one or more desired characteristics, including markedly improved receptor binding properties, oral bioavailability, and/or other advantageous features that enhance their suitability for therapeutic use.

In another aspect, provided herein are solid state forms of (R)-2-(4-(2-(4'-(tert-butyl)-[1,1'-biphenyl]-4-yl)-3-oxo-3-((2',4',6'-trimethyl-[1,1'-biphenyl]-4-yl)amino)propyl)benzamido)ethane-1-sulfonic acid (Compound 1) or salts thereof. In one embodiment, provided herein is an amorphous form of sodium salt of Compound 1. In one embodiment, provided herein is a crystalline polymorphic form of sodium salt of Compound 1 (Form A). In another embodiment, provided herein is a crystalline polymorphic form of calcium salt of Compound 1 (Form B). In yet another embodiment, provided herein is a crystalline polymorphic form of potassium salt of Compound 1 (Form C).

In another aspect, provided herein are methods of making solid state forms of Compound 1 or salts thereof. In one embodiment, provided herein is a method of making an amorphous form of Compound 1. In one embodiment, provided herein is a method of making an amorphous form of sodium salt of Compound 1. In another embodiment, provided herein is a method of making crystalline polymorphic form of sodium salt of Compound 1 (Form A). In another embodiment, provided herein is method of making a crystalline polymorphic form of calcium salt of Compound 1 (Form B). In yet another embodiment, provided herein is a method of making crystalline polymorphic form of potassium salt of Compound 1 (Form C).

In another aspect, provided herein are processes for the large scale preparation of Compound 1 or salts thereof. In one embodiment, provided herein is a large scale production of Compound 1. In one embodiment, provided herein is a large scale production of a sodium salt of Compound 1. In another embodiment, provided herein are intermediates used in the preparation of Compound 1 and processes for preparing the intermediates.

In another aspect, provided herein are pharmaceutical compositions comprising one or more solid state forms of Compound 1 or salts thereof. In one embodiment, provided herein is a pharmaceutical composition comprising an amorphous form of Compound 1. In one embodiment, provided herein is a pharmaceutical composition comprising an amorphous form of sodium salt of Compound 1. In one embodiment, provided herein is a pharmaceutical composition comprising a crystalline polymorphic form of sodium salt of Compound 1 (Form A). In another embodiment, provided herein is a pharmaceutical composition comprising a crystalline polymorphic form of calcium salt of Compound 1 (Form B). In yet another embodiment, provided herein is a pharmaceutical composition comprising a crystalline polymorphic form of potassium salt of Compound 1 (Form C). In another embodiment, provided herein is a pharmaceutical composition comprising a mixture of solid state forms selected from the group consisting of amorphous Compound 1, amorphous sodium salt of Compound 1, Polymorph Form A, Polymorph Form B, and Polymorph Form C.

In another aspect, provided herein are methods of making pharmaceutical compositions which comprise one or more solid state forms of Compound 1 or salts thereof. In one embodiment, provided herein is a method of making a pharmaceutical composition which comprises an amorphous form of Compound 1. In one embodiment, provided herein is a method of making a pharmaceutical composition which comprises an amorphous form of sodium salt of Compound 1. In one embodiment, provided herein is a method of making a pharmaceutical composition which comprises a crystalline polymorphic form of sodium salt of Compound 1 (Form A). In another embodiment, provided herein is a method of making a pharmaceutical composition which comprises a crystalline polymorphic form of calcium salt of Compound 1 (Form B). In yet another embodiment, provided herein is a method of making a pharmaceutical composition which comprises a crystalline polymorphic form of potassium salt of Compound 1 (Form C). In yet another embodiment, provided herein is a method of making a pharmaceutical composition which comprises a mixture of solid state forms selected from a group consisting of amorphous Compound 1, amorphous sodium salt of Compound 1, Polymorph Form A, Polymorph Form B, and Polymorph Form C.

In another aspect, provided herein is a method of treating, preventing, or ameliorating a condition, disorder, or disease associated with a glucagon receptor, or one or more symptoms thereof, comprising administering to a subject having, showing symptoms of, or being suspected to have such a condition, disorder, or disease, a therapeutically effective amount of one or more solid state forms of Compound 1 or salts thereof, or pharmaceutical compositions thereof. In one embodiment, the solid state form is an amorphous form of Compound 1. In one embodiment, the solid state form is an amorphous form of sodium salt of Compound 1. In another embodiment, the solid state form is a crystalline polymorphic form of sodium salt of Compound 1 (Form A). In another embodiment, the solid state form is a crystalline polymorphic form of calcium salt of Compound 1 (Form B). In another embodiment, the solid state form is a crystalline polymorphic form of potassium salt of Compound 1 (Form C).

In another aspect, provided herein is a method of treating, preventing, or ameliorating a condition, disorder, or disease responsive to the modulation of a glucagon receptor (GCGR), or one or more symptoms thereof, comprising administering to a subject having, showing symptoms of, or being suspected to have such a condition, disorder, or disease, a therapeutically effective amount of one or more solid state forms of Compound 1 or salts thereof, or pharmaceutical compositions thereof. In one embodiment, the solid state form is an amorphous form of Compound 1. In one embodiment, the solid state form is an amorphous form of sodium salt of Compound 1. In another embodiment, the solid state form is a crystalline polymorphic form of sodium salt of Compound 1 (Form A). In another embodiment, the solid state form is a crystalline polymorphic form of calcium salt of Compound 1 (Form B). In another embodiment, the solid state form is a crystalline polymorphic form of potassium salt of Compound 1 (Form C).

In another aspect, provided herein is a method of treating, preventing, or ameliorating a GCGR-mediated condition, disorder, or disease, or one or more symptoms thereof, comprising administering to a subject having or being suspected to have such a condition, disorder, or disease, a therapeutically effective amount of one or more solid state forms of Compound 1 or salts thereof, or pharmaceutical compositions thereof. In one embodiment, the solid state form is an amorphous form of Compound 1. In one embodiment, the solid state form is an amorphous form of sodium salt of Compound 1. In another embodiment, the solid state form is a crystalline polymorphic form of sodium salt of Compound 1 (Form A). In another embodiment, the solid state form is a crystalline polymorphic form of calcium salt of Compound 1 (Form B). In another embodiment, the solid state form is a crystalline polymorphic form of potassium salt of Compound 1 (Form C).

In another aspect, provided herein is a method of treating, preventing, or ameliorating a condition, disorder, or disease responsive to a decrease in the hepatic glucose production or in the blood glucose level of a subject, or one or more symptoms thereof, comprising administering to the subject a therapeutically effective amount of one or more solid state forms of Compound 1 or salts thereof, or pharmaceutical compositions thereof. In one embodiment, the solid state form is an amorphous form of Compound 1. In one embodiment, the solid state form is an amorphous form of sodium salt of Compound 1. In another embodiment, the solid state form is a crystalline polymorphic form of sodium salt of Compound 1 (Form A). In another embodiment, the solid state form is a crystalline polymorphic form of calcium salt of Compound 1 (Form B). In another embodiment, the solid state form is a crystalline polymorphic form of potassium salt of Compound 1 (Form C).

In another aspect, provided herein is a method of modulating the biological activity of a glucagon receptor, comprising contacting the receptor with a therapeutically effective amount of one or more solid state forms of Compound 1 or salts thereof, or pharmaceutical compositions thereof. In one embodiment, the solid state form is an amorphous form of Compound 1. In one embodiment, the solid state form is an amorphous form of sodium salt of Compound 1. In another embodiment, the solid state form is a crystalline polymorphic form of sodium salt of Compound 1 (Form A). In another embodiment, the solid state form is a crystalline polymorphic form of calcium salt of Compound 1 (Form B). In another embodiment, the solid state form is a crystalline polymorphic form of potassium salt of Compound 1 (Form C).

In another aspect, pharmaceutical compositions are provided comprising a compound provided herein, e.g., a compound of Formula I or II, including a single enantiomer, a mixture of enantiomers, or a mixture of diastereomers thereof a mixture of compounds of Formula I and II, or a pharmaceutically acceptable salt, solvate, or prodrug thereof in combination with one or more pharmaceutically acceptable carriers.

Further provided herein is a method of treating, preventing, or ameliorating a condition, disorder, or disease associated with a glucagon receptor, or one or more symptoms thereof, comprising administering to a subject having, showing symptoms of, or being suspected to have such a condition, disorder, or disease, a therapeutically effective amount of a compound provided herein, e.g., a compound of Formula I or II (or a combination of both), or a pharmaceutically acceptable salt, solvate, or prodrug thereof.

Additionally, provided herein is a method of treating, preventing, or ameliorating a condition, disorder, or disease responsive to the modulation of a glucagon receptor (GCGR), or one or more symptoms thereof, comprising administering to a subject having, showing symptoms of, or being suspected to have such a condition, disorder, or disorder, a therapeutically effective amount of a compound provided herein, e.g., a compound of Formula I or II (or a combination thereof), or a pharmaceutically acceptable salt, solvate, or prodrug thereof or a pharmaceutical composition thereof.

Also provided herein is a method of treating, preventing, or ameliorating a GCGR-mediated condition, disorder, or disease, or one or more symptoms thereof, comprising administering to a subject having or being suspected to have such a condition, disorder, or disease, a therapeutically effective amount of a compound provided herein, e.g., a compound of Formula I or II (or a combination thereof), or a pharmaceutically acceptable salt, solvate, or prodrug thereof or a pharmaceutical composition thereof.

Further provided herein is a method of treating, preventing, or ameliorating a condition, disorder, or disease responsive to a decrease in the hepatic glucose production or in the blood glucose level, or one or more symptoms of, comprising administering to a subject in need thereof a therapeutically effective amount of a compound provided herein, e.g., a compound of Formula I or II (or a combination thereof), or a pharmaceutically acceptable salt, solvate, or prodrug thereof or a pharmaceutical composition thereof.

Additionally provided herein is a method of modulating the biological activity of a glucagon receptor, comprising contacting the receptor with one or more of the compounds provided herein, e.g., a compound of Formula I or II (or a combination thereof), or a pharmaceutically acceptable salt, solvate, or prodrug thereof or a pharmaceutical composition thereof.

These and other aspects of the present embodiments will be more clearly understood with reference to the following detailed description.

BRIEF DESCRIPTION OF THE DRAWINGS

FIG. 10A shows a spectral graph by wavelength for UV metric determination of Polymorph Form A with 60v % DMSO as initial cosolvent.

FIG. 10B shows a spectral graph by pH for UV metric determination of Polymorph Form A with 60v % DMSO as initial cosolvent.

FIG. 10C shows a spectral graph by pH for UV metric determination of Polymorph Form A with 60v % DMSO as initial cosolvent.

FIG. 10D shows a graph of distribution of species for UV metric determination of Polymorph Form A with 60v % DMSO as initial cosolvent.

FIG. 10E shows a graph of molar absorption for UV metric determination of Polymorph Form A with 60v % DMSO as initial cosolvent.

FIG. 10F shows a graph of PCA eigenvector for UV metric determination of Polymorph Form A with 60v % DMSO as initial cosolvent.

DETAILED DESCRIPTION

Definitions

Figure 1:
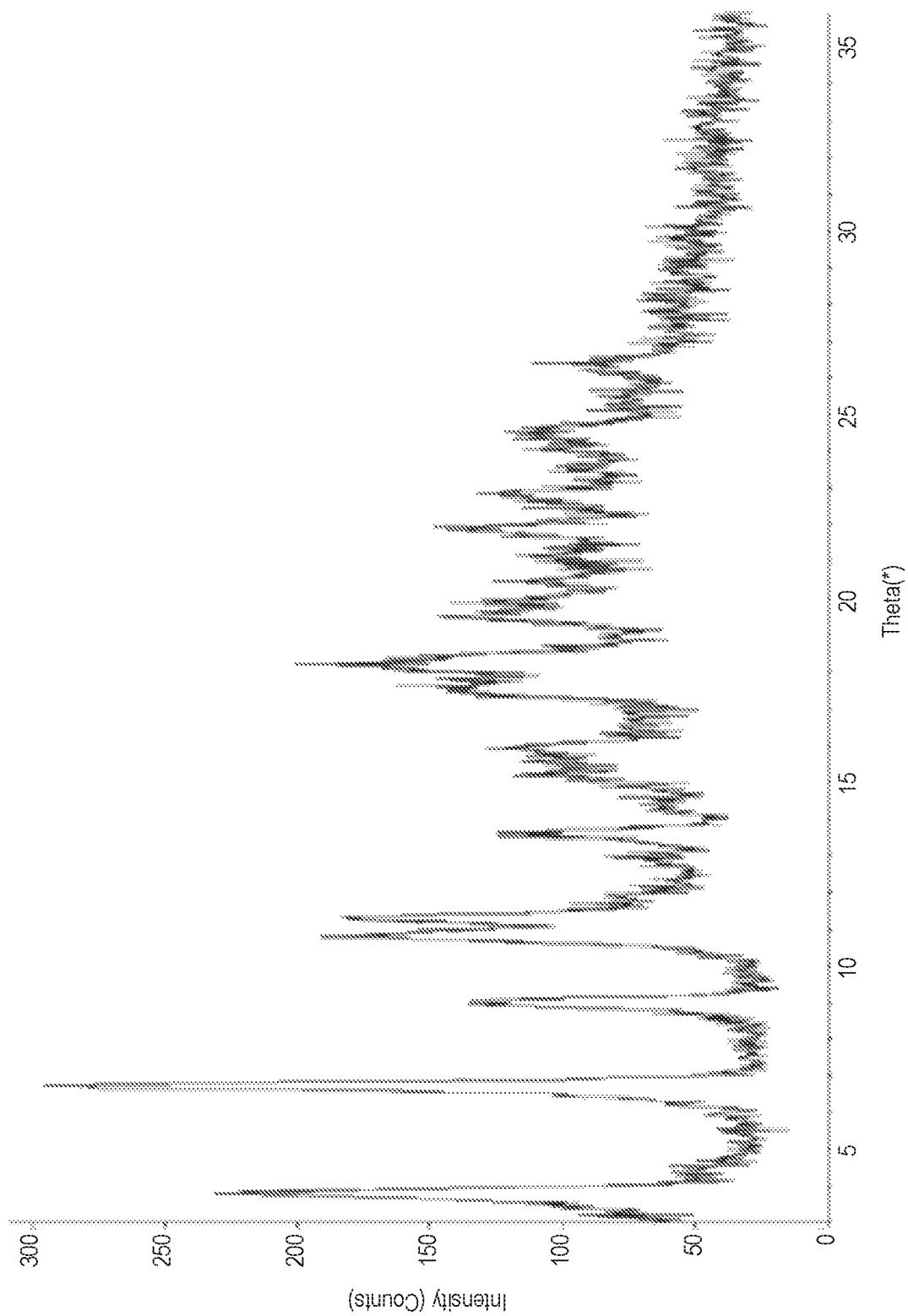
FIG. 1 is an X-Ray Powder Diffraction ("XRPD") pattern for Polymorph Form A.

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

In this specification and the appended claims, the singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "Compound 1" refers to the single enantiomer (R)-2-(4-(2-(4'-(tert-butyl)-[1,1'-biphenyl]-4-yl)-3-oxo-3-((2',4',6'-trimethyl-[1,1'-biphenyl]-4-yl)amino)propyl)benzamido)ethane-1-sulfonic acid.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptom(s); barring a subject from acquiring a disease; or reducing a subject's risk of acquiring a disorder, disease, or condition.

The term "therapeutically effective amount" is meant to include the amount of a compound that, when administered, is sufficient to prevent development of, or alleviate to some extent, one or more of the symptoms of a disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

The term "$IC_{50}$" refers to an amount, concentration, or dosage of a compound that is required for 50% inhibition of a maximal response in an assay that measures such response.

The terms "pharmaceutically acceptable carrier," "pharmaceutically acceptable excipient," "physiologically acceptable carrier," or "physiologically acceptable excipient" refer to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See Remington: The Science and Practice of Pharmacy, 21st Edition, Lippincott Williams & Wilkins: Philadelphia, PA, 2005; Handbook of Pharmaceutical Excipients, 5th Edition, Rowe et al., Eds., The Pharmaceutical Press and the American Pharmaceutical Association: 2005; and Handbook of Pharmaceutical Additives, 3rd Edition, Ash and Ash Eds., Gower Publishing Company: 2007; Pharmaceutical Preformulation and Formulation, Gibson Ed., CRC Press LLC: Boca Raton, FL, 2004 (incorporated herein by reference).

The terms "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "glucagon receptor" or "GCGR" refers to a glucagon receptor protein or variant thereof, which is capable of mediating a cellular response to glucagon in vitro or in vivo. GCGR variants include proteins substantially homologous to a native GCGR, e.g., proteins having one or more naturally or non-naturally occurring amino acid deletions, insertions, or substitutions (e.g., GCGR derivatives, homologs, and fragments), as compared to the amino acid sequence of a native GCGR. In certain embodiments, the amino acid sequence of a GCGR variant is at least about 80% identical, at least about 90% identical, or at least about 95% identical to a native GCGR. In certain embodiments, the GCGR is a human glucagon receptor.

The term "glucagon receptor antagonist" or "GCGR antagonist" refers to a compound that, e.g., partially or completely blocks, decreases, prevents, inhibits, or downregulates GCGR activity. These terms also refer to a compound that binds to, delays the activation of, inactivates, or desensitizes GCGR. A GCGR antagonist may act by interfering with the interaction of glucagon with GCGR. Glucagon receptor antagonists include, e.g., US20040014789, US20040152750A1, WO04002480A1, U.S. Pat. No. 6,881, 746B2, WO03053938A1, US20030212119, US20030236292, WO03048109A1, WO03048109A1, WO00069810A1, WO02040444A1, U.S. Pat. No. 6,875, 760B2, US20070015757A, WO04050039A2, US20060116366A1, WO04069158A2, WO05121097A2, WO05121097A2, WO07015999A2, US20070203186A 1, US20080108620A1, US20060084681A1, WO04100875A2, WO05065680A1, US20070105930A1. U.S. Pat. No. 7,301,036B2, US20080085926A1, WO08042223A1. WO07047177A1, US20070088071A 1, WO07111864A2, WO06102067A1, WO07136577A2, WO06104826A2, WO05118542A1, WO05123668A1, WO06086488, WO07106181A2, WO07114855A2, US20070249688A1, WO07123581A1, WO06086488A2, WO07120270A2, WO07120284A2, and US20080125468A1. Chiral glucagon receptor antagonists include, e.g., WO2008098244, U.S. Pat. Nos. 8,710,236, 9,169,201, 9,701,626, WO2010019830A1, U.S. Pat. No. 8,907,103B2, U.S. Pat. No. 9,783,494B2, WO2015191900, and US20170216229.

The term "GCGR-mediated condition, disorder, or disease" refers to a condition, disorder, or disease characterized by inappropriate, e.g., less than or greater than normal, GCGR activity. Inappropriate GCGR functional activity might arise as the result of an increase in glucagon concentration, GCGR expression in cells which normally do not express GCGR, increased GCGR expression or degree of intracellular activation, leading to, e.g., abnormal plasma glucose levels; or decreased GCGR expression. A GCGR-mediated condition, disorder or disease may be completely or partially mediated by inappropriate GCGR activity. A GCGR-mediated condition, disorder or disease is one in which modulation of GCGR results in some effect on the underlying symptom, condition, disorder, or disease, e.g., a GCGR antagonist results in some improvement in at least some of patients being treated.

The term "optically active" refers to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "solvate" refers to a compound provided herein or a salt thereof, which further includes a stoichiometric or non-stoichiometric amount of solvent bound by non-covalent intermolecular forces. Where the solvent is water, the solvate is a hydrate. Where the solvent includes ethanol, the compound can be an ethanol solvate.

"Binding" means the specific association of the compound of interest to the target of interest, e.g., a receptor.

The term "crystalline" and related terms used herein, when used to describe a substance, component or product, means that the substance, component or product is crystalline as determined by X-ray diffraction. See, e.g., *Remington's Pharmaceutical Sciences*, 18$^{th}$ ed., Mack Publishing, Easton PA, 173 (1990); *The United States Pharmacopeia*, 23$^{rd}$ ed., 1843-1844 (1995) (incorporated herein by reference).

"Co-crystal" as used herein means a crystalline material comprised of two or more unique solids at room temperature that are H-bonded.

"Diabetes" refers to a heterogeneous group of disorders associated with impaired glucose tolerance. Its diagnosis and characterization, including pre-diabetes, type I and type II diabetes, and a variety of syndromes characterized by impaired glucose tolerance, impaired fasting glucose, and abnormal glycosylated hemoglobin, are well known in the art. It may be characterized by hyperglycemia, glycosuria, ketoacidosis, neuropathy or nephropathy, increased hepatic glucose production, insulin resistance in various tissues, insufficient insulin secretion and enhanced or poorly controlled glucagon secretion from the pancreas.

The term "EC$_{50}$" refers an amount, concentration, or dosage of a compound at which 50% of a maximal response is observed in an assay that measures such response.

The term "percent enantiomeric excess (% ee)" refers to optical purity. It is obtained by using the following formula:

$$\frac{[R] - [S]}{[R] + [S]} \times 100 = \% R - \% S$$

where [R] is the amount of the R isomer and [S] is the amount of the S isomer. This formula provides the % ee when R is the dominant isomer.

The term "enantiomerically pure" refers to a compound which comprises at least about 80% by weight of the designated enantiomer and at most about 20% by weight of the other enantiomer or other stereoisomer(s), at least about 90% by weight of the designated enantiomer and at most about 10% by weight of the other enantiomer or other stereoisomer(s), at least about 95% by weight of the designated enantiomer and at most about 5% by weight of the other enantiomer or other stereoisomer(s), at least about 96.6% by weight of the designated enantiomer and at most about 3.4% by weight of the other enantiomer or other stereoisomer(s), at least about 97% by weight of the designated enantiomer and at most about 3% by weight of the other enantiomer or other stereoisomer(s), at least about 98% by weight of the designated enantiomer and at most about 2% by weight of the other enantiomer or other stereoisomer(s), at least about 99% by weight of the designated enantiomer and at most about 1% by weight of the other enantiomer or other stereoisomer(s), at least about 99.5% by weight of the designated enantiomer and at most about 0.5% by weight of the other enantiomer or other stereoisomer(s), or at least about 99.9% by weight of the designated enantiomer and at most about 0.1% by weight of the other enantiomer or other stereoisomer(s). In certain embodiments, the weights are based upon total weight of the compound.

The term "chiral" as used herein includes a compound that has the property that it is not superimposable on its mirror image.

"Insulin resistance" is defined clinically as the impaired ability of a known quantity of exogenous or endogenous insulin to increase whole body glucose uptake and utilization.

"Impaired glucose tolerance (IGT)" refers to a condition known to precede the development of overt Type 2 diabetes. It is characterized by abnormal blood glucose excursions following a meal. The criteria for diagnosing and characterizing impaired glucose tolerance and related syndromes are well known in the art.

The term "ketosis" refers to a metabolic state characterized by raised levels of ketone bodies in the body tissues, which is a typical pathology in conditions such as diabetes, or may be the consequence of a diet that is very low in carbohydrates.

The term "ketoacidosis" refers to a metabolic state associated with high concentrations of ketone bodies, formed by breakdown of fatty acids and the deamination of amino acids. The two common ketones produced in humans are acetoacetic acid and β-hydroxybutyrate. Three common causes of ketoacidosis are alcohol, starvation, and diabetes, resulting in alcoholic ketoacidosis, starvation ketoacidosis, and diabetic ketoacidosis, respectively. In ketoacidosis, the body fails to adequately regulate ketone production causing such a severe accumulation of keto acids that the pH of the blood is substantially decreased The term "diabetic ketoacidosis" refers to a condition observed in uncontrolled diabetic patients resulting in increased production of ketone bodies, e.g., acetoacetic acid and β-hydroxybutyric acid.

"Lower" referred to herein in connection with organic radicals or compounds respectively defines such radicals or compounds as containing up to and including 6 carbon atoms. One aspect provides organic radicals or compounds as containing up to and including 4 carbon atoms. Yet another aspect provides organic radicals or compounds that contain one to three carbon atoms. Such groups may be straight chain, branched, or cyclic.

"Metabolic disease" includes diseases and conditions such as obesity, diabetes and lipid disorders such as hypercholesterolemia, hyperlipidemia, hypertriglyceridemia as well as disorders that are associated with abnormal levels of lipoproteins, lipids, carbohydrates and insulin such as metabolic syndrome X, diabetes, impaired glucose tolerance, atherosclerosis, coronary artery disease, cardiovascular disease. The criteria for diagnosing and characterizing these conditions and related syndromes are well known in the art.

"Polymorph" as used herein refers to a crystalline form of a compound or a salt, hydrate, or solvate thereof, in a particular crystal packing arrangement. All polymorphs have the same elemental composition. The term "crystalline," as used herein, refers to a solid state form which consists of orderly arrangement of structural units. Different crystalline forms of the same compound, or a salt, hydrate, or solvate thereof, arise from different packing of the molecules in the solid state, which results in different crystal symmetries and/or unit cell parameter. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystalline form to dominate. Various polymorphs of a compound, or a salt, hydrate, or solvate thereof, can be prepared by crystallization under different conditions.

Crystalline forms are most commonly characterized by X-ray powder diffraction (XRPD). An XRPD pattern of reflections (peaks, typically expressed in degrees 2-theta) is commonly considered a fingerprint of a particular crystalline form. The relative intensities of the XRPD peaks can widely vary depending on, inter alia, the sample preparation technique, crystal size distribution, filters, the sample mounting procedure, and the particular instrument employed. In some instances, new peaks may be observed or existing peaks may disappear, depending on the type of instrument or the settings. In some instances, any particular peak in an XRPD pattern may appear as a singlet, doublet, triplet, quartet, or multiplet, depending on the type of instrument or the settings, the sensitivity of the instrument, measuring conditions, and/or purity of the crystalline form. In some instances, any particular peak in an XRPD may appear in a symmetric shape or in an asymmetric shape, e.g., having a shoulder. Moreover, instrument variation and other factors can affect the 2-theta values. A skilled artisan understanding these variations is capable of discriminating or ascertaining the defining features or characteristics of a particular crystal form using XRPD, as well as using other known physicochemical techniques.

"Prodrug" as used herein refers to any compound that when administered to a biological system generates a biologically active compound as a result of spontaneous chemical reaction(s), enzyme catalyzed chemical reaction(s), and/or metabolic chemical reaction(s), or any combination thereof. Standard prodrugs are formed using groups attached to functionality, e.g., HO—, HS—, HOOC—, —NHR, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other varieties of prodrugs. Such prodrugs of the compounds of Formula I or II disclosed herein fall within this scope. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, and/or pharmacodynamic half-life, etc. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Prodrugs are described in The Organic Chemistry of Drug Design and Drug Action, by Richard B. Silverman, Academic Press, San Diego, 1992. Chapter 8: "Prodrugs and Drug delivery Systems" pp. 352-401; Design of Prodrugs, edited by H. Bundgaard, Elsevier Science, Amsterdam, 1985; Design of Biopharmaceutical Properties through Prodrugs and Analogs, Ed. by E. B. Roche, American Pharmaceutical Association, Washington, 1977; and Drug Delivery Systems, ed. by R. L. Juliano, Oxford Univ. Press, Oxford, 1980, all of which are incorporated herein by reference.

a. Compounds

Some embodiments relate to a compound of the following Formula I:

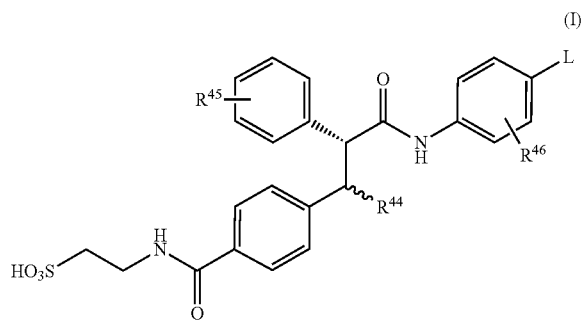

wherein $R^{44}$ is H, $CH_3$, or $CH_3CH_2$;

$R^{45}$ is $C_{1-6}$-alkyl, alkenyl, alkoxy, $C_{3-6}$-cycloalkyl, $C_{4-8}$-cycloalkenyl, $C_{4-8}$-bicycloalkenyl, aryl, or heteroaryl, any of which can be optionally substituted with one or more substituents selected from $C_{1-6}$alkyl, $CF_3$, F, CN, or $OCF_3$;

L is phenyl, indenyl, benzoxazol-2-yl, $C_{3-6}$-cycloalkyl, $C_{4-8}$-cycloalkenyl, or $C_{4-8}$-bicycloalkenyl, any of which can be optionally substituted with one or more substituents selected from F, Cl, $CH_3$, $CF_3$, $OCF_3$, or CN; and $R^{46}$ represents one or more substituents selected from H, F, Cl, $CH_3$, $CF_3$, $OCF_3$, or CN;

or a pharmaceutically acceptable salt, solvate, or prodrug thereof.

The terms "alkyl," "alkenyl," "alkoxy," "cycloalkyl," "cylcoalkenyl," "bicycloalkenyl," "aryl," "heteroaryl," "phenyl," "indenyl," and "optionally substituted" are defined in U.S. Pat. No. 10,076,504, which is incorporated herein by reference in its entirety.

Some embodiments relate to compounds of the following Formula II:

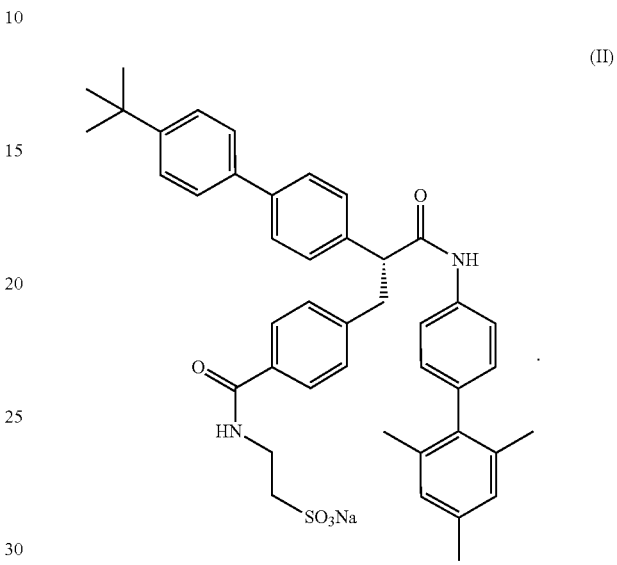

Some embodiments relate to Compound 1 which is depicted as Formula III below:

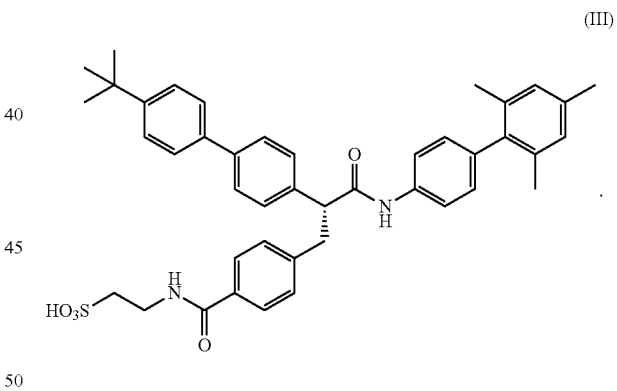

In some embodiments, the compound of Formula I, II, or III comprise a single enantiomer. Some embodiments relate to a particular polymorph or crystal structure of a compound of Formula I, II, or III, or a pharmaceutically acceptable salt, solvate, or prodrug thereof. Some embodiments relate to Form A of the compound Sodium (R)-2-(4-(2-(4'-(tert-butyl)-[1,1'-biphenyl]-4-yl)-3-oxo-3-((2',4',6'-trimethyl-[1,1'-biphenyl]-4-yl)amino)propyl)benzamido)ethane-1-sulfonate which is characterized by the XRPD pattern of FIG. 1.

In certain embodiments, a single enantiomer is >70%, >80%, >85%, >90%, >91%, >92%, >93%, >94%, >95%, >96%, >97%, >98% or >99% as compared to the total percentage of all other enantiomers of the same compound or other diastereomers present in the composition.

Another aspect provides for salts, including pharmaceutically acceptable salts, of compounds of Formula I, II, or III and pharmaceutical compositions comprising a pharmaceutically acceptable salt of compounds of Formula I, II, or III. Salts of compounds of Formula I, II, III include an inorganic base addition salt such as for example, sodium, potassium, lithium, calcium, magnesium, ammonium, aluminum salts or organic base addition salts. In one embodiment, the organic base includes, but is not limited to, dibenzylamine, imidazole, 1-(2-hydroxyethyl)pyrrolidine, ethylenediamine, diethylamine, diethanolamine, benzylamine, ethanolamine, methylamine, piperazine, tris(hydroxymethyl)aminomethane, dimethylethanolamine, lysine, arginine, taurine, choline, N-methyl-D-glucamine, betaine, benethamine, diphenyl-1-prolinol, lithium, N-methyl ephedrine, (s) alpha methylbenzylamine, or S-(+)-prolinol.

In one embodiment, the molar ratio of cationic ion to anionic ion of the salts of compounds of Formula I, II, or III is about 0 to about 10, about 0.1 to about 9, about 0.2 to about 8, about 0.3 to about 7, about 0.4 to about 6, about 0.5 to about 5, about 0.6 to about 4, about 0.7 to about 3, about 0.8 to about 2, and about 0.9 to about 1. In another embodiment, the molar ratio of cationic ion to anionic ion of the salts of compounds of Formula I, II, or III is about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, and about 10.

Another aspect provides for anhydrates, hydrates and solvates of compounds of Formula I, II, or III and pharmaceutical compositions comprising a pharmaceutically acceptable anhydrate, hydrate or solvate of compounds of Formula I, II, or III. Included are an anhydrate, hydrate or solvate of a free form or salt of a compound of Formula I, II, or III. Hydrates include, for example, a hemihydrate, monohydrate, dihydrate, trihydrate, quadrahydrate, pentahydrate, and sesquihydrate.

Also, the activities of the compounds of Formula I, II, or III can be described in terms of the concentrations of compounds required for displacement of 50% of the radiolabeled glucagon from the human glucagon receptor (the $IC_{50}$ values) according to the methods of, for example, Example A of U.S. Pat. No. 9,701,626. In one embodiment, the $IC_{50}$ values for the compounds of Formula I, II, or III are less than <10,000 nM, 9,000 nM, 8,000 nM, 7,000 nM, 6,000 nM, 5,000 nM, 4,000 nM, 3,000 nM, 2,000 nM, 1,000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 25 nM, 20 nM, 15 nM, 10 nM, or 5 nM.

In another alternative, the activities of the compounds of Formula I, II, or III can be described in terms of the concentrations of compounds required for functional antagonism of glucagon in hepatocytes from various species. In one embodiment, the $EC_{50}$ values for the compounds of Formula I, II, or III are less than <10,000 nM, 9,000 nM, 8,000 nM, 7,000 nM, 6,000 nM, 5,000 nM, 4,000 nM, 3,000 nM, 2,000 nM, 1,000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 25 nM, 20 nM, 15 nM, 10 nM, or 5 nM.

The compounds of Formula I, II, or III disclosed herein also exhibit the ability to reduce blood glucose in an animal. In certain aspects, circulating blood glucose in fasting or non-fasting (freely-feeding) animals can be reduced between 10% and 100%. A reduction of 100% refers to complete normalization of blood glucose levels, not 0% blood glucose levels. Normal blood glucose in rats, for example, is approximately 80 mg/dl (fasted) and approximately 120 mg/dl (fed). Thus, contemplated herein is a method for reducing excessive circulating blood glucose levels in fasting or freely fed animals (e.g. rat), by administering, for example, 10 mg/kg of a compound of Formula I, II, or III, by at least 10%, 20%, 30%, 40%, 50%, 60%, 70%, 80%, 90%, 95%, 99% or 100%.

b. Solid State Forms

The present disclosure also relates to solid state forms of Compound 1 or salts thereof. As with all pharmaceutical compounds and compositions, the chemical and physical properties of Compound 1 or salts thereof are important in its commercial development. These properties include, but are not limited to: (1) packing properties such as molar volume, bulk density and hygroscopicity, (2) thermodynamic properties such as melting temperature, vapor pressure and solubility, (3) kinetic properties such as dissolution rate and stability (including stability at ambient conditions, especially to moisture and under storage conditions), (4) surface properties such as surface area, wettability, interfacial tension and shape, (5) mechanical properties such as hardness, tensile strength, compactibility, handling, flow and blend; and (6) filtration properties. These properties can affect, for example, the processing and storage of the compound and pharmaceutical compositions comprising the compound.

Solid state forms of Compound 1 that improve upon one or more of these properties relative to other solid state forms of the compound are desirable. Isolating pharmaceutically acceptable solid state forms of the compound that can be manufactured and formulated on a commercial-scale has been a challenge.

A. Amorphous Free Acid of Compound 1

Figure 16:
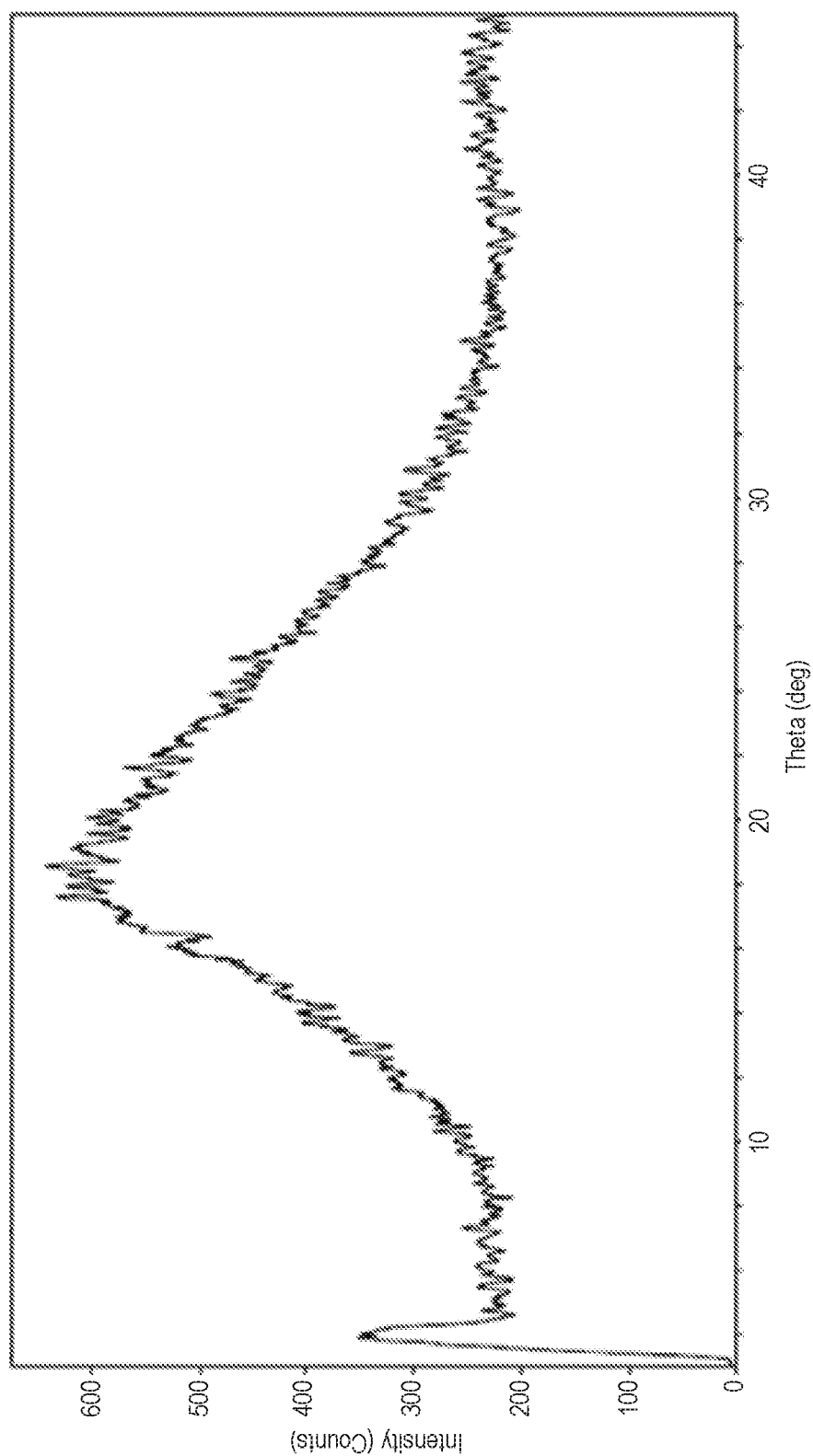
FIG. 16 is an XRPD pattern for Compound 1.

In one embodiment, the solid state form of free acid of Compound 1 is amorphous. In another embodiment, the amorphous free acid of Compound 1 is characterized as having XRPD pattern substantially as shown in FIG. 16.

In one embodiment, the amorphous free acid is prepared by reaction of a salt of Compound 1 with an acid in a solvent. In one embodiment, the salt of Compound 1 is selected from the group consisting of sodium salt, potassium salt, and calcium salt. In one embodiment, the salt is sodium salt. In another embodiment, the acid used in the reaction is hydrochloric acid. In one embodiment, the solvent is, but is not limited to, water, alcohol, or a mixture thereof. In one embodiment, the solvent is aqueous methanol, ethanol, or isopropanol.

B. Amorphous Sodium Salt of Compound 1

Figure 17:
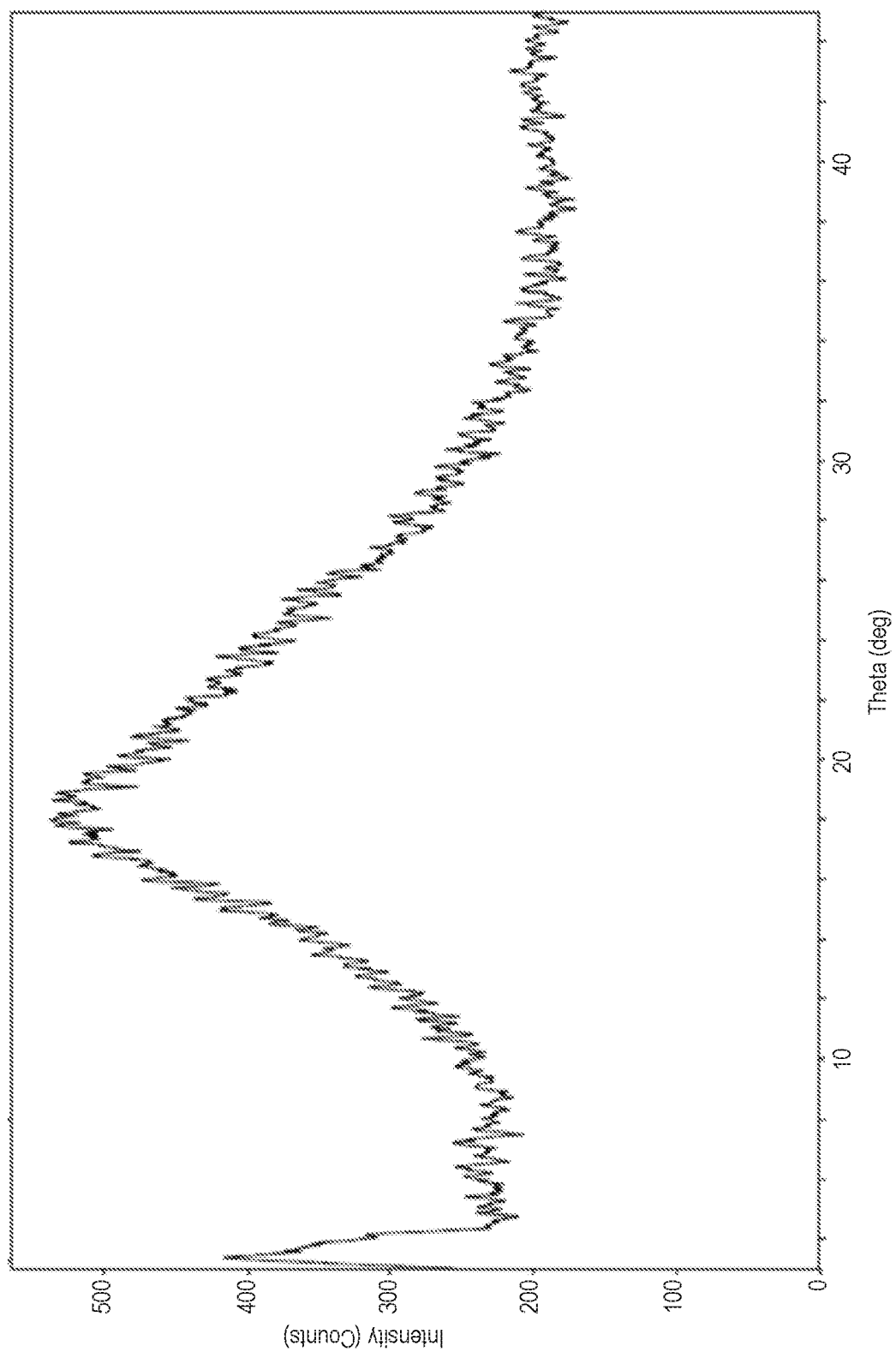
FIG. 17 is an XRPD pattern for an Amorphous Form of Sodium Salt of Compound 1.

In one embodiment, provided herein is an amorphous sodium salt of compound 1. In another embodiment, the amorphous sodium salt of Compound 1 is characterized as having XRPD pattern substantially as shown in FIG. 17.

In one embodiment, the amorphous sodium salt of compound 1 is prepared by reaction of a free acid of Compound 1 with a basic sodium material in a solvent. In one embodiment, the basic sodium material is, but not limited to, sodium methoxide, sodium acetate, sodium hydroxide, sodium bicarbonate, or sodium carbonate. In another embodiment, the solvent is ethanol or ethyl acetate.

C. Polymorph Form A

In another aspect, provided herein is a crystalline polymorph of sodium salt of Compound 1 (Form A). In one embodiment, the Polymorph Form A is a solvate. In another embodiment, the Polymorph Form A is an ethanol solvate. In another embodiment, the Polymorph Form A is a hydrate.

In one embodiment, crystalline polymorph Form A is characterized by one or more peaks in an XRPD pattern, wherein the one or more peaks is selected from the group consisting of a peak from about 4.2 to about 4.8 degrees, a peak from about 6.7 to about 7.1 degrees, a peak from about 9.0 to about 9.4 degrees, a peak from about 10.8 to about 11.2 degrees, a peak from about 11.1 to about 11.5 degrees, a peak from about 11.7 to about 12.1 degrees, a peak from about 13.5 to about 13.9 degrees, a peak from about 21.2 to about 21.6 degrees, and a peak from about 23.6 to about 24.0 degrees.

In one embodiment, crystalline polymorph Form A is characterized by one or more peaks in an XRPD pattern, wherein the one or more peaks is selected from the group consisting of a peak at about 4.7 degrees, a peak at about 7.0 degrees, a peak at about 9.3 degrees, a peak at about 11.0 degrees, a peak at about 11.4 degrees, a peak at about 11.9 degrees, a peak at about 13.8 degrees, a peak at about 21.4 degrees, and a peak at about 23.8 degrees.

A skilled artisan would understand that any particular peak of one or more peaks of the XRPD pattern may appear as a singlet, doublet, or multiplet, and/or may appear in a symmetric shape or in an asymmetric shape, depending on the type of instrument or the settings, the sensitivity of the instrument, measuring conditions, and/or purity of the crystalline form. For example, the peak at about 7.0 degrees may appear as a singlet, a doublet, or a singlet with a shoulder.

In one embodiment, crystalline polymorph Form A is characterized by a peak at about 4.7 degrees, a peak at about 7.0 degrees, a peak at about 9.3 degrees, a peak at about 11.0 degrees, a peak at about 11.4 degrees, a peak at about 11.9 degrees, a peak at about 13.8 degrees, a peak at about 21.4 degrees, and a peak at about 23.8 degrees in an XRPD pattern.

In one embodiment, crystalline polymorph Form A has an XRPD pattern characterized by peaks at 4.7±0.2, 7.0±0.2, and 11.9±0.2 degrees two theta when measured at room temperature with Cu Kα1 radiation.

In one embodiment, crystalline polymorph Form A has an XRPD pattern characterized by peaks at 4.7±0.2, 7.0±0.2, and 11.9±0.2 degrees two theta, and that is further characterized by a peak at one or more of 9.3±0.2, 11.0±0.2, 11.4±0.2, 13.8±0.2, 21.4±0.2, 23.8±0.2 degrees two theta when measured at room temperature with Cu Kα1 radiation.

In one embodiment, crystalline polymorph Form A has an XRPD pattern characterized by peaks at 4.7±0.2, 7.0±0.2, 11.9±0.2, and 13.8±0.2 degrees two theta when measured at room temperature with Cu Kα1 radiation.

In one embodiment, crystalline polymorph Form A has an XRPD pattern characterized by peaks at 4.7±0.2, 7.0±0.2, 11.9±0.2, and 21.4±0.2 degrees two theta when measured at room temperature with Cu Kα1 radiation.

In one embodiment, crystalline polymorph Form A has an XRPD pattern characterized by peaks at 4.7±0.2, 7.0±0.2, 11.9±0.2, and 23.8±0.2 degrees two theta when measured at room temperature with Cu Kα1 radiation.

In one embodiment, crystalline polymorph Form A has an XRPD pattern characterized by peaks at 4.7±0.2, 7.0±0.2, 11.0±0.2, 11.9±0.2, and 21.4±0.2 degrees two theta when measured at room temperature with Cu Kα1 radiation.

In one embodiment, crystalline polymorph Form A has an XRPD pattern characterized by peaks at 4.7±0.2, 7.0±0.2, 11.0±0.2, 11.9±0.2, and 23.8±0.2 degrees two theta when measured at room temperature with Cu Kα1 radiation.

In one embodiment, crystalline polymorph Form A has an XRPD pattern characterized by peaks at 4.7±0.2, 7.0±0.2, 9.3±0.2, 11.0±0.2, 11.9±0.2, and 21.4±0.2 degrees two theta when measured at room temperature with Cu Kα1 radiation.

In one embodiment, crystalline polymorph Form A has an XRPD pattern characterized by peaks at 4.7±0.2, 7.0±0.2, 9.3±0.2, 11.0±0.2, 11.9±0.2, and 23.8±0.2 degrees two theta when measured at room temperature with Cu Kα1 radiation.

In one embodiment, crystalline polymorph Form A has an XRPD pattern characterized by peaks at the positions listed in Table 1±0.2 degrees two theta when measured at room temperature with Cu Kα1 radiation.

In one embodiment, crystalline polymorph Form A has an XRPD pattern characterized by one or more peaks at the positions listed in Table A below ±0.2 degrees two theta when measured at room temperature with Cu Kα1 radiation.

TABLE A

| Peak # | 2-Theta | Relative Intensity (%) |
|---|---|---|
| 1 | 4.663 | 13.2 |
| 2 | 6.961 | 100.0 |
| 3 | 9.278 | 47.4 |
| 4 | 11.040 | 49.5 |
| 5 | 11.380 | 73.2 |
| 6 | 11.919 | 65.3 |
| 7 | 12.899 | 15.6 |
| 8 | 13.762 | 25.9 |
| 9 | 15.097 | 18.4 |
| 10 | 15.501 | 12.5 |
| 11 | 16.182 | 19.4 |
| 12 | 16.645 | 6.8 |
| 13 | 17.061 | 5.2 |
| 14 | 17.618 | 12.7 |
| 15 | 18.323 | 19.7 |
| 16 | 19.654 | 5.5 |
| 17 | 20.093 | 10.5 |
| 18 | 20.760 | 11.0 |
| 19 | 21.421 | 22.6 |
| 20 | 22.174 | 13.7 |
| 21 | 23.022 | 16.2 |
| 22 | 23.800 | 22.6 |
| 23 | 24.984 | 11.4 |
| 24 | 28.346 | 4.1 |
| 25 | 31.232 | 4.5 |
| 26 | 31.764 | 4.7 |
| 27 | 32.420 | 4.3 |
| 28 | 33.098 | 6.6 |
| 29 | 36.104 | 3.4 |
| 30 | 36.755 | 5.9 |

In one embodiment, crystalline polymorph Form A has an XRPD pattern substantially as shown in FIG. 1.

Figure 31:
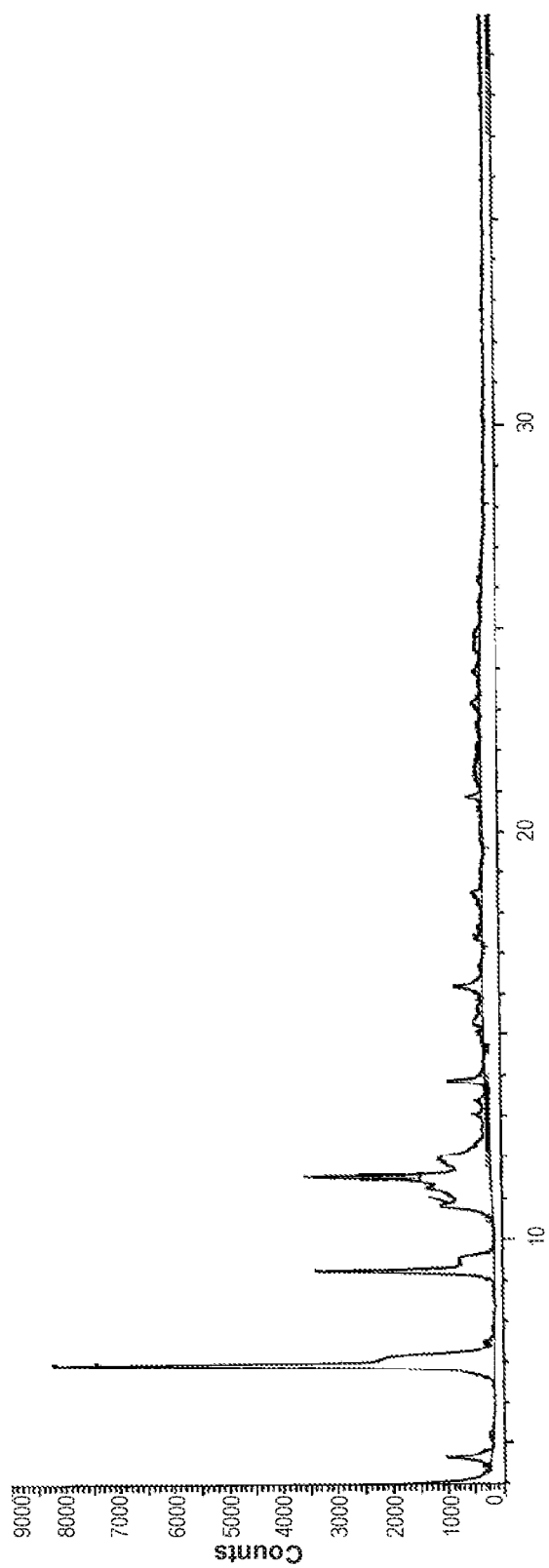
FIG. 31 shows an XRPD pattern for unmilled Polymorph Form A.

In one embodiment, unmilled crystalline polymorph Form A has an XRPD pattern substantially as shown in FIG. 31.

In one embodiment, unmilled crystalline polymorph Form A has an XRPD pattern characterized by one or more peaks at the positions listed in Table B below ±0.2 degrees two theta.

TABLE B

| Peak # | 2-Theta | Relative Intensity (%) |
|---|---|---|
| 1 | 4.630° | 9.2 |
| 2 | 5.187° | 0.7 |
| 3 | 6.928° | 100.0 |
| 4 | 6.946° | 90.5 |
| 5 | 9.233° | 40.0 |
| 6 | 9.497° | 8.4 |
| 7 | 10.889° | 9.4 |
| 8 | 11.539° | 41.7 |
| 9 | 11.947° | 11.7 |
| 10 | 13.011° | 2.3 |
| 11 | 13.325° | 1.7 |
| 12 | 13.858° | 10.2 |
| 13 | 15.186° | 0.7 |

TABLE B-continued

| Peak # | 2-Theta | Relative Intensity (%) |
| --- | --- | --- |
| 14 | 15.028° | 1.0 |
| 15 | 15.299° | 2.6 |
| 16 | 16.186° | 6.5 |
| 17 | 16.680° | 0.7 |
| 18 | 17.434° | 1.1 |
| 19 | 18.448° | 1.9 |
| 20 | 19.052° | 0.9 |
| 21 | 19.812° | 1.3 |
| 22 | 20.049° | 1.2 |
| 23 | 20.578° | 0.8 |
| 24 | 20.844° | 3.0 |
| 25 | 21.588° | 1.0 |
| 26 | 22.050° | 0.9 |
| 27 | 22.553° | 0.8 |
| 28 | 23.164° | 1.8 |
| 29 | 23.942° | 1.3 |
| 30 | 24.589° | 1.3 |
| 31 | 24.765° | 1.1 |
| 32 | 26.182° | 0.8 |

Figure 32:
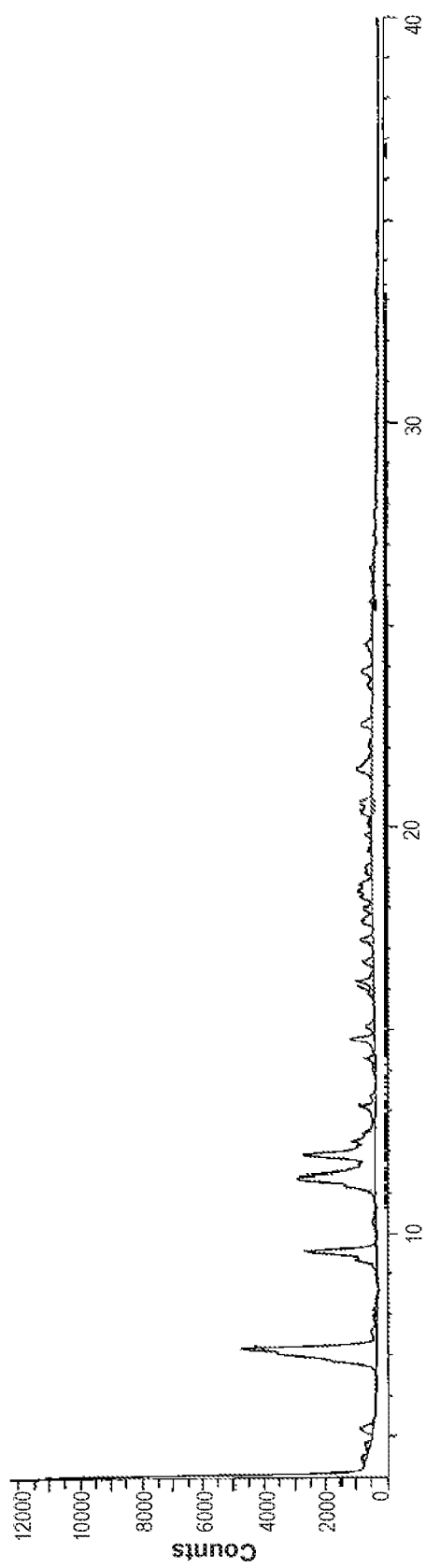
FIG. 32 shows an XRPD pattern for milled Polymorph Form A.

In one embodiment, milled crystalline polymorph Form A has an XRPD pattern substantially as shown in FIG. 32.

In one embodiment, milled crystalline polymorph Form A has an XRPD pattern characterized by one or more peaks at the positions listed in Table C below ±0.2 degrees two theta.

TABLE C

| Peak # | 2-Theta | Relative Intensity (%) |
| --- | --- | --- |
| 0 | 5.175 | 11.5 |
| 1 | 7.122 | 100.0 |
| 2 | 7.568 | 5.5 |
| 3 | 9.540 | 62.5 |
| 4 | 11.378 | 75.8 |
| 5 | 11.921 | 66.0 |
| 6 | 13.082 | 11.7 |
| 7 | 14.268 | 7.3 |
| 8 | 14.765 | 21.6 |
| 9 | 15.091 | 8.9 |
| 10 | 15.960 | 5.5 |
| 11 | 16.192 | 14.6 |
| 12 | 16.679 | 9.1 |
| 13 | 17.214 | 13.2 |
| 14 | 17.700 | 9.5 |
| 15 | 17.971 | 9.0 |
| 16 | 18.406 | 13.5 |
| 17 | 20.445 | 9.6 |
| 18 | 20.572 | 9.7 |
| 19 | 21.493 | 14.2 |
| 20 | 22.587 | 11.8 |
| 21 | 23.879 | 10.5 |
| 22 | 24.544 | 6.1 |

Figure 30:
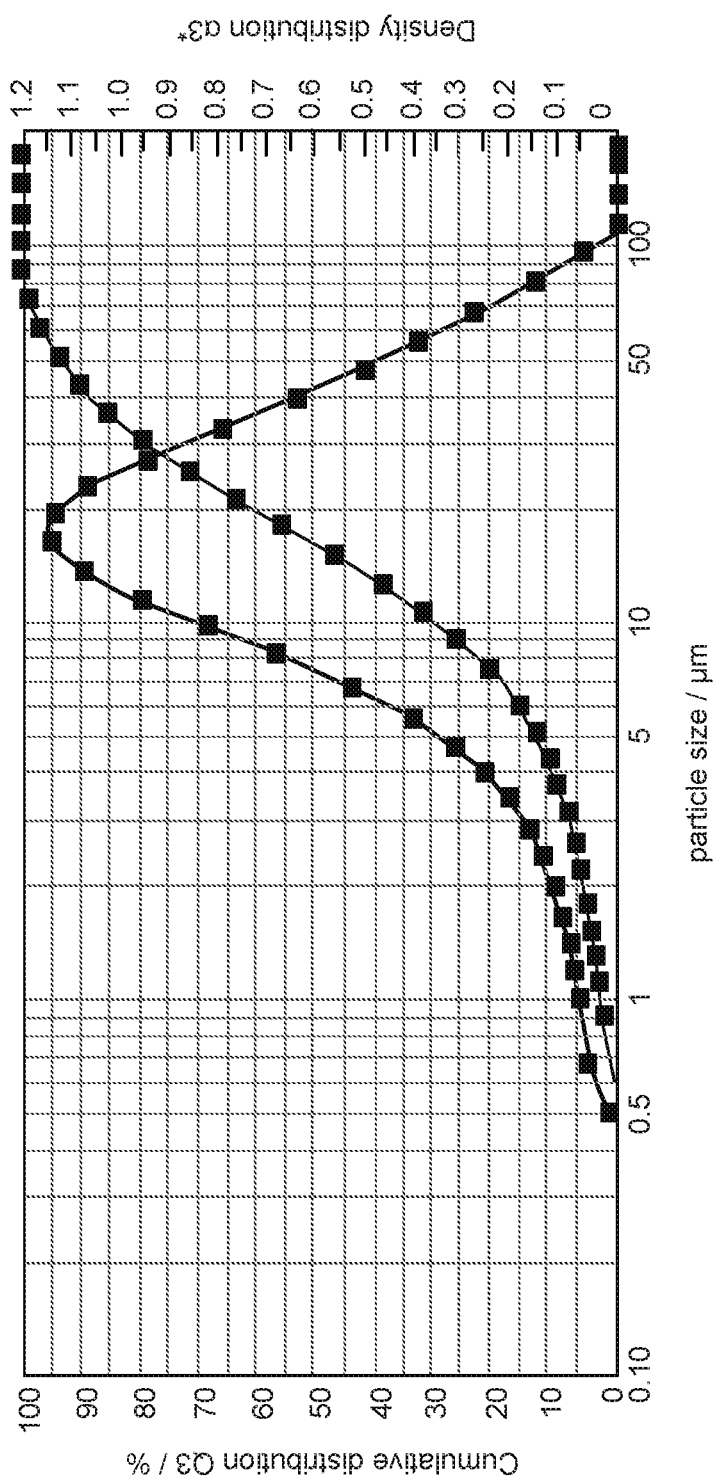
FIG. 30 shows a chart of particle size distribution for Polymorph Form A.

In one embodiment, the particle size of crystalline polymorph Form A is analyzed by a laser diffraction analyzer. The measurement provides the values $D_{10}$, $D_{50}$ and $D_{90}$ representing the measurement below which 10%, 50% and 90% of the particles of the product on which the measurement was taken are found, respectively. In one embodiment, the $D_{10}$ is about 4 μm to about 5 μm; the $D_{50}$ is about 15 μm to about 18 μm; the $D_{90}$ is about 40 μm to about 50 μm. In one embodiment, crystalline polymorph Form A is characterized by at least one of a $D_{10}$ of about 4.39 μm, a $D_{50}$ of about 16.10 μm and a $D_{90}$ of about 43.18 μm. In one embodiment, crystalline polymorph Form A is characterized by at least one of a $D_5$ of about 2.46 μm, $D_{10}$ of about 4.39 μm, $D_{15}$ of about 6.02 μm, $D_{20}$ of about 7.49 μm, $D_{25}$ of about 8.87 μm, $D_{30}$ of about 10.24 μm, $D_{35}$ of about 11.62 μm, $D_{40}$ of about 13.03 μm, $D_{45}$ of about 14.50 μm, $D_{50}$ of about 16.10 μm, $D_{55}$ of about 17.76 μm, $D_{60}$ of about 19.70 μm, $D_{65}$ of about 21.85 μm, $D_{70}$ of about 24.34 μm, $D_{75}$ of about 27.46 μm, $D_{80}$ of about 31.16 μm, $D_{85}$ of about 35.97 μm, $D_{90}$ of about 43.18 μm, and $D_{95}$ of about 55.61 μm. In one embodiment, crystalline polymorph Form A is characterized by particle sizes displayed in FIG. 30.

In one embodiment, crystalline polymorph Form A has a thermogravimetric analysis profile showing a weight loss of about 3.3% between about 34° C. and about 133° C. when heated at a rate of 10° C./minute.

Figure 33:
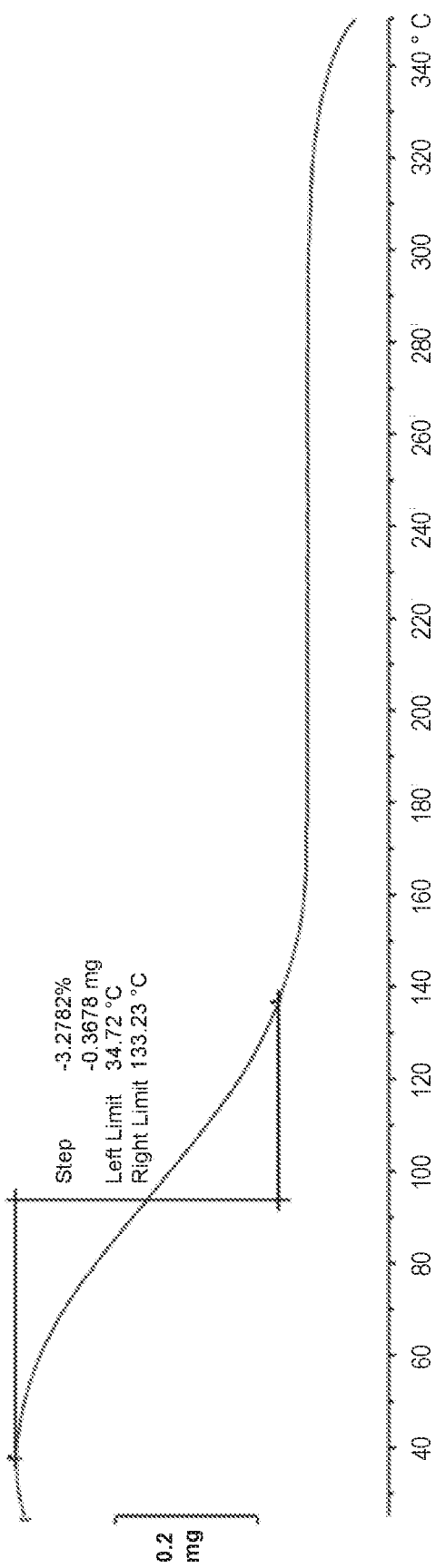
FIG. 33 shows a TGA result for Polymorph Form A.

In one embodiment, crystalline polymorph Form A has a thermogravimetric analysis profile substantially as shown in FIG. 33.

In one embodiment, crystalline polymorph Form A has a differential scanning calorimetry profile comprising a first endotherm between about 28° C. to about 92° C. when heated at a rate of 10° C./minute.

In one embodiment, crystalline polymorph Form A has a differential scanning calorimetry profile comprising a first endotherm between about 60° C. to about 80° C. when heated at a rate of 10° C./minute.

In one embodiment, crystalline polymorph Form A has a differential scanning calorimetry profile comprising a second endotherm between about 201° C. to about 210° C. when heated at a rate of 10° C./minute.

In one embodiment, crystalline polymorph Form A has a differential scanning calorimetry profile comprising a second endotherm between about 205° C. to about 208° C. when heated at a rate of 10° C./minute.

In one embodiment, crystalline polymorph Form A has a differential scanning calorimetry profile comprising a third endotherm between about 225° C. to about 237° C. when heated at a rate of 10° C./minute.

In one embodiment, crystalline polymorph Form A has a differential scanning calorimetry profile comprising a third endotherm between about 230° C. to about 235° C. when heated at a rate of 10° C./minute.

In one embodiment, crystalline polymorph Form A has a differential scanning calorimetry profile comprising a fourth endotherm between about 241° C. to about 248° C. when heated at a rate of 10° C./minute.

In one embodiment, crystalline polymorph Form A has a differential scanning calorimetry profile comprising a fourth endotherm between about 244° C. to about 246° C. when heated at a rate of 10° C./minute.

In one embodiment, crystalline polymorph Form A has a differential scanning calorimetry profile comprising a first endotherm with an onset point at about 133.8° C. and a peak point at about 138.6° C. when heated at a rate of 10° C./minute.

In one embodiment, crystalline polymorph Form A has a differential scanning calorimetry profile comprising a second endotherm with an onset point at about 206.7° C. and a peak point at about 210.7° C. when heated at a rate of 10° C./minute.

In one embodiment, crystalline polymorph Form A has a differential scanning calorimetry profile comprising a third endotherm with an onset point at about 240.1° C. and a peak point at about 246.9° C. when heated at a rate of 10° C./minute.

Figure 29:
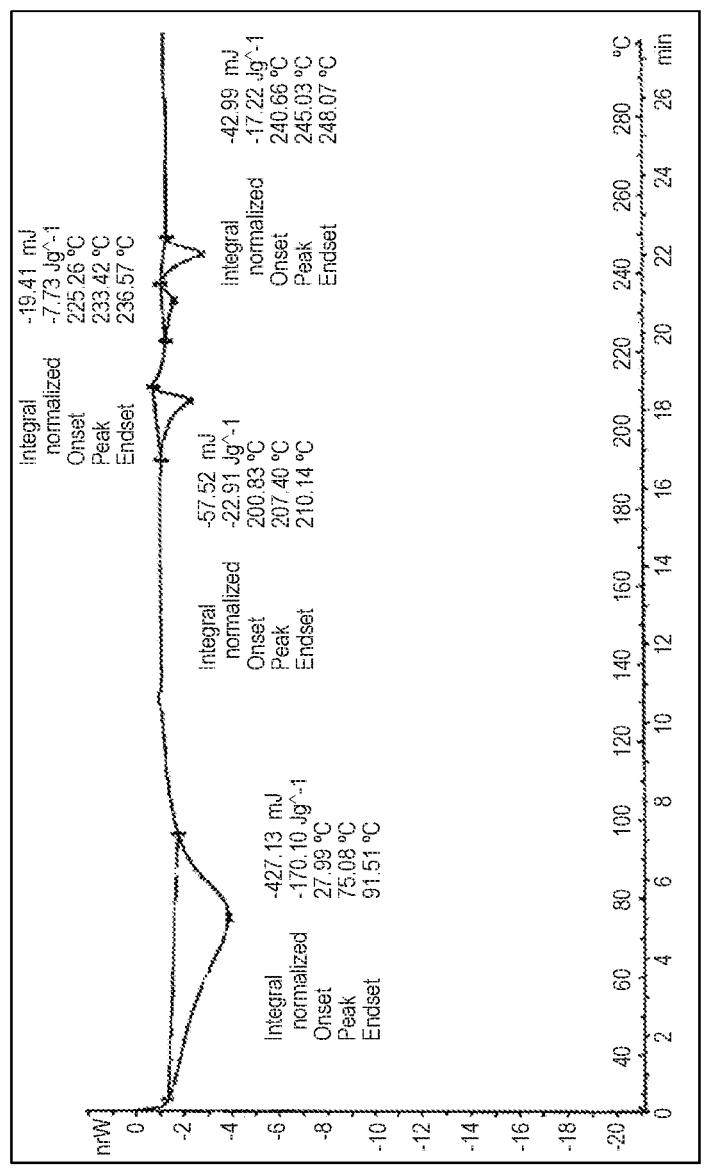
FIG. 29 shows a DSC result for Polymorph Form A.

In one embodiment, crystalline polymorph Form A has a differential scanning calorimetry profile substantially as shown in FIG. 29.

Figure 34:
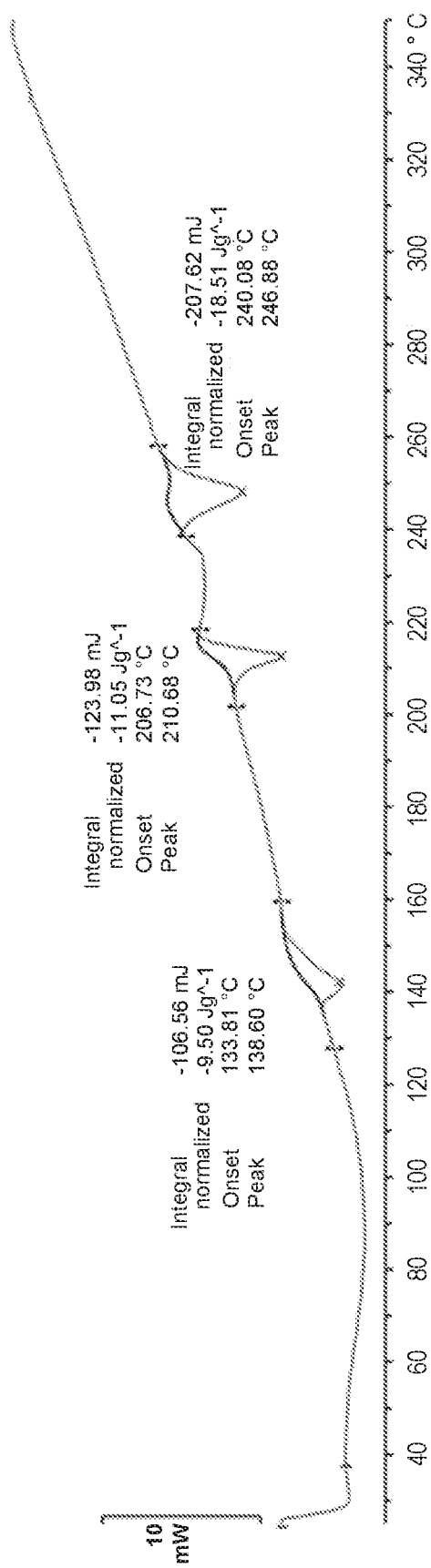
FIG. 34 shows a DSC result for milled Polymorph Form A.

In one embodiment, crystalline polymorph Form A has a differential scanning calorimetry profile substantially as shown in FIG. 34.

In one embodiment, crystalline polymorph Form A has a thermogravimetric analysis profile showing a weight loss of about 3.3% between about 34° C. and about 133° C. when heated at a rate of 10° C./minute; and a differential scanning calorimetry profile comprising a first endotherm between about 28° C. to about 92° C. when heated at a rate of 10° C./minute, a second endotherm between about 201° C. to about 210° C. when heated at a rate of 10° C./minute, a third endotherm between about 225° C. to about 237° C. when heated at a rate of 10° C./minute, and/or a fourth endotherm between about 241° C. to about 248° C. when heated at a rate of 10° C./minute. In one embodiment, the differential scanning calorimetry profile comprises a first endotherm between about 28° C. to about 92° C. when heated at a rate of 10° C./minute. In another embodiment, the differential scanning calorimetry profile comprises a second endotherm between about 201° C. to about 210° C. when heated at a rate of 10° C./minute. In another embodiment, the differential scanning calorimetry profile comprises a third endotherm between about 225° C. to about 237° C. when heated at a rate of 10° C./minute. In another embodiment, the differential scanning calorimetry profile comprises a fourth endotherm between about 241° C. to about 248° C. when heated at a rate of 10° C./minute.

In one embodiment, crystalline polymorph Form A has a thermogravimetric analysis profile showing a weight loss of about 3.3% between about 34° C. and about 133° C. when heated at a rate of 10° C./minute; and a differential scanning calorimetry profile comprising a first endotherm between about 60° C. to about 80° C. when heated at a rate of 10° C./minute, a second endotherm between about 205° C. to about 208° C. when heated at a rate of 10° C./minute, a third endotherm between about 230° C. to about 235° C. when heated at a rate of 10° C./minute, and/or a fourth endotherm between about 244° C. to about 246° C. when heated at a rate of 10° C./minute. In one embodiment, the differential scanning calorimetry profile comprises a first endotherm between about 60° C. to about 80° C. when heated at a rate of 10° C./minute. In another embodiment, the differential scanning calorimetry profile comprises a second endotherm between about 205° C. to about 208° C. when heated at a rate of 10° C./minute. In another embodiment, the differential scanning calorimetry profile comprises a third endotherm between about 230° C. to about 235° C. when heated at a rate of 10° C./minute. In another embodiment, the differential scanning calorimetry profile comprises a fourth endotherm between about 244° C. to about 246° C. when heated at a rate of 10° C./minute.

In one embodiment, crystalline polymorph Form A has a thermogravimetric analysis profile showing a weight loss of about 3.3% between about 34° C. and about 133° C. when heated at a rate of 10° C./minute; and a differential scanning calorimetry profile comprising a first endotherm between about 60° C. to about 80° C. when heated at a rate of 10° C./minute, a second endotherm between about 205° C. to about 208° C. when heated at a rate of 10° C./minute, a third endotherm between about 230° C. to about 235° C. when heated at a rate of 10° C./minute, and/or a fourth endotherm between about 244° C. to about 246° C. when heated at a rate of 10° C./minute. In one embodiment, the differential scanning calorimetry profile comprises a first endotherm between about 60° C. to about 80° C. when heated at a rate of 10° C./minute. In another embodiment, the differential scanning calorimetry profile comprises a second endotherm between about 205° C. to about 208° C. when heated at a rate of 10° C./minute. In another embodiment, the differential scanning calorimetry profile comprises a third endotherm between about 230° C. to about 235° C. when heated at a rate of 10° C./minute. In another embodiment, the differential scanning calorimetry profile comprises a fourth endotherm between about 244° C. to about 246° C. when heated at a rate of 10° C./minute.

In one embodiment, crystalline polymorph Form A has a thermogravimetric analysis profile showing a weight loss of about 3.3% between about 34° C. and about 133° C. when heated at a rate of 10° C./minute; and a differential scanning calorimetry profile comprising a first endotherm with an onset point at about 133.8° C. and a peak point at about 138.6° C. when heated at a rate of 10° C./minute; a second endotherm with an onset point at about 206.7° C. and a peak point at about 210.7° C. when heated at a rate of 10° C./minute; and/or a third endotherm with an onset point at about 240.1° C. and a peak point at about 246.9° C. when heated at a rate of 10° C./minute.

In one embodiment, crystalline polymorph Form A has an X-ray diffraction pattern as previously described above, and further has at least one of the following: (a) a thermogravimetric analysis profile showing a weight loss of about 3.3% between about 34° C. and about 133° C. when heated at a rate of 10° C./minute; and (b) a differential scanning calorimetry profile comprising a first endotherm with an onset point at about 133.8° C. and a peak point at about 138.6° C. when heated at a rate of 10° C./minute, a second endotherm with an onset point at about 206.7° C. and a peak point at about 210.7° C. when heated at a rate of 10° C./minute, and/or a third endotherm with an onset point at about 240.1° C. and a peak point at about 246.9° C. when heated at a rate of 10° C./minute.

In one embodiment, crystalline polymorph Form A has an X-ray diffraction pattern as previously described above, and further has a thermogravimetric analysis profile showing a weight loss of about 3.3% between about 34° C. and about 133° C. when heated at a rate of 10° C./minute.

In one embodiment, crystalline polymorph Form A has an X-ray diffraction pattern as previously described above, and further has a differential scanning calorimetry profile comprising a first endotherm between about 28° C. to about 92° C. when heated at a rate of 10° C./minute, a second endotherm between about 201° C. to about 210° C. when heated at a rate of 10° C./minute, a third endotherm between about 225° C. to about 237° C. when heated at a rate of 10° C./minute, and/or a fourth endotherm between about 241° C. to about 248° C. when heated at a rate of 10° C./minute.

In one embodiment, crystalline polymorph Form A has an X-ray diffraction pattern as previously described above; a thermogravimetric analysis profile showing a weight loss of about 3.3% between about 34° C. and about 133° C. when heated at a rate of 10° C./minute; and/or a differential scanning calorimetry profile comprising a first endotherm between about 28° C. to about 92° C. when heated at a rate of 10° C./minute, a second endotherm between about 201° C. to about 210° C. when heated at a rate of 10° C./minute, a third endotherm between about 225° C. to about 237° C. when heated at a rate of 10° C./minute, and/or a fourth endotherm between about 241° C. to about 248° C. when heated at a rate of 10° C./minute.

In one embodiment, crystalline polymorph Form A has an X-ray diffraction pattern as previously described above; and/or a differential scanning calorimetry profile substantially as shown in FIG. 29.

In one embodiment, crystalline polymorph Form A has an X-ray diffraction pattern as previously described above; a thermogravimetric analysis profile substantially as shown in FIG. 33; and/or a differential scanning calorimetry profile substantially as shown in FIG. 34.

In one embodiment, crystalline polymorph Form A is characterized by a melting point.

In one aspect, provided herein are methods for preparing the crystalline polymorph Form A. In one embodiment, the method comprises combining sodium salt of compound 1 in a first solvent to create a first mixture; heating the first mixture to a temperature greater than room temperature for from about 10 minutes to 2 hours; filtering the first mixture; adding a solution of NaOH or NaHCO₃ in ethanol/water to the first mixture to create a second mixture; cooling said mixture; and isolating crystalline polymorph Form A from the second mixture. In one embodiment, the sodium salt of Compound 1 is amorphous. In one embodiment, the first solvent comprises ethanol, ethyl acetate, and water. In another embodiment, the first solvent comprises ethanol and water. In a preferred embodiment, the first solvent comprises ethanol, ethyl acetate, and water in a mass ratio of about 364:9:8, respectively. In another embodiment, the temperature is about 50° C. to about 80° C.

In one embodiment, the purity of crystalline polymorph Form A achieved by the method described here is greater than 90% (HPLC purity). In another embodiment, the purity of crystalline polymorph Form A achieved by the method described here is greater than 91%, 92%, 93%, 94%, 95%, 96%, 97%, 98%, 99%, or 99.5% (HPLC purity).

In one embodiment, the detected amount of impurity A is below 0.1%, 0.09% or 0.08%. In another embodiment, the detected amount of impurity B is below 0.2%, 0.15%, or 0.12%. In yet another embodiment, the detected amount of impurity C is below 0.1%, 0.08%, or 0.05%. In some embodiments, one or more of impurity A, B, or C are co-detected. Impurity A has a retention time at 6.2 min in the HPLC described in Example 6 and Table 6. Impurity B is a compound depicted below.

(Impurity B)

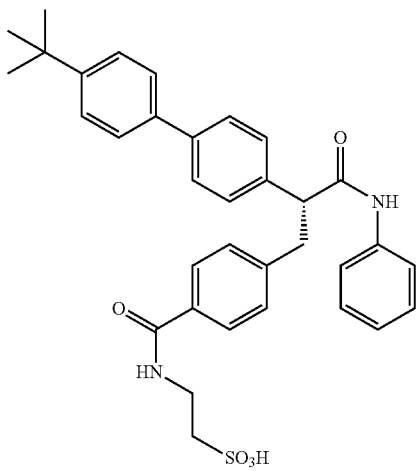

Impurity C is a compound depicted below.

(Impurity C)

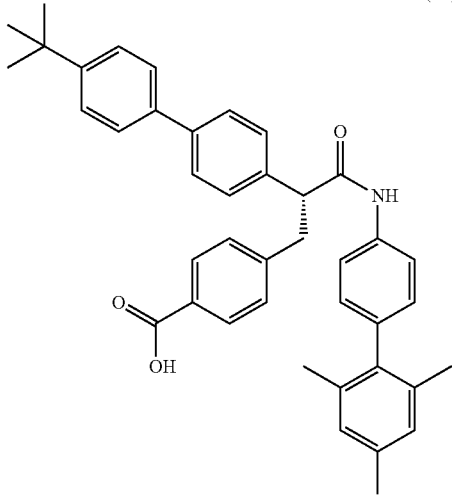

D. Polymorph Form B

In another aspect, provided herein is a crystalline polymorph of calcium salt of Compound 1 (Form B).

Figure 19:
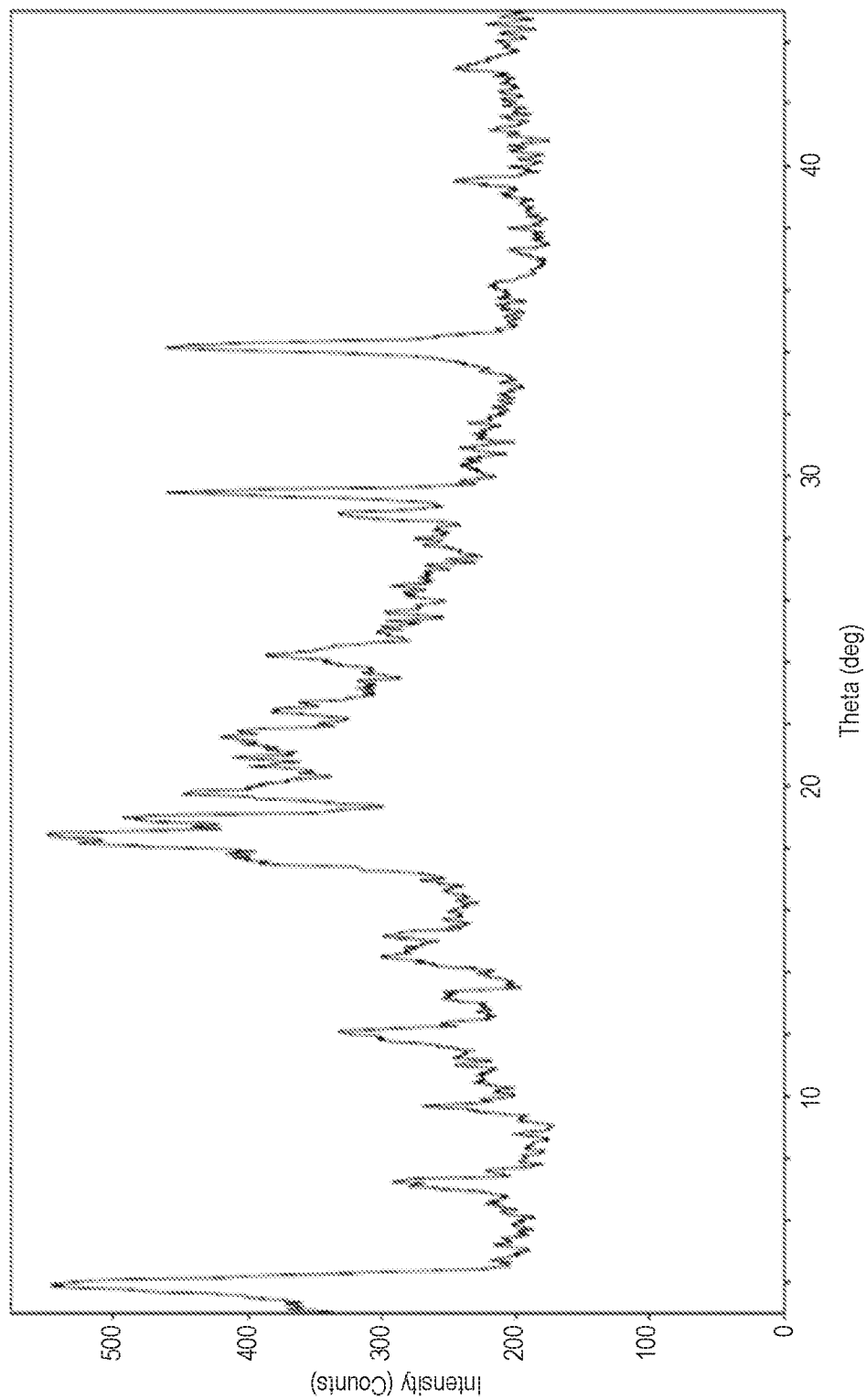
FIG. 19 is an XRPD of Polymorph Form B.

In one embodiment, crystalline polymorph Form B has an XRPD pattern substantially as shown in FIG. 19.

In one embodiment, crystalline polymorph Form B has a thermogravimetric analysis profile showing a first weight loss of about 3% to about 4% between about 110° C. and about 127° C., a second weight loss of about 4% to about 6% between about 275° C. and about 310° C., and/or a third weight loss of about 49% to about 51% between about 330° C. and about 500° C. when heated at a rate of 20° C./minute. In another embodiment, crystalline polymorph Form B has a thermogravimetric analysis profile showing a first weight loss of about 3.2% between about 110° C. and about 127° C., a second weight loss of about 5.2% between about 275° C. and about 310° C., and a third weight loss about 50.4% between about 330° C. and about 500° C. when heated at a rate of 20° C./minute.

Figure 21:
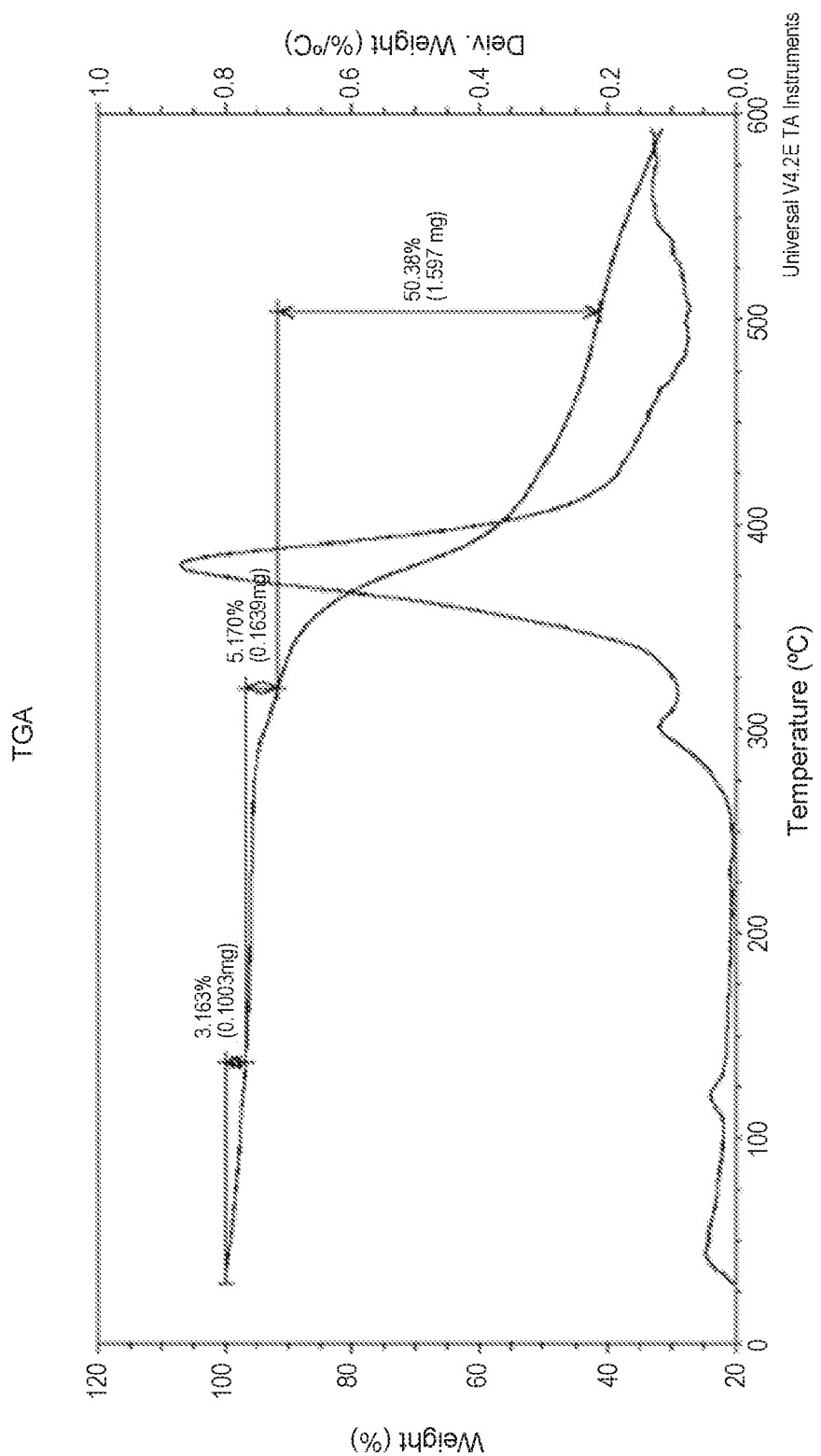
FIG. 21 is a Thermal Gravimetric Analysis ("TGA") Result of Polymorph Form B.

In one embodiment, crystalline polymorph Form B has a thermogravimetric analysis profile substantially as shown in FIG. 21.

In one embodiment, crystalline polymorph Form B has a differential scanning calorimetry profile comprising a first endotherm with an onset point at about 241° C. with a peak point at 244° C.

Figure 20:
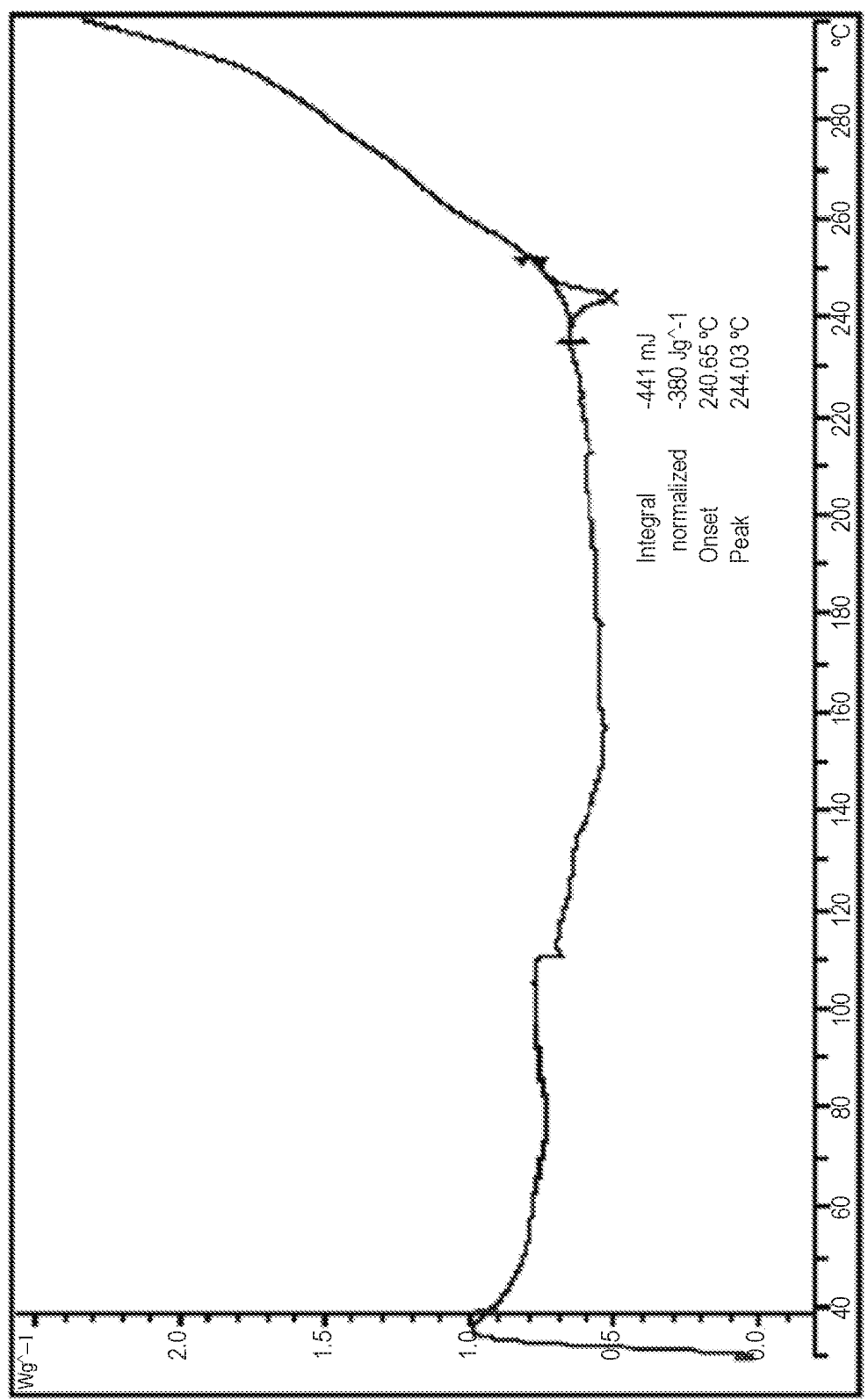
FIG. 20 is a Differential Scanning calorimetry ("DSC") Result for Polymorph Form B.

In one embodiment, crystalline polymorph Form B has a differential scanning calorimetry profile substantially as shown in FIG. 20.

In one embodiment, crystalline polymorph Form B has an X-ray diffraction pattern as previously described above, and further has at least one of the following: (a) a thermogravimetric analysis profile showing a first weight loss of about 3% to about 4% between about 110° C. and about 127° C., a second weight loss of about 4% to about 6% between about 275° C. and about 310° C., and/or a third weight loss of about 49% to about 51% between about 330° C. and about 500° C. when heated at a rate of 20° C./minute; and (b) a differential scanning calorimetry profile comprising a first endotherm with an onset point at about 241° C. and with a peak at 244° C.

In one embodiment, crystalline polymorph Form B has an X-ray diffraction pattern as previously described above, and further has at least one of the following: (a) a thermogravimetric analysis profile substantially as shown in FIG. 21; and (b) a differential scanning calorimetry profile substantially as shown in FIG. 20.

In one embodiment, crystalline polymorph Form B is characterized by a melting point.

In one aspect, provided herein are methods for preparing the crystalline polymorph Form B. In one embodiment, the method comprises combining Compound 1 with a calcium basic material in a solvent; stirring the mixture at a temperature higher than room temperature for about 30 minutes, about 1 hour, or about 2 hours; then at room temperature for about 1 hour, about 2 hours, or about 3 hours; filtering the solid and drying to give crystalline polymorph Form B. In one embodiment, the solvent is selected from the group consisting of methanol, 2-propanol, and ethanol. In another embodiment, the temperature is about 60° C. In another embodiment, the calcium basic material is calcium hydroxide.

In one embodiment, the method for preparing the crystalline polymorph Form B, further comprises washing the solid after the filtration with a solvent; combining the solvent; evaporating the solvent; and drying to give crystalline polymorph Form B. In one embodiment, the solvent is methanol.

E. Polymorph Form C

In another aspect, provided herein is a crystalline polymorph of potassium salt of Compound 1 (Form C).

Figure 24:
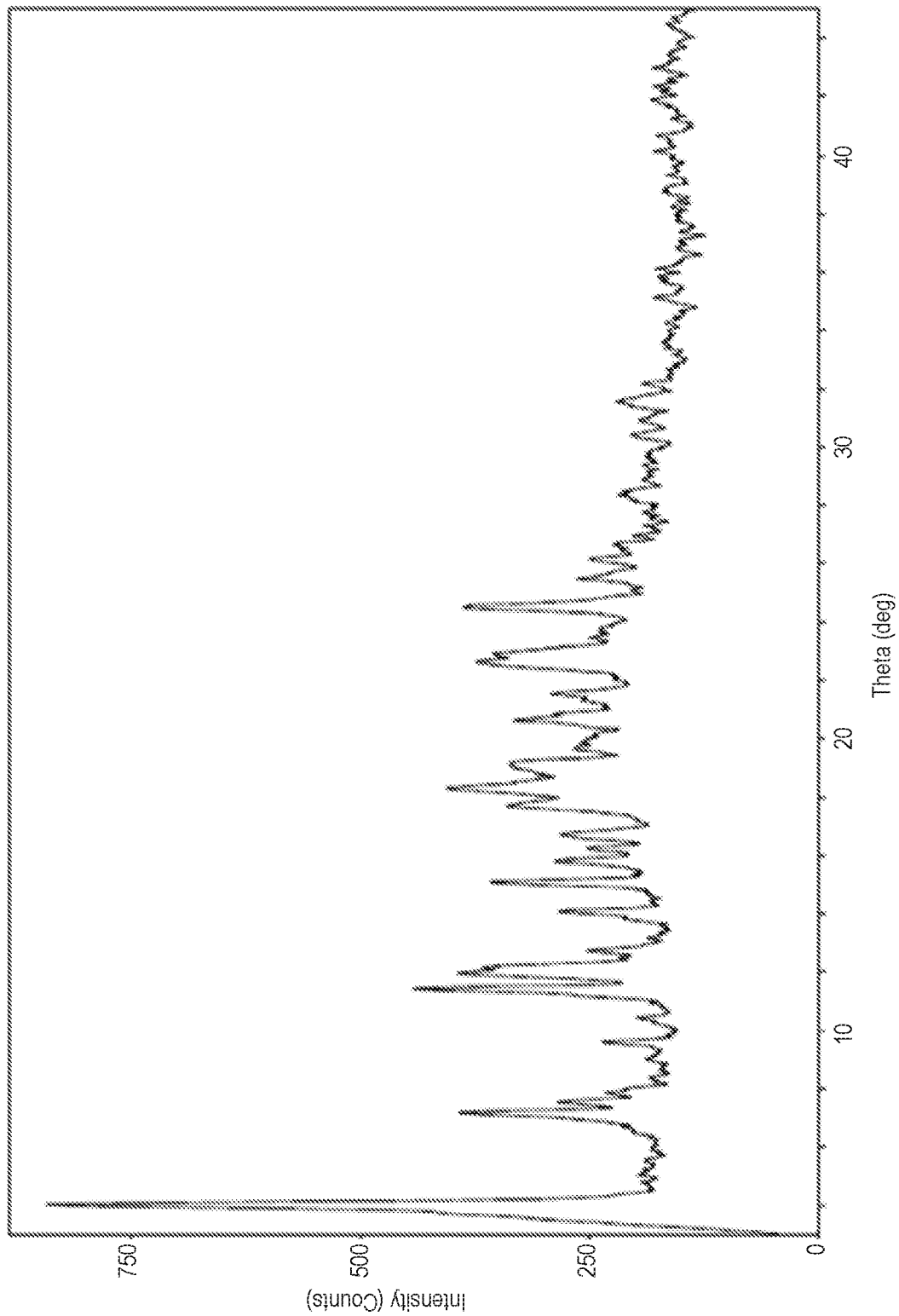
FIG. 24 shows an XRPD pattern for Polymorph Form C.

In one embodiment, crystalline polymorph Form C has an XRPD pattern substantially as shown in FIG. 24.

In one embodiment, crystalline polymorph Form C has a thermogravimetric analysis profile showing a first weight loss of about 2% to about 3% between about 70° C. and about 80° C.; a second weight loss of about 50% to about 60% between about 275° C. and about 420° C., and/or a third weight loss of about 5% to about 6% between about 460° C. and about 480° C. when heated at a rate of 20° C./minute. In another embodiment, crystalline polymorph Form C has a thermogravimetric analysis profile showing a first weight loss of about 2.2% between about 70° C. and about 80° C., a second weight loss of about 55.1% between about 275° C. and about 420° C., and/or a third weight loss of about 5.3% between about 460° C. and about 480° C. when heated at a rate of 20° C./minute.

Figure 26:
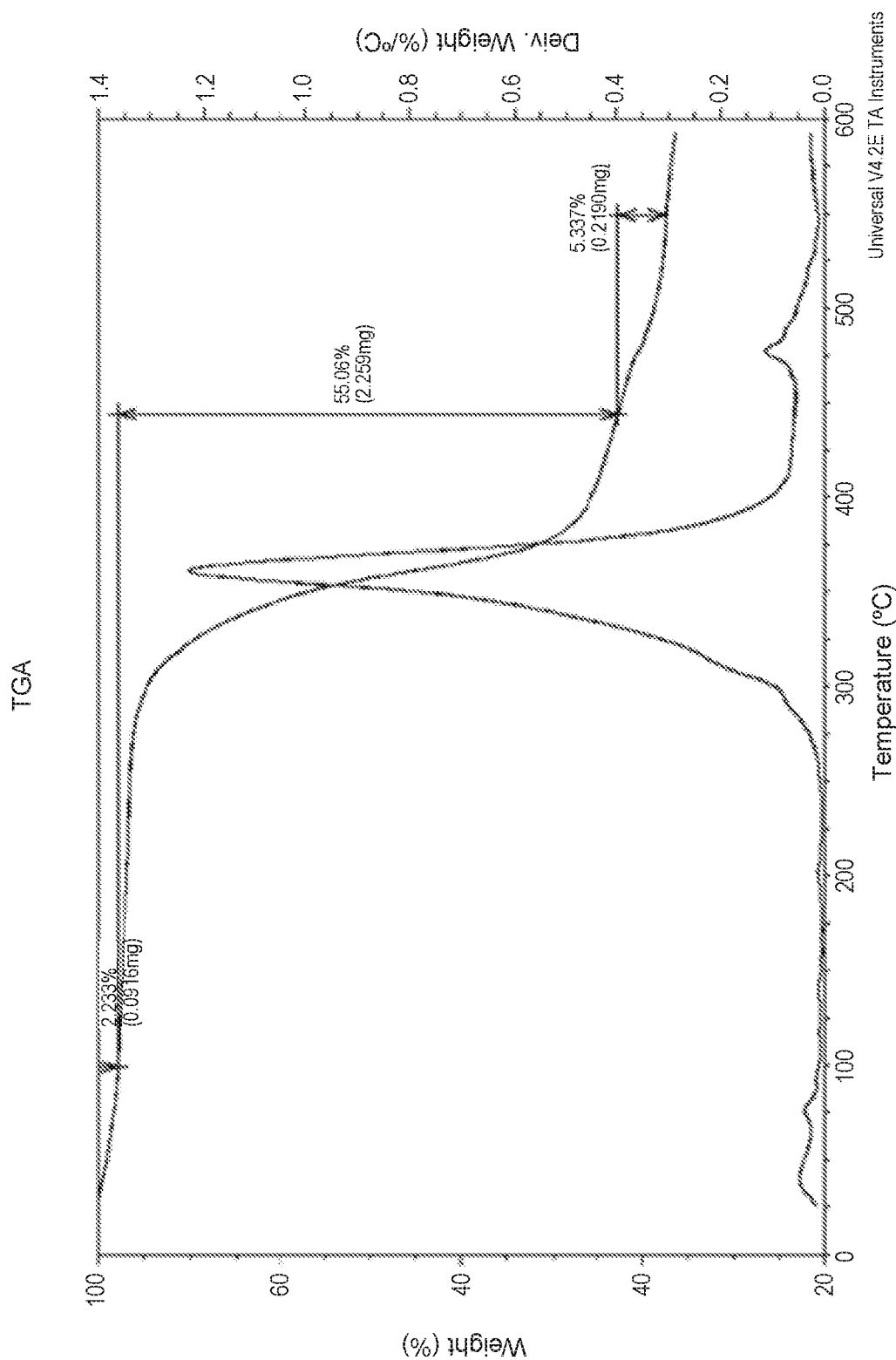
FIG. 26 shows a TGA result for Polymorph Form C.

In one embodiment, crystalline polymorph Form C has a thermogravimetric analysis profile substantially as shown in FIG. 26.

In one embodiment, crystalline polymorph Form C has a differential scanning calorimetry profile comprising a first endotherm with an onset point at about 194° C. and with a peak point at 202.5° C.

Figure 25:
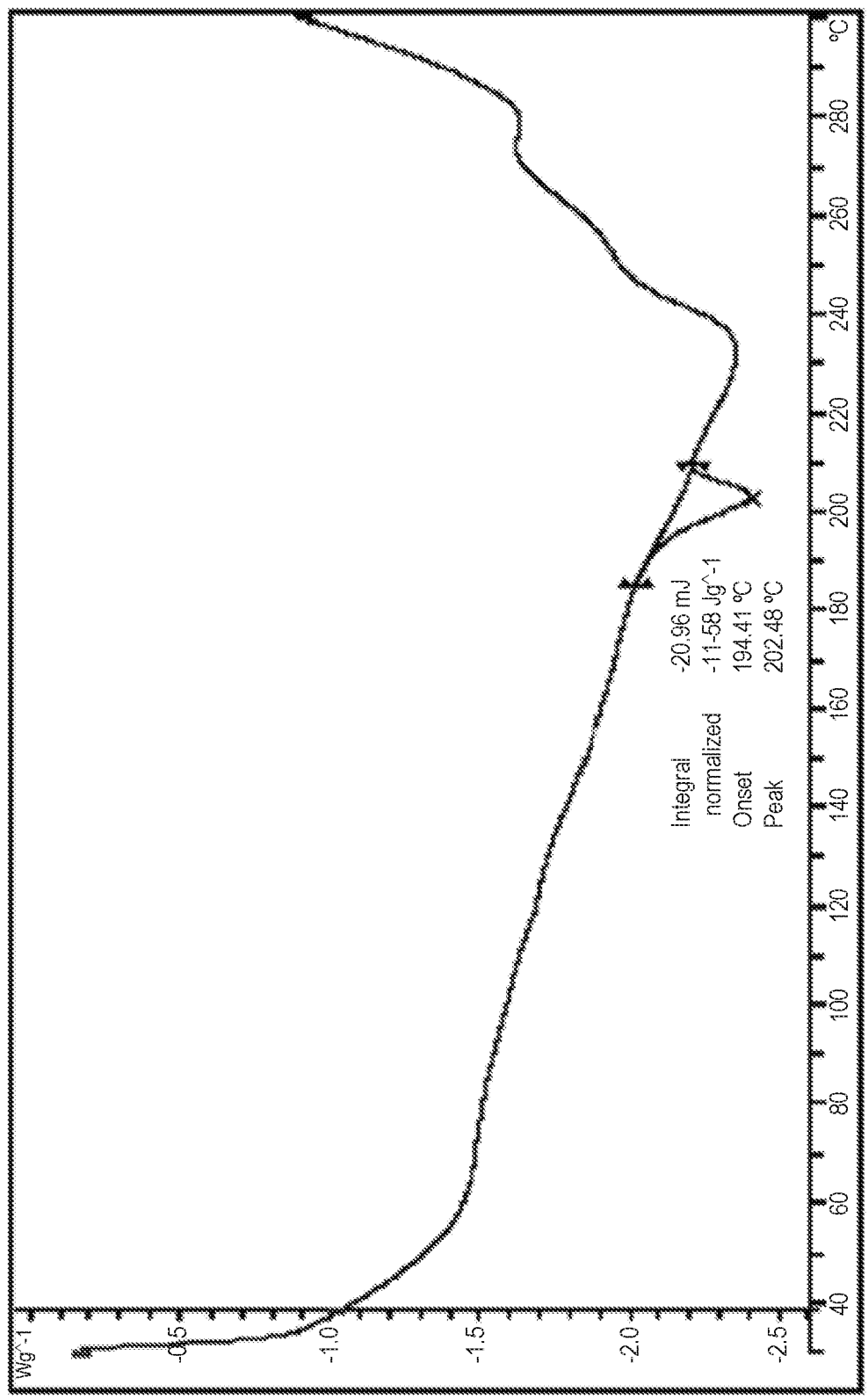
FIG. 25 shows a DSC result for Polymorph Form C.

In one embodiment, crystalline polymorph Form C has a differential scanning calorimetry profile substantially as shown in FIG. 25.

In one embodiment, crystalline polymorph Form C has an X-ray diffraction pattern as previously described above, and further has at least one of the following: (a) a thermogravimetric analysis profile showing a first weight loss of about 2% to about 3% between about 70° C. and about 80° C.; a second weight loss of about 50% to about 60% between about 275° C. and about 420° C., and/or a third weight loss of about 5% to about 6% between about 460° C. and about 480° C.; and (b) a differential scanning calorimetry profile comprising a first endotherm with an onset point at about 194° C. with a peak at 202.5° C.

In one embodiment, crystalline polymorph Form C has an X-ray diffraction pattern as previously described above, and further has at least one of the following: (a) a thermogravimetric analysis profile substantially as shown in FIG. 26; and (b) a differential scanning calorimetry profile substantially as shown in FIG. 25.

In one aspect, provided herein are methods for preparing the crystalline polymorph Form C. In one embodiment, the method comprises combining Compound 1 in a first solvent with a potassium basic material; stirring the mixture for about 1 to 16 hours, about 2 to 15 hours, about 3 to 14 hours, about 4 to 13 hours, or about 5 to 12 hours; evaporating the first solvent; adding a second solvent; stirring the mixture at about 50° C. to about 80° C., about 60° C. to about 75° C., or about 65° C. to about 70° C. for about 0.5 to about 1 hour; stirring at room temperature for about 1 hour to 3 hours; collecting the solid by filtration and drying to provide crystalline polymorph Form C. In one embodiment, the mixture is stirred at about 70° C. for about 40 minutes. In another embodiment, the mixture is stirred at room temperature for about 2 hours.

In one embodiment, crystalline polymorph Form C is characterized by a melting point.

In another embodiment, the method for preparing the crystalline polymorph Form C, comprises combining Compound 1 in a first solvent with a potassium basic material and water; stirring the reaction mixture for 10 minutes; adding dichloromethane; extracting the water layer with dichloromethane; collecting organic layers and evaporating the organic layer to give a solid; adding a second solvent to the solid; stirring the mixture at about 50° C. to about 90° C., about 60° C. to about 80° C., or about 70° C. to about 75° C. for about 0.5 to about 2 hours; stirring the mixture at room temperature for about 1 hour to 3 hour; collecting the solid by filtration and drying to provide crystalline polymorph Form C. In one embodiment, the mixture is stirred at about 75° C. for about one hour. In another embodiment, the mixture is stirred at room temperature for about 2 hours.

In one embodiment, the first solvent is methanol. In another embodiment, the second solvent is selected from the group consisting of 2-propanol, ethanol, and 1:1 mixed methanol and water. In one embodiment, the second solvent is ethanol.

c. Pharmaceutical Compositions

Provided herein are pharmaceutical compositions including a compound provided herein as an active ingredient, e.g., a compound of Formula I or II, or a pharmaceutically acceptable salt, solvate, or prodrug thereof; in combination with a pharmaceutically acceptable vehicle, carrier, diluent, excipient, or a mixture thereof.

In another embodiment, the pharmaceutical compositions comprise Compound 1 or a pharmaceutically acceptable salt thereof, or one or more solid state forms of Compound 1. In some embodiments, the pharmaceutical compositions comprise Compound 1 or a pharmaceutically acceptable salt thereof, or one or more solid state forms of Compound 1 or a pharmaceutically acceptable salt thereof in combination with a pharmaceutically acceptable vehicle, carrier, diluent, excipient, or a mixture thereof.

In one embodiment, the pharmaceutical compositions comprise Compound 1 or a pharmaceutically acceptable salt thereof, or amorphous free acid of Compound 1 in combination with a pharmaceutically acceptable vehicle, carrier, diluent, excipient, or a mixture thereof.

In one embodiment, the pharmaceutical compositions comprise Compound 1 or a pharmaceutically acceptable salt thereof, or amorphous sodium salt of Compound 1 in combination with a pharmaceutically acceptable vehicle, carrier, diluent, excipient, or a mixture thereof.

In one embodiment, the pharmaceutical compositions comprise Compound 1 or a pharmaceutically acceptable salt thereof, or crystalline polymorph Form A in combination with a pharmaceutically acceptable vehicle, carrier, diluent, excipient, or a mixture thereof.

In one embodiment, the pharmaceutical compositions comprise Compound 1 or a pharmaceutically acceptable salt thereof, or crystalline polymorph Form B in combination with a pharmaceutically acceptable vehicle, carrier, diluent, excipient, or a mixture thereof.

In one embodiment, the pharmaceutical compositions comprise Compound 1 or a pharmaceutically acceptable salt thereof, or crystalline polymorph Form C in combination with a pharmaceutically acceptable vehicle, carrier, diluent, excipient, or a mixture thereof.

In one embodiment, the pharmaceutical compositions of the present invention comprise from about 0.1 percent by weight to about 99 percent or more by weight of one or more solid state forms of Compound 1. The amount of one or more solid state forms of Compound 1 contained in the dosage unit composition employed for adult human treatment ranges from, for example, about 0.01 mg to about 2500 mg, from about 0.1 mg to about 1000 mg, from about 1 mg to about 1000 mg, from about 1 mg to about 500 mg, from about 0.1 mg to about 500 mg, from about 0.1 mg to about 100 mg, from about 0.5 mg to about 100 mg, from about 1 mg to about 100 mg, from about 10 mg to about 1000 mg, from about 10 mg to about 500 mg, or from about 10 mg to about 100 mg. In another embodiment, the dose or subdoses can be administered in the form of dosage units comprising about 10 mg, about 25 mg, about 50 mg, about 75 mg, about 100 mg, about 250 mg, about 300 mg, about 400 mg, about 500 mg, about 600 mg, about 700 mg, about 800 mg, about 900 mg, or about 1000 mg of one or more solid state forms of Compound 1.

In one embodiment, the pharmaceutical compositions comprise from about 0.1 percent by weight to about 99 percent or more by weight of a polymorph crystalline solid state form of Compound 1. In one embodiment, the polymorph crystalline solid state form of Compound 1 is Form A.

In one embodiment, the present disclosure is directed to a process for preparing a pharmaceutical composition, the process comprising: (a) combining an active ingredient (e.g., Compound 1 or a pharmaceutically acceptable salt thereof or a solid state form of Compound 1) and at least a portion of one additional composition component to form a dry granulation material; (b) combining the dry granulation material with the remaining composition components; and (c) compressing the composition to form the pharmaceutical composition. In one embodiment, the pharmaceutical composition is a tablet.

In one embodiment, the compressed tablet comprises a polymorph crystalline solid state form of Compound 1. In one embodiment, the polymorph crystalline solid state form of Compound 1 is Form A.

In one embodiment, the pharmaceutical composition is a capsule dosage form. In one embodiment, the capsule dosage form comprises a polymorph crystalline solid state form of Compound 1. In one embodiment, the polymorph crystalline solid state form of Compound 1 is Form A.

The pharmaceutical compositions may be formulated in various dosage forms, including, but not limited to, the dosage forms for oral, parenteral, subcutaneous, intramuscular, transmucosal, inhaled, or topical/transdermal administration. The pharmaceutical compositions may also be formulated as modified release dosage forms, including, but not limited to, delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, Remington: The Science and Practice of Pharmacy, supra; Modified-Release Drug Deliver Technology, Rathbone et al., Eds., Drugs and the Pharmaceutical Science, Marcel Dekker, Inc.: New York, NY, 2003; Vol. 126) (incorporated herein by reference).

The pharmaceutical compositions provided herein may be provided in a unit- or multiple-dosage form. A unit-dosage form, as used herein, refers to a physically discrete unit suitable for administration to a subject as is known in the art. Examples of a unit-dosage form include an ampoule, syringe, and individually packaged tablet and capsule. A unit-dosage form may be administered in fractions or multiples thereof.

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens can be adjusted over time according to individual need and the professional judgment of the person administering or supervising the administration of the pharmaceutical compositions provided herein.

Exemplary pharmaceutical compositions and components for use therewith are described in U.S. Pat. No. 8,907,103, the contents of which are herein incorporated by reference.

d. Administration

The pharmaceutical compositions provided herein can be administered by any suitable method, e.g., orally, parenterally, topically, intraventricularly, by inhalation spray, rectally, nasally, buccally, vaginally or via an implanted reservoir. Exemplary pharmaceutical compositions for oral administration, parenteral administration, or topical administration are described in U.S. Pat. No. 10,076,504, the contents of which are herein incorporated by reference.

A. Oral Administration

The pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions (e.g., aqueous or oil suspensions), wafers, sprinkles, elixirs, syrups, bolus, electuaries, or pastes. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, preserving agents, sweetening agents, and flavoring agents.

B. Parenteral Administration

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

C. Topical Administration

The pharmaceutical compositions provided herein may be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, bolus, electuaries, pastes, and dermal patches. The topical formulation of the pharmaceutical compositions provided herein may also comprise liposomes, micelles, microspheres, nanosystems, and mixtures thereof.

D. Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microparticles, microspheres, liposomes, and combinations thereof. The release rate of the active ingredient(s) can also be modified by varying the particle sizes and polymorphism of the active ingredient(s). Exemplary pharmaceutical compositions formulated as a modified release dosage form are described in U.S. Pat. No. 10,076,504, the contents of which are herein incorporated by reference.

e. Methods of Use

In one embodiment, provided herein is a method of treating, preventing, or ameliorating a condition, disorder, or disease associated with impaired glucose tolerance, a metabolic syndrome, or a glucagon receptor, or one or more symptoms thereof, comprising administering to a subject having or being suspected to have such a condition, disorder, or disease, a therapeutically effective amount of a compound provided herein, e.g., a compound of Formula I, II, or III, or a pharmaceutically acceptable salt, solvate, or prodrug thereof; or a pharmaceutical composition thereof; or one or more solid state forms thereof. In one embodiment, the subject is a mammal. In another embodiment, the subject is a human. In one embodiment, the solid state form is amorphous free acid of Compound 1. In another embodiment, the solid state form is amorphous sodium salt of Compound 1. In another embodiment, the solid state form is Polymorph Form A. In another embodiment, the solid state form is Polymorph Form B. In another embodiment, the solid state form is Polymorph Form C.

In another embodiment, provided herein is a method of treating, preventing, or ameliorating a condition, disorder, or disease responsive to a decrease in the hepatic glucose production or in the blood glucose level, or one or more symptoms thereof, comprising administering to a subject having or being suspected to have such a condition, disorder, or disease, a therapeutically effective amount of a compound provided herein, e.g., a compound of Formula I, II, or III, or a pharmaceutically acceptable salt, solvate, or prodrug thereof; or a pharmaceutical composition thereof; or one or more solid state forms thereof. In one embodiment, the subject is a mammal. In another embodiment, the subject is a human. In one embodiment, the solid state form is amorphous free acid of Compound 1. In another embodiment, the solid state form is amorphous sodium salt of Compound 1. In another embodiment, the solid state form is Polymorph Form A. In another embodiment, the solid state form is Polymorph Form B. In another embodiment, the solid state form is Polymorph Form C.

The conditions and diseases treatable with the methods provided herein include, but are not limited to, type 1 diabetes, type 2 diabetes, gestational diabetes, ketosis, ketoacidosis, nonketotic hyperosmolar coma (nonketotic hyperglycemia), impaired glucose tolerance (IGT), insulin resistance syndromes, syndrome X, low HDL levels, high LDL levels, hyperglycemia, hyperinsulinemia, hyperlipidemia, hypertriglyceridemia, hyperlipoproteinemia, hypercholesterolemia, dyslipidemia, arteriosclerosis, atherosclerosis, glucagonomas, acute pancreatitis, cardiovascular diseases, hypertension, cardiac hypertrophy, gastrointestinal disorders, obesity, vascular restenosis, pancreatitis, neurodegenerative disease, retinopathy, nephropathy, neuropathy, accelerated gluconeogenesis, excessive (greater than normal levels) hepatic glucose output, and lipid disorders. In some embodiments, the ketoacidosis is diabetic ketoacidosis, alcoholic ketoacidosis, or starvation ketoacidosis.

Provided herein are also methods of delaying the time to onset or reducing the risk of the development or progression of a disease or condition responsive to decreased hepatic glucose production or responsive to lowered blood glucose levels.

Depending on the condition, disorder, or disease to be treated and the subject's condition, a compound provided herein may be administered by oral, parenteral (e.g., intramuscular, intraperitoneal, intravenous or intraarterial (e.g., via catheter), ICV, intracisternal injection or infusion, subcutaneous injection, or implant), inhalation, nasal, vaginal, rectal, sublingual, and/or topical (e.g., transdermal or local) routes of administration, and may be formulated alone or together in suitable dosage unit with a pharmaceutically acceptable vehicle, carrier, diluent, excipient, or a mixture thereof, appropriate for each route of administration.

The dose may be in the form of one, two, three, four, five, six, or more sub-doses that are administered at appropriate intervals per day. The dose or sub-doses can be administered in the form of dosage units containing from about 0.01 to about 2500 mg, from about 0.1 mg to about 1,000 mg, from about 1 mg to about 1000 mg, from about 1 mg to about 500 mg, from about 0.1 mg to about 500 mg, from about 0.1 mg to about 100 mg, from about 0.5 mg about to about 100 mg, from about 1 mg to about 100 mg, from about 10 mg to about 1000 mg, from about 10 mg to about 500 mg, or from about 10 mg to about 100 mg of active ingredient(s) per dosage unit. For example, the dose or subdoses can be administered in the form of dosage units containing about 10 mg, about 25 mg, about 50 mg, about 75 mg, about 100 mg, about 250 mg, about 300 mg, about 400 mg, about 500 mg, about 600 mg, about 700 mg, about 800 mg, about 900 mg, or about 1000 mg. If the condition of the patient requires, the dose can, by way of alternative, be administered as a continuous infusion.

In certain embodiments, an appropriate dosage level is about 0.01 to about 100 mg per kg patient body weight per day (mg/kg per day), about 0.01 to about 50 mg/kg per day, about 0.01 to about 25 mg/kg per day, or about 0.05 to about 10 mg/kg per day, which may be administered in single or multiple doses. A suitable dosage level may be about 0.01 to about 100 mg/kg per day, about 0.05 to about 50 mg/kg per day, or about 0.1 to about 10 mg/kg per day. Within this range, the dosage may be about 0.01 to about 0.1, about 0.1 to about 1.0, about 1.0 to about 10, or about 10 to about 50 mg/kg per day.

For oral administration, the pharmaceutical compositions can be provided in the form of tablets containing about 1.0 to about 1,000 mg of the active ingredient, for example, about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the patient to be treated. The compositions may be administered on a regimen of 1 to 4 times per day, including once, twice, three times, and four times per day. In various embodiments, the compositions may be administered before a meal, after a meal, in the morning hours, after awakening, in the evening hours, and/or at bedtime.

It will be understood, however, that the specific dose level, frequency, and timing of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In still another embodiment, provided herein is a method of modulating the biological activity of a glucagon receptor, comprising contacting the receptor with one or more of the compounds provided herein, e.g., a compound of Formulas I, II, or III, including a single enantiomer, a mixture of enantiomers, or a mixture of diastereomers thereof, or a pharmaceutically acceptable salt, solvate, or prodrug thereof or a pharmaceutical composition thereof or one or more solid state forms thereof. In one embodiment, the glucagon receptor is expressed by a cell. In one embodiment, the solid state form is amorphous free acid of Compound 1. In another embodiment, the solid state form is amorphous sodium salt of Compound 1. In another embodiment, the solid state form is Polymorph Form A. In another embodiment, the solid state form is Polymorph Form B. In another embodiment, the solid state form is Polymorph Form C.

The compounds provided herein may also be combined or used in combination with each other or other therapeutic agents useful in the treatment, prevention, or amelioration of one or more symptoms of the conditions, disorders, or diseases for which the compounds provided herein are useful. As used herein, the term "in combination" includes the use of more than one therapeutic agent. However, the use of the term "in combination" does not restrict the order in which therapeutic agents are administered to a subject with a condition, disorder, or disease. A first therapeutic agent (e.g., a therapeutic agent such as a compound provided herein) can be administered prior to (e.g., 5 min, 15 min, 30 min, 45 min, 1 hr, 2 hrs, 4 hrs, 6 hrs, 12 hrs, 24 hrs, 48 hrs, 72 hrs, 96 hrs, 1 wk, 2 wks, 3 wks, 4 wks, 5 wks, 6 wks, 8 wks, or 12 wks before), concomitantly with, or subsequent to (e.g., 5 min, 15 min, 30 min, 45 min, 1 hr, 2 hrs, 4 hrs, 6 hrs, 12 hrs, 24 hrs, 48 hrs, 72 hrs, 96 hrs, 1 wk, 2 wks, 3 wks, 4 wks, 5 wks, 6 wks, 8 wks, or 12 wks after) the administration of a second therapeutic agent to a subject to be treated.

When a compound provided herein is used contemporaneously with one or more additional therapeutic agents, a pharmaceutical composition containing such other agents in addition to the compound provided herein may be utilized, but is not required. Accordingly, the pharmaceutical compositions provided herein include those that also contain one or more other therapeutic agents, in addition to a compound provided herein.

In one embodiment, the other therapeutic agent is an antidiabetic agent. Suitable antidiabetic agents include, but are not limited to, insulin sensitizers, biguanides (e.g., metformin), PPAR agonists (e.g., triglitazone, pioglitazone, and rosiglitazone), insulin and insulin mimetics, somatostatin, α-glucosidase inhibitors (e.g., voglibose, miglitol, and acarbose), dipeptidyl peptidase-4 inhibitors, SGLT-2 inhibitors, liver X receptor modulators, insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, sulfonylureas, tolazamide, tolbutamide, tolcyclamide, nateglinide, and repaglinide), other glucagon receptor antagonists, GLP-1, GLP-1 mimetics (e.g., exenatide, liraglutide, DPPIV inhibitors), GLP-1 receptor agonists, GIP, GIP mimetics, GIP receptor agonists, PACAP, PACAP mimetics, PACAP receptor 3 agonists, cholesterol lowering agents, HMG-CoA reductase inhibitors (e.g., statins, such as lovastatin, simvastatin, pravastatin, fluvastatin, atorvastatin, itavastatin, rivastatin, NK-104 (a.k.a. itavastatin, nisvastatin, and nisbastatin), and ZD-4522 (also known as rosuvastatin, atavastatin, and visastatin)), a cholesterol absorption inhibitor (e.g., ezetimibe), sequestrants, nicotinyl alcohol, nicotinic acid and salts thereof, PPAR α agonists, PPAR α/γ dual agonists, inhibitors of cholesterol absorption, acyl CoA: cholesterol acyltransferase inhibitors, anti-oxidants, PPAR δ agonists, antiobesity compounds, ileal bile acid transporter inhibitors, anti-inflammatory agents, and protein tyrosine phosphatase-1B (PTP-1B) inhibitors.

The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

The weight ratio of a compound provided herein to the second active ingredient depends upon the effective dose of each ingredient. Generally, an effective dose of each will be used. Thus, for example, when a compound provided herein is combined with a PPAR agonist the weight ratio of the compound provided herein to the PPAR agonist will generally range from about 1000:1 to about 1:1000 or about 200:1 to about 1:200. Combinations of a compound provided herein and other active ingredients will generally also be within the aforementioned range, but in each case, an effective dose of each active ingredient should be used.

f. Synthesis of Compounds and Salts Thereof Compound 1 and its salts thereof were first disclosed in International Application WO2010/019830A1, which is herein incorporated by reference in its entirety. However, the isolation and commercial-scale preparation of Compound 1 or salts thereof, as well as preparation of solid state forms of Compound 1 or salts thereof, presented a challenge at least because of epimerization of the chiral center of Compound 1 and detergent-like properties of salts of Compound 1, due to the presence of the —$SO_3M$ group (e.g., M is a sodium cation or ammonium cation). There was, therefore, a need for improved methods for commercial-scale preparation of Compound 1 or salts thereof and for solid state form preparation of Compound 1 or salts thereof.

Compounds of Formula I, II, or III and salts thereof of the present disclosure can be prepared according to the methodology outlined in the following general synthetic schemes or with modifications of these schemes that will be evident to persons skilled in the art, or by other methods readily known to those of skill in the art.

In the following sections, the following abbreviations are used: THF: Tetrahydrofuran; DBU: 1,8-Diazabicyclo[5.4.0]undec-7-en; DCM: dichloromethane; DIPEA: N,N-diisopropylethylamine; DME: 1,2-Dimethoxyethane; DMF: N,N-Dimethylformamide; DCC: N,N'-Dicyclohexylcarbodiimide; EDCI or EDC: 1-(3-Dimethylaminopropyl)-3-ethyl carbodiimide hydrochloride; LiHMDS: Lithium hexamethyldisilyl amide; HOBt: 1-Hydroxybenzotriazole; EtOAc/EA: Ethyl acetate; EtOH: Ethanol; IPA: iso-Propanol; ACN: Acetonitrile; DIPEA: N,N-Diisopropyl-ethyl amine; and MTBE: Methyl-tert-butyl ether; TEA: trimethylamine; TFA: trifluoroacetic acid.

The compounds of Formula I, II, or III and salts thereof can be generated using the synthetic strategy shown in Schemes 1-5. Schemes 1 and 2 provide a synthetic route to make kilograms of Polymorph Form A of the compound of Formula III. Scheme 3 provides a synthetic route to make salts of compounds of Formula I. Schemes 4 and 5 provide two different synthetic routes to make salts of the compound of Formula III. In Schemes 4 and 5, the carboxylic acid is coupled in the presence of a water-soluble carbodiimide with a primary amine as shown.

Scheme 1

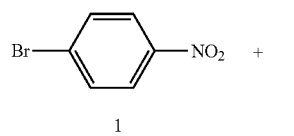

1

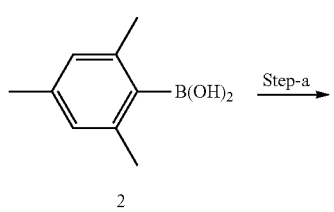

2

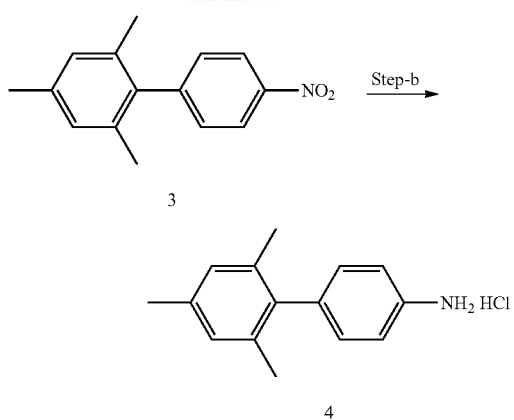

3

4

Intermediate 4 can be prepared through two step reactions illustrated in scheme 1. The first step is carried out by Suzuki coupling of starting materials 1 and 2. The second step converts a nitro group of intermediate 3 to a $NH_2$ group.

Scheme 2

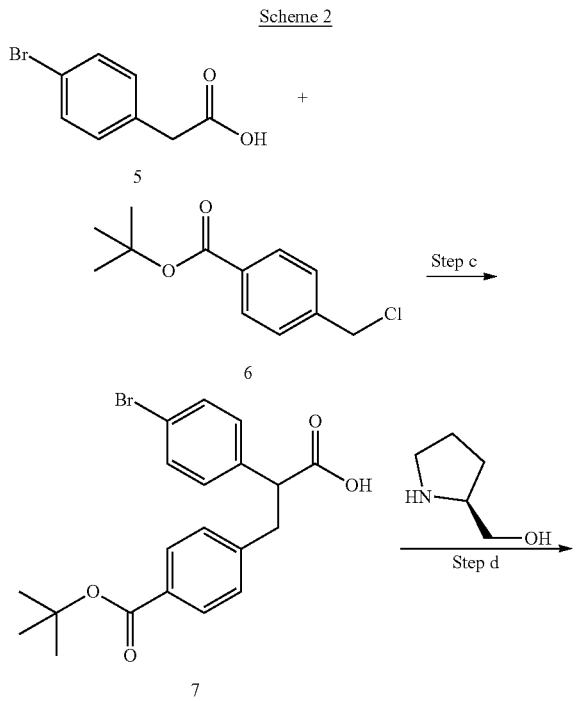

5

6

7

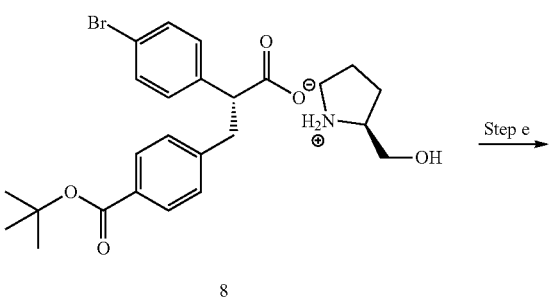

8

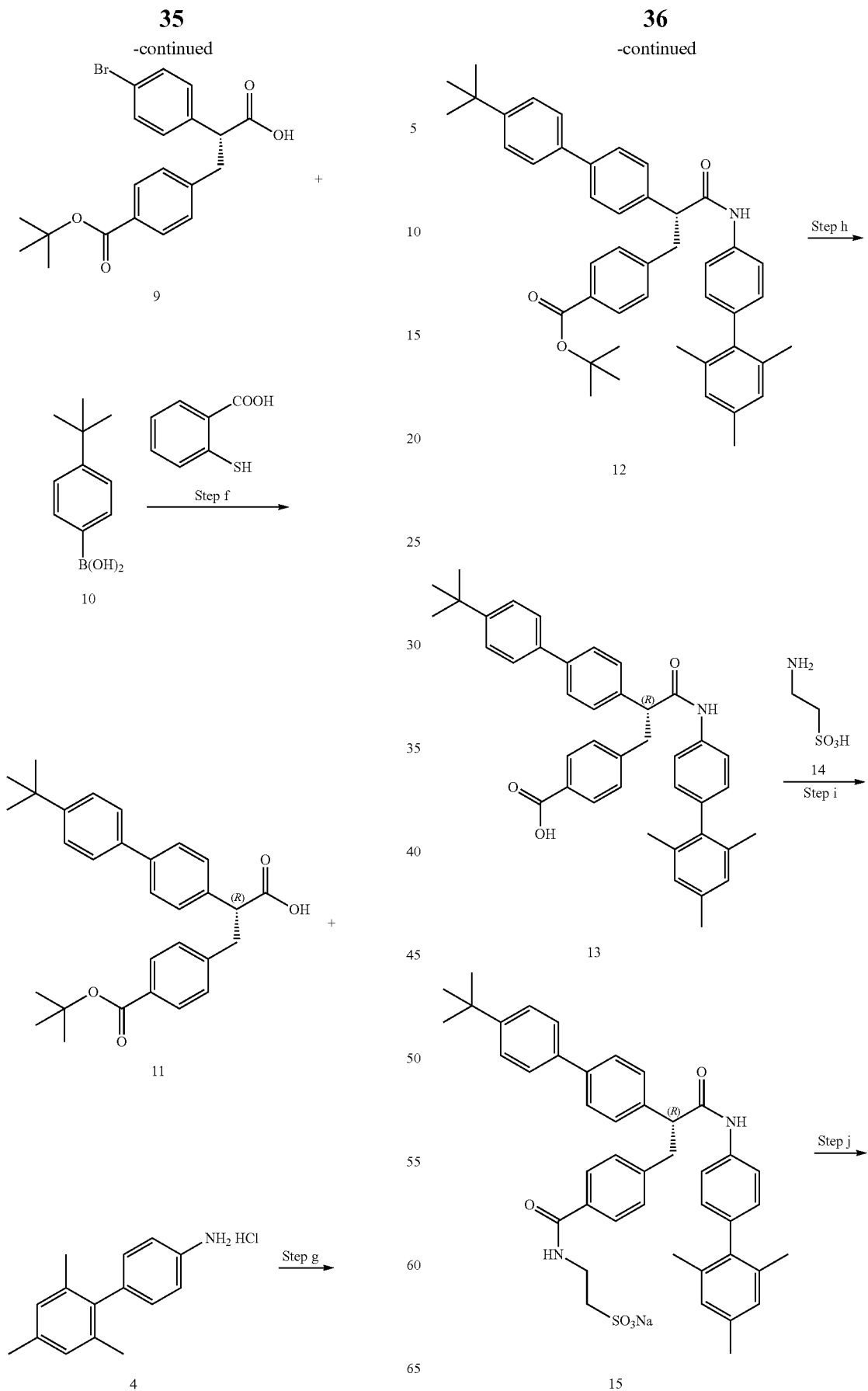

-continued

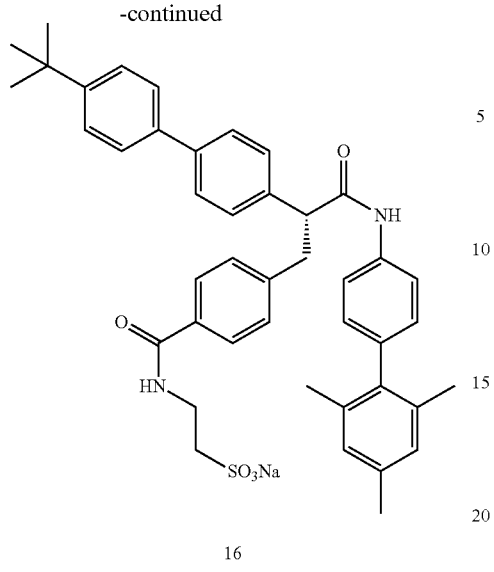

16

Compounds 15 and 16 can be generated through multiple steps illustrated in Scheme 2. Racemic intermediate 7 can be prepared by reacting starting material 5 with a base (such as lithium diisopropylamide or lithium hexamethyldisilylamide) in a suitable solvent (such as THF, DMF, or DME), followed by reaction with starting material 6. Chiral intermediate 9 can be prepared by reacting racemic intermediate 7 with a chiral amine such as (S)-pyrrolidin-2-ylmethanol in a suitable solvent (such as THF or EtOAc) to generate precipitation of intermediate 8, then by acidifying intermediate 8 in a suitable solvent (such as EtOAc) with an acid (such as formic acid).

Intermediate 11 can be prepared by a Suzuki coupling of intermediates 9 and 10 in the presence of a catalyst (such as $PdCl_2[P(o-Tol)_3]_2$). The existence of a Pd catalyst in the reaction presents a challenge for removal to meet Good Manufacturing Practice ("GMP") requirements when the reaction scale is at kilogram level. Surprisingly, as disclosed herein, 2-mercaptobenzoic acid demonstrates an unexpected effect on removing the Pd catalyst. The Pd catalyst content is significantly reduced and final compounds 15 and 16 prepared by this route meet GMP requirements.

Intermediate 12 can be prepared by methods known for amide bond formation reactions. As an example, reacting intermediate 11 with intermediate 4 in the presence of an activating agent (for example, HATU, DCC, or EDCI with or without a catalyst such as DMAP or HOBT) with a base (such as TEA, DIPEA, or DBU) in a suitable solvent (such as DCM or THF) produces intermediate 12.

Intermediate 13 can be prepared by reacting intermediate 12 with an acid (such as HCl or TFA) in a suitable solvent (such as DCM or ethanol). The reaction time varies when a different acid is applied. For example, the reaction took longer when a solution of HCl in ethanol was used. In addition, maintenance of enantiomeric excess ("ee") of intermediate 13 was challenging. Some erosion of ee was observed when HCl was used. The ee of intermediate 13 was unexpectedly maintained when TFA was used. Compound 15 can be prepared by reacting intermediate 13 with taurine derivatives using standard amide bond forming reactions. Crystalline compound 16 can be generated by recrystallization of compound 15 in a suitable solvent (such as EtoAc, EtOH, and/or $H_2O$).

Scheme 3

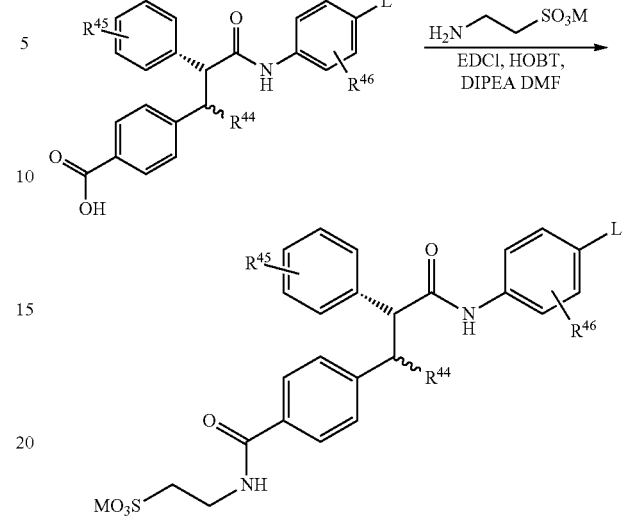

In one embodiment, M is a metal cation. In one embodiment, M is sodium cation.

Scheme 4

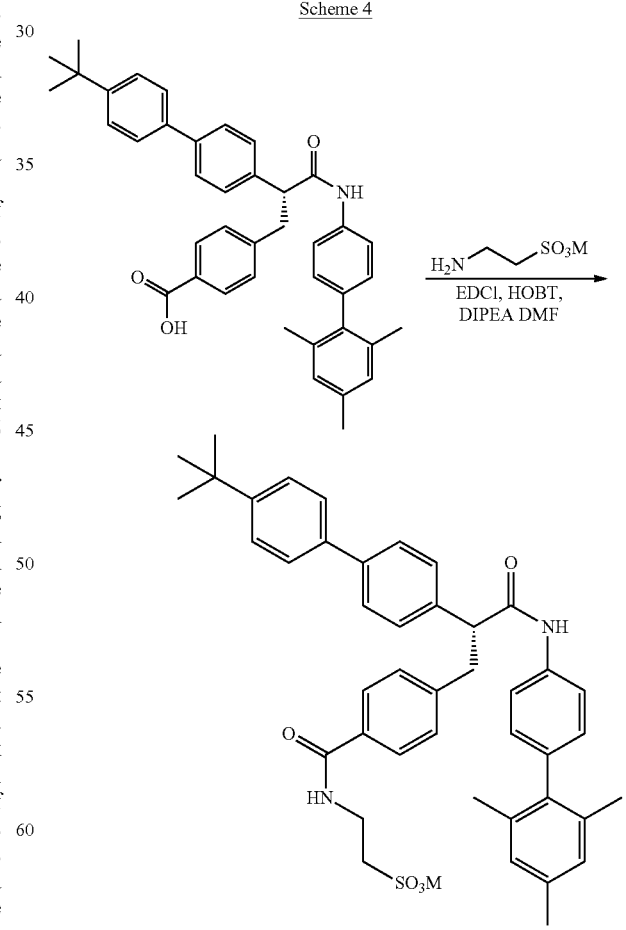

In some embodiments, the reaction is carried out at 15° C. for 24 hours. In one embodiment, M is a metal cation. In one embodiment, M is selected from the group consisting of sodium cation, calcium cation, and potassium cation.

Scheme 5

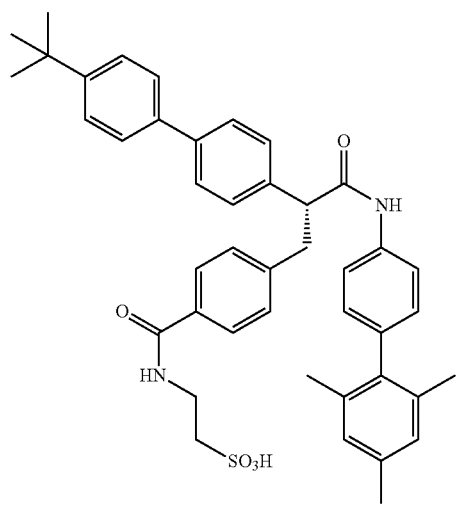

In one embodiment, M is a metal. In one embodiment, M is selected from the group consisting of sodium, calcium, and potassium.

Having now fully described this invention, it will be understood by those of ordinary skill in the art that the same can be performed within a wide and equivalent range of conditions, formulations and other parameters without affecting the scope of the invention or any embodiment thereof.

The following examples are provided so that this disclosure can be more fully understood. They should not be construed as limiting the disclosure in any way.

Example 1

Preparation of Kilograms of Sodium (R)-2-(4-(2-(4'-(tert-butyl)-[1,1'-biphenyl]-4-yl)-3-oxo-3-((2',4',6'-trimethyl-[1,1'-biphenyl]-4-yl)amino)propyl)benzamido)ethane-1-sulfonate Step a: Preparation of 2,4,6-trimethyl-4'-nitro-1,1'-biphenyl (Intermediate 3)

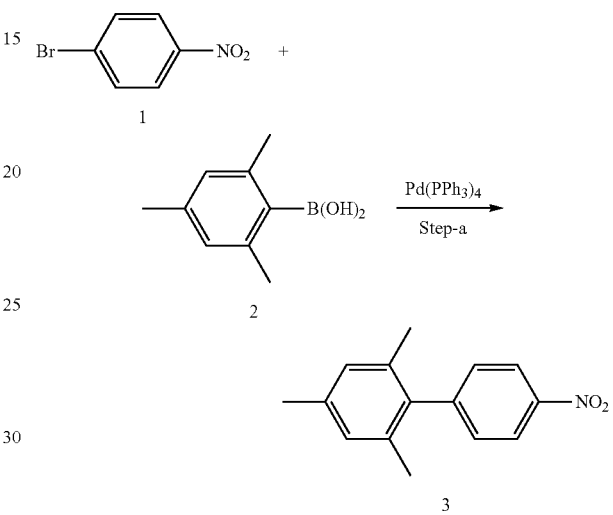

1-bromo-4-nitrobenzene (reagent 1, 9.0 Kg, 1.0×, 1.0 eq) and mesitylboronic acid (reagent 2, 8.0 Kg, 0.87-0.89×, 1.1 eq) were added to a reactor 1. To this mixture was added Na$_2$CO$_3$ (13.4 Kg, 1.47-1.50×, 2.8 eq), followed by DMAc (17.0 Kg, 1.87-1.90×) and process water (73 Kg, 8.0-8.1×). Then the reactor was degassed with N$_2$ twice. To the mixture was added Pd(PPh$_3$)$_4$ (1.03 Kg, 0.112-0.116×, 2% eq). The reactor was degassed with N$_2$ twice. Then the reactor 1 was heated to 95-110° C. (internal temperature) (all the solids dissolved and a black mixture formed) and the mixture was stirred at 95-110° C. for 18-20 h. HPLC showed the ratio of reagent 1/intermediate 3 was 2.3%. The reactor was cooled to 30-40° C. To the mixture were added process water (45 Kg, 3.0-5.0×) and EtOAc (50 Kg, 4.5-5.5×). The resulting slurry was filtered through celite. The filtrate was separated, then the aqueous layer was extracted with EtOAc (42.0 Kg, 4.5-5.5×). All the organic layers were combined and washed with Na$_2$SO$_4$ (4.5-5.5×, 46 Kg each time) twice. The organic solution was concentrated to 2-4× at below 40° C. To this mixture was added EtOH (70 Kg, 7.5-8.5×). The resulting solution was concentrated to 2-4× at below 40° C. Then another batch of EtOH (70 Kg, 7.5-8.5×) was added. The resulting solution was concentrated to 6-8× at below 40° C. The temperature of the mixture was adjusted to 20-30° C. The mixture was stirred for 20-30 min. Residual EtOAc in the mixture was tested (about 0.008%). Process water (14 Kg, 1.4-1.6×) was added into the reactor. The resulted mixture was stirred for 1-2 h at 20-30° C. The solid was collected through centrifuge and dried under reduced pressure at 40-50° C. for 8-12 h to afford desired product 2,4,6-trimethyl-4'-nitro-1,1'-biphenyl (7.45 Kg, purity 99%, EtOH=0.4%, KF=0.1%.)

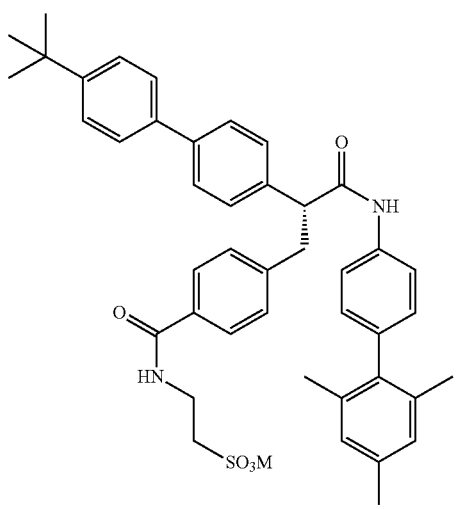

Step b: Preparation of 2',4',6'-trimethyl-[1,1'-biphenyl]-4-amine hydrochloride (Intermediate 4)

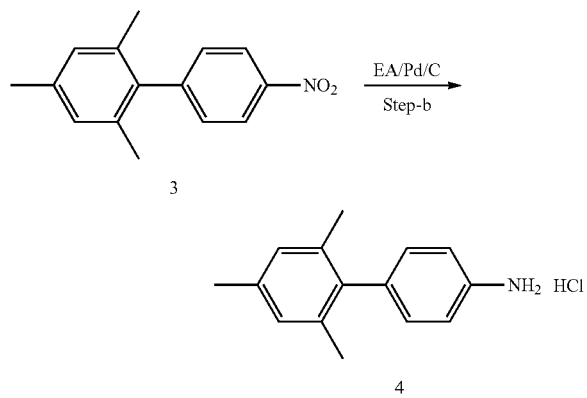

To a reactor were added EtOAc (32 Kg, 3.2-4.2×) and 2,4,6-trimethyl-4'-nitro-1,1'-biphenyl (intermediate 3, 7.44 Kg, 1.0×, 1.0 eq). The mixture was stirred until all the solid was dissolved. To the solution was added Pd/C (0.71 Kg, 0.09-0.11×, 10%, 50% water). The mixture was degassed with $N_2$ twice and stirred at 35-45° C. under $H_2$ atmosphere (0.30-0.35 MPa) for 20-30 h. HPLC showed that the ratio of intermediate 3/intermediate 4 is 1.0%. The mixture in the reactor was filtered through celite (4 Kg). 2-Mercaptobenzoic acid (2.30 Kg, 0.30-0.34×) was added to a second reactor at 15-25° C. The filtrate was transferred into the second reactor via cartridge filter. The resulting mixture was stirred at 20-25° C. for 2-3 h. Then it was stirred with aqueous $Na_2CO_3$ (45 Kg, 5-6×, 5% w/w) for 20-40 minutes three times. Every time the aqueous layer was separated off. The pH of the last two aqueous layers was about 8. HPLC showed that the ratio of 2-Mercaptobenzoic acid/intermediate 4 is about 0.4%. To the second reactor was added about 4 mol/L of HCl/EtOAc solution (12 Kg, 1.5-1.6×) slowly to adjust pH=1-2. The mixture was stirred at 0-10° C. for 1-2 h. The solid was collected through centrifuge and dried under reduced pressure at 40-50° C. to give intermediate 4 as off white solid (6.60 Kg, purity 100%, yield 101.4%).

Step c: Preparation of 2-(4-bromophenyl)-3-(4-(tert-butoxycarbonyl)phenyl)propanoic acid (Intermediate 7)

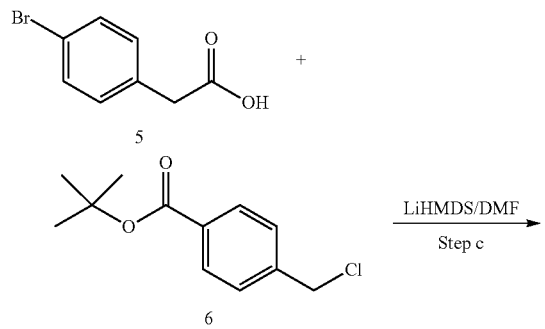

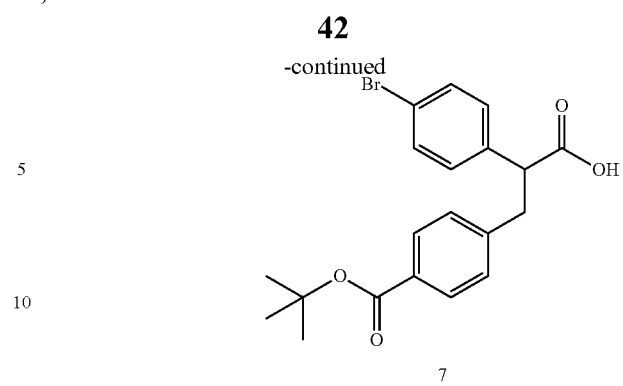

To a reactor were added 2-(4-bromophenyl)acetic acid (reagent 5, 36.0 Kg, 1.0×, 1.0 eq), DMF (237 Kg, 6.5-7.0×), and THF (90 Kg, 2.4-2.5×). The reactor was cooled to −15-0° C. To this mixture was added LiHMDS (335 Kg, 9.1-9.3×, 1 mol/L) at −15-0° C. The mixture was stirred at −15-0° C. for 2-3 h. HPLC showed that the ratio of reagent 5/intermediate 7 is about 3.9%. The reaction was quenched by 1N HCl (774 Kg, 17-20×) at −10-10° C. and diluted by EtOAc (351 Kg, 9×-10×). The mixture was stirred for 30-60 min. The organic layer was separated. The aqueous layer was extracted with EtOAc (351 Kg, 9×-10×). The organic layers were combined and washed with process water (9.5-10.5×) 3 times (370 Kg+370 Kg+365 Kg). Then the organic solution was concentrated to 5×-6×. EtOAc (440 Kg, 12×-15×) was added to the reactor. The organic solution was concentrated to 5×-6× again for the next step without further purification (KF=0.2%; residual THF=1.0%; residual DMF=0.1%, assay of intermediate 7=21.9%).

Step d: Preparation of (S)-2-(hydroxymethyl)pyrrolidin-1-ium (R)-2-(4-bromophenyl)-3-(4-(tert-butoxycarbonyl)phenyl)propanoate (Intermediate 8)

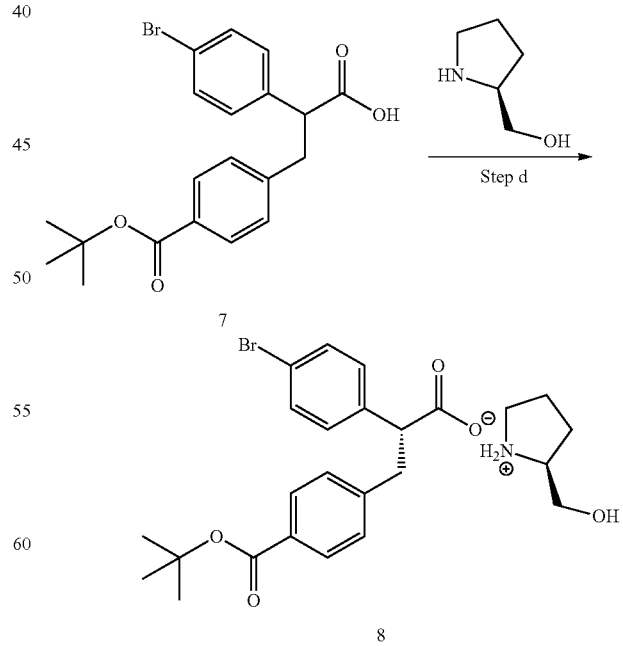

To the organic solution of step c were added EtOAc (256 Kg, 6×-8×). The mixture was warmed to 65-70° C. Then (S)-pyrrolidin-2-ylmethanol (16.9 Kg, 0.33×-0.47×) was added into the mixture at 65-70° C. The resulting mixture was stirred at 65-70° C. for 1-3 h. Then the mixture was cooled to 10-20° C. slowly and stirred at 10-20° C. for 4-6 h. The solid was collected by filtration and transferred back to the reactor. To this reactor was added THF (390 Kg, 5×-11×). The reactor was warmed to 60-65° C. and stirred for 30-60 min. Then the reactor was cooled to 30-35° C. To this reactor was added EtOAc (1083 Kg, 20×-44×). The reactor was cooled to 15-25° C. and stirred for 30-60 min. The solid was collected by filtration and transferred back to the reactor. THF (108 Kg, 3-5×) was added to the reactor. The reactor was warmed to 60-65° C. and stirred for 30-60 min. Then the reactor was cooled to 30-35° C. To this reactor was added EtOAc (433 Kg, 12-20×). The reactor was cooled to 15-25° C. and stirred for 30-60 min. The solid was collected by filtration and dried under reduced pressure at 40-50° C. for 10-15 h to afford intermediate 8 (20.50 Kg, purity 100%, ee % 99.8%, residual THF=0.01%, residual EtOAc=0.002%.)

Step e: Preparation of (R)-2-(4-bromophenyl)-3-(4-(tert-butoxycarbonyl)phenyl)propanoic acid (Intermediate 9)

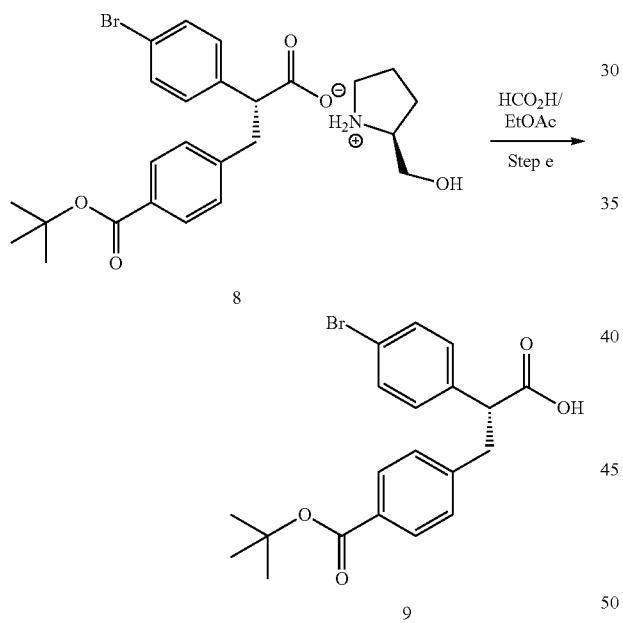

Step f: Preparation of (R)-3-(4-(tert-butoxycarbonyl)phenyl)-2-(4'-(tert-butyl)-[1,1'-biphenyl]-4-yl)propanoic acid (Intermediate 11)

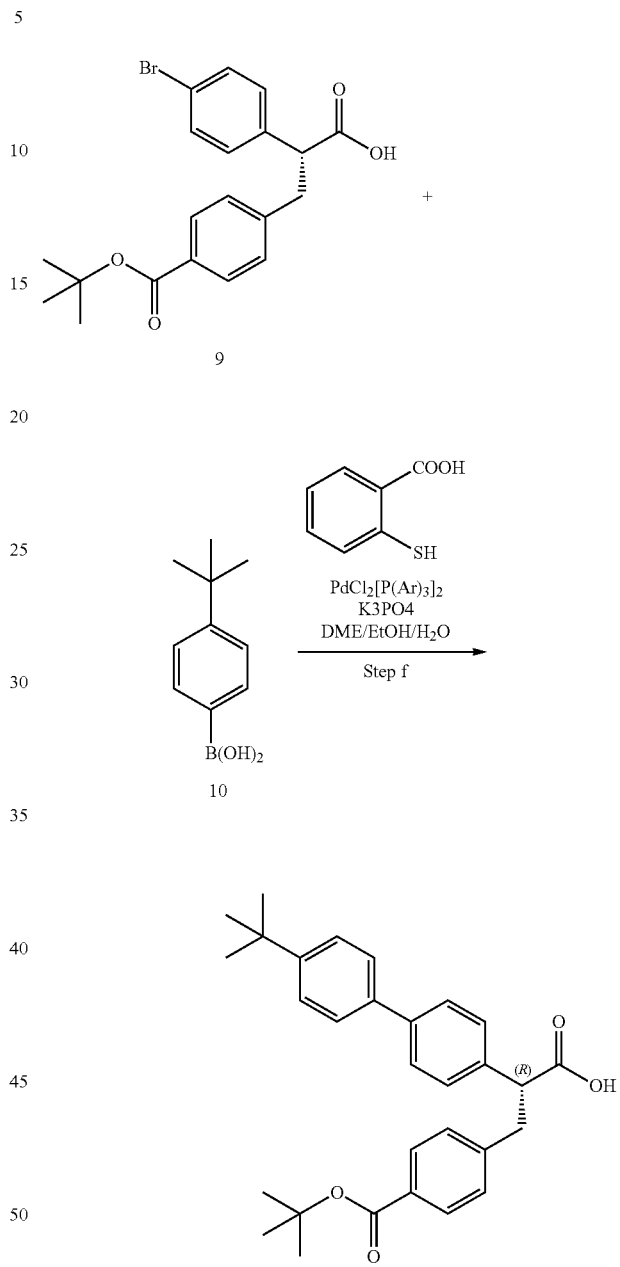

To a reactor were added intermediate 8 (18.69 Kg, 1.0×, 1.0 eq) and EtOAc (181 Kg, 9.0×-10.0×). Formic acid aqueous solution (10%, 13.1 Kg of Formic acid dissolved in 118 Kg of process water) was added into the mixture slowly to adjust pH=1-3. The mixture was stirred at 30-35° C. for 10-20 min. The aqueous layer was removed. To the reactor was added process water (171 Kg, 8.0-10.0×). The mixture was stirred for 25-35 min and the aqueous layer was removed. To the reactor was added process water (158 Kg, 8.0-10.0×). The mixture was stirred at 30-35° C. for 25-35 min and the aqueous layer was removed. To the organic phase was added DME (120 Kg, 6.0-7.0×). Then the organic solution was concentrated to 4.0×-5.0× at <30° C. under reduced pressure for the next step without further purification.

To the mixture from step e was added DME (122 Kg, 6.0-7.0×). The resulting solution was concentrated to 4.0×-5.0× at <30° C. under reduced pressure. Residual EtOAc was tested (about 2.2%). To the mixture was added DME (25 Kg, 1.0-2.0×), EtOH (36 Kg, 1.8-2.0×), process water (22 Kg, 1.1-1.3×), (4-(tert-butyl)phenyl)boronic acid (reagent 10, 9.9 Kg, 0.52-0.54×), $K_3PO_4 \cdot 3H_2O$ (28.95 Kg, 1.47-1.55×), and $PdCl_2[P(o\text{-}Tol)_3]_2$ (0.59 Kg, 0.031-0.032×). The mixture was stirred at 60-65° C. for 2-3 h. HPLC showed that the ratio of intermediate 9/intermediate 11 was about 0.03%. The reaction was cooled to 20-30° C. The mixture was concentrated to 1 to 5×-6× at <30° C. under reduced pressure and transferred to a tank. The reactor was washed with EtOAc (180 Kg, 9-10×). EtOAc solution was transferred into a tank. The reactor was further washed with process water (190 Kg, 10-12×). The water solution was transferred into the tank. The mixture in the tank was transferred to a second reactor. To the second reactor was added formic acid (50.1 Kg, 2.2-2.8×) slowly. The resulting mixture was stirred at 30-35° C. for 10 min. The aqueous layer was removed. EtOAc (20 Kg, 2-4×) was added to the second reactor. The aqueous layer was removed. The organic layer was filtered through kieselguhr (14 Kg, 0.3-1.0×). The filter cake was shed with EtOAc (84 Kg, 3-6×). The combined organic phase was washed with water (164 Kg, 8-10×).

To the organic phase was added 2-Mercaptobenzoic acid (2.95 Kg, 0.14-0.16×). The mixture was stirred at 20-25° C. for 2-3 h. To this solution was added $Na_2CO_3$ aqueous solution (5%, 223 Kg, 10×-12×). The resulting solution was stirred at 20-25° C. for 30 min. The aqueous phase was removed. Another batch of $Na_2CO_3$ aqueous solution (5%, 224 Kg, 10×-12×) was added and the mixture was stirred at 20-25° C. for 30 min. The aqueous phase was removed. HPLC showed that 2-Mercaptobenzoic acid is no more than 0.9%. To the organic phase were added process water (150 Kg, 8-10×) and formic acid (9.7 Kg, 0.50-0.55×). The mixture was stirred at 20-25° C. for 30-60 min. The aqueous phase was removed. The organic phase was washed by process water (150 Kg, 8-10×) and filtered through celite and concentrated to about 4×-5×. To the organic phase was added n-Heptane (120 Kg, 6-7×) and the mixture was concentrated to 4×-5×. The solvent swap process was repeated two more times. After the mixture was concentrated to 4×-5×, it was stirred at 5-15° C. for 30-60 min. The solid was collected by filtration and washed by n-heptane (1-3×). Then the solid was mixed with aqueous $NaHCO_3$ solution (7%, 170 Kg, 9.0-10.0×) and stirred at 20-25° C. for 60-90 min. The solid was collected by filtration and dried under vacuum at 40-50° C. to give intermediate 11 as a white solid (16.14 Kg, >99% purity, ee %=99.9%, 95% yield).

Step g: Preparation of tert-butyl (R)-4-(2-(4'-(tert-butyl)-[1,1'-biphenyl]-4-yl)-3-oxo-3-((2',4',6'-trimethyl-[1,1'-biphenyl]-4-yl)amino)propyl)benzoate (Intermediate 12)

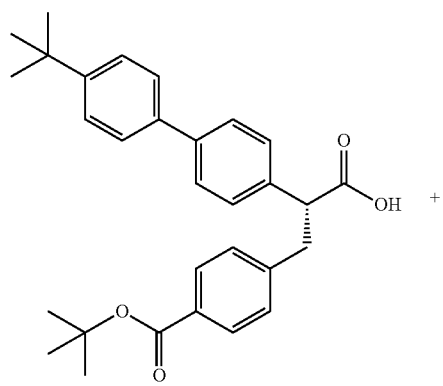

11

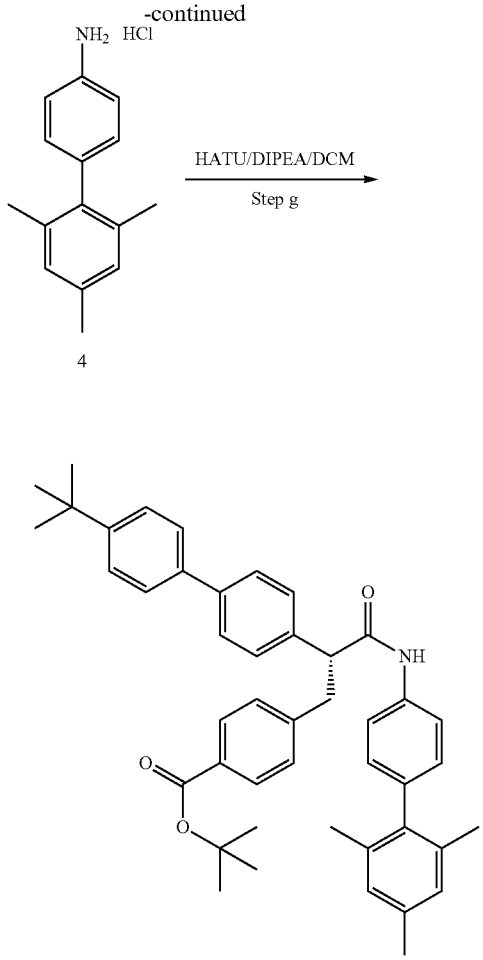

To a reactor were added (R)-3-(4-(tert-butoxycarbonyl)phenyl)-2-(4'-(tert-butyl)-[1,1'-biphenyl]-4-yl)propanoic acid (intermediate 11, 11.89 Kg, 1.0×), 2',4',6'-trimethyl-[1,1'-biphenyl]-4-amine hydrochloride (intermediate 4, 6.55 Kg, 0.55-0.59×), and DCM (160 Kg, 13-14×). The mixture was cooled to −10-0° C. DIPEA (9.5 Kg, 0.8-0.9×) was added into the reactor and the mixture was stirred at −10-0° C. for 20 min. Then HATU (14.8 Kg, 1.23-1.27×) was added. The reaction was stirred at −10-0° C. for 1-3 h. HPLC showed that the ratio of intermediate 11/intermediate 12 is about 0.04%. To the reaction mixture was added process water (20 Kg, 1.7-1.8×) and the mixture was stirred at −5-10° C. for 10 min. It was concentrated to 8×-9× at <25° C. under reduced pressure. Ethanol (30 Kg, 2.5-2.7×) and process water (11 Kg, 0.8-0.9×) were added. The resulting mixture was concentrated to 8×-9× at <25° C. under reduced pressure and stirred at 0-5° C. for 1-2 h. The solid was collected by filtration and washed by Ethanol (35 Kg, 1-3×). Sample test showed purity=83%; ee %=98%; residual HATU (% area)=17%. The solid was mixed with Ethanol (60 Kg, 4.0-5.0×) and process water (48 Kg, 3.0-4.0×). The resulting mixture was stirred at 0-5° C. for 30-60 min. The solid was collected by filtration. Sample test showed Residual HATU (% area)=13%. Then the mixture was dried under vacuum at 40-45° C. to give intermediate 12 as a white solid without further purification (20.18 Kg with 80.7% assay, 99% purity, 98% ee).

Step h: Preparation of (R)-4-(2-(4'-(tert-butyl)-[1,1'-biphenyl]-4-yl)-3-oxo-3-((2',4',6'-trimethyl-[1,1'-biphenyl]-4-yl)amino)propyl)benzoic acid (Intermediate 13)

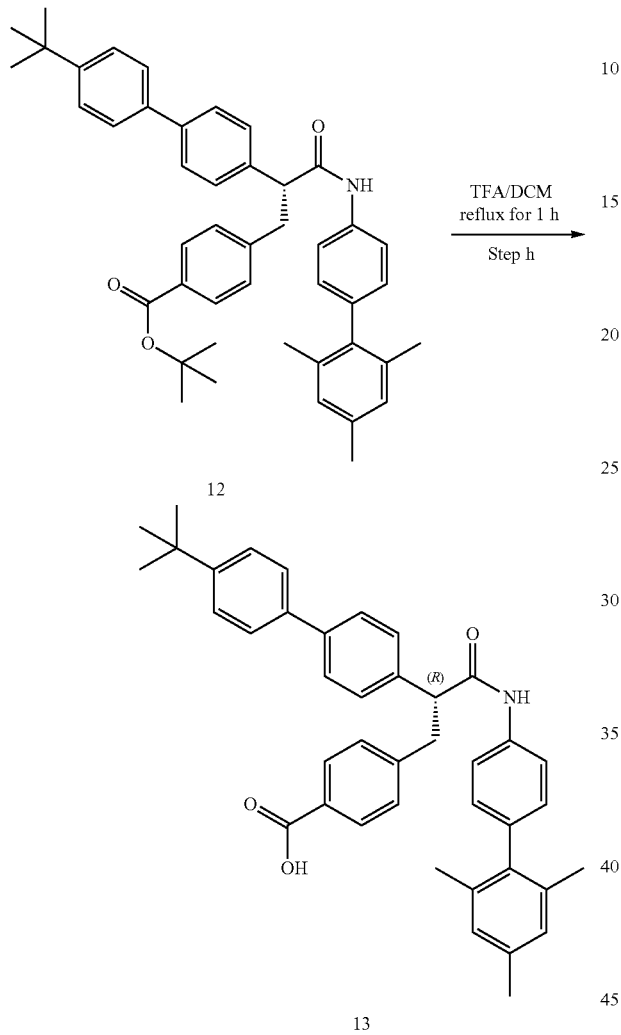

To a reactor were added tert-butyl (R)-4-(2-(4'-(tert-butyl)-[1,1'-biphenyl]-4-O-3-oxo-3-((2',4',6'-trimethyl-[1,1'-biphenyl]-4-yl)amino)propyl)benzoate (intermediate 12, 16.3 Kg, 1.0×), DCM (162 Kg, 9.8-10×), and CF$_3$COOH (94.6 Kg, 5.7-5.9×) in DCM (81 Kg, 4.8-5.0×) solution. The mixture was stirred at 35-45° C. for 1-3 h. HPLC showed that intermediate 12 is not detectable. The mixture was concentrated to 5-6×. To the reactor was added DCM (227 Kg, 13-14×). The resulting mixture was concentrated to 5-6×. Then n-heptane (100 Kg, 6-7×) was added to the reactor. The resulting mixture was concentrated to 5-6×, and another batch of n-heptane (100 Kg, 6-7×) was added to the reactor. The resulting mixture was concentrated to 5-6×. The resulted mixture was stirred at 0-10° C. for 0.5-1.0 h. The solid was collected by filtration and washed with n-heptane (36 Kg, 2×-4×). Sample test showed the purity of the solid: F %=84.4%. The solid was mixed with process water (245 Kg, 10.0-15.0×) and stirred at 15-25° C. for 1-3 h. Sample test showed the purity of the solid: F %=99%; residual HATU=3%. The mixture was further stirred at 15-25° C. for 1-3 h. Sample test showed the purity of the solid: F %=100%; Residual HATU=2%. Another batch of process water (180 Kg, 10.0-12.0×) was added to the reactor. The mixture was stirred at 15-25° C. for 1-2 h. The solid was collected by filtration and washed with process water (160 Kg, 5-10×) and dried under vacuum at 40-50° C. to give intermediate 13 as an off-white solid (14.7 Kg, F %=100%; F (% w/w)=99.0%; ee %=100%; residual HATU=0.4%).

Step i: Preparation of sodium (R)-2-(4-(2-(4'-(tert-butyl)-[1,1'-biphenyl]-4-yl)-3-oxo-3-((2',4',6'-trimethyl-[1,1'-biphenyl]-4-yl)amino)propyl)benzamido)ethane-1-sulfonate (Compound 15)

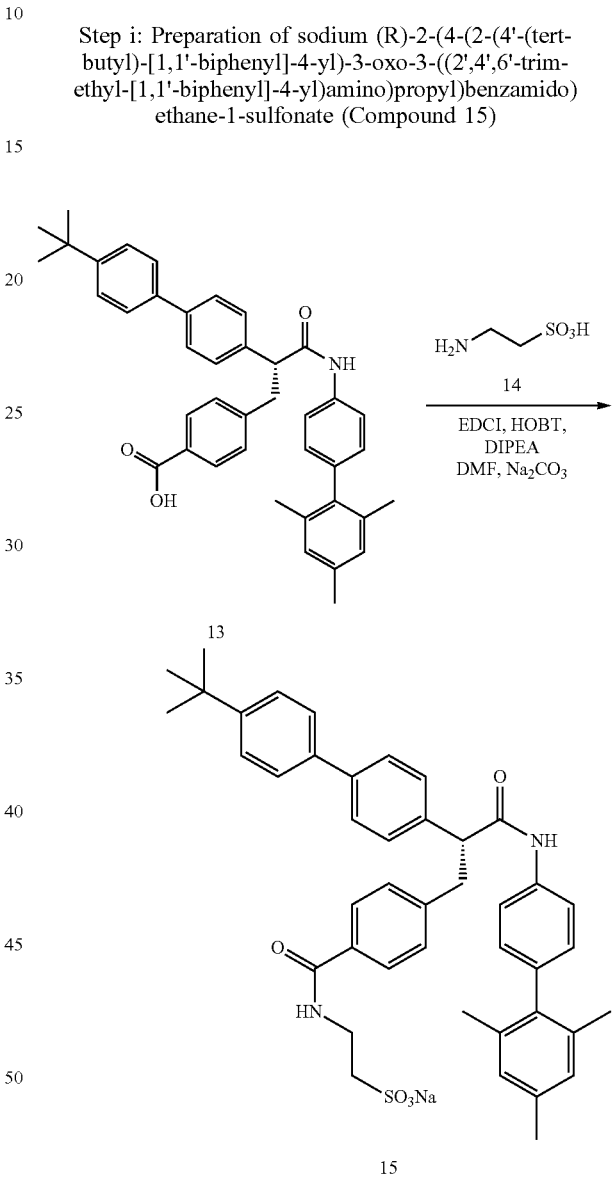

To a reactor were added (R)-4-(2-(4'-(tert-butyl)-[1,1'-biphenyl]-4-yl)-3-oxo-3-((2',4',6'-trimethyl-[1,1'-biphenyl]-4-yl)amino)propyl)benzoic acid (intermediate 13, 12.0 Kg, 1.0×), DMF (58 Kg, 4.7-4.8×), HOBt (4.80 Kg, 0.38-0.40×), taurine (3.95 Kg, 0.31-0.33×), and DIPEA (13.0 Kg, 1.0-1.1×). The mixture was stirred at 10-20° C. for 10-20 min. To this mixture was added EDCI (5.00 Kg, 0.39-0.43×) at 10-20° C. The mixture was stirred at 15-25° C. for 18-24 h. HPLC showed that the ratio of intermediate 13 and compound 15 is about 0.01%. Then HCl aqueous solution (72 Kg, 1N, 6-7×) was added into the reactor at 5-10° C., followed by 2-Me-THF (100 Kg, 6.6-8.6×) and process water (30 Kg, 1.0-6.0x). The mixture was stirred for 20-30 min. The organic layer was separated. The aqueous phase was extracted with 2-Me-THF (101 Kg, 5.0-9.0x) once. The combined organic phase was washed with HCl aqueous solution (1N, 6x-7x) twice. Organic phase was added into the reactor and concentrated to 10-12x. The temperature was adjusted to 5-20° C. NaOMe in EtOH solution (44 Kg, 10%, 2.0-8.0x) was added to the reactor slowly to adjust pH to 8.0-9.0. Process water (24 Kg, 1.0-2.0x) was added to the reactor. The mixture was concentrated to 4x-6x. The reactor was cooled to 5-20° C. EtOH (120 Kg, 7.9-10.0x) was added and the mixture was concentrated to 5x-10x. EtOH (99 Kg, 7.9-10.0x) was added the mixture was concentrated to 5x-10x. The mixture was cooled to 0-10° C. and stirred for 1-3 h. The solid was filtered via centrifuge (purity check: 96.6%). The filtered cake was transferred back to the reactor. EtOH (131 Kg, 8.0x-13.0x) was added, followed by process water (12 Kg, 0.7x-1.0x). The temperature was adjusted to 65-80° C. The mixture was stirred at 65-80° C. for 1-2 h. Then it was cooled to 0-5° C. and the solid was filtered via centrifuge (purity check: 99.0%). The filter cake was transferred to another reactor. To this reactor were added EtOH (96 Kg, 7.7-8.3x), Process water (12.2 Kg, 1.00-1.03x), and EtOAc (27 Kg, 2.1-2.3x). The mixture was stirred at 65-80° C. for 0.5-1 h. The mixture was cooled to 0-10° C. and filtered via centrifuge (chiral purity: 88%). The filter cake was transferred back to the reactor and the process above was repeated twice to provide a filter cake with chiral purity: 98.7%. The composite sample was taken from the wet cake, dried at 45-55° C. for 3-10 h, then was tested for residual starting materials. Starting material 14 and intermediate 13 were not detected. The wet cake (10.67 Kg) was transferred into drum and store it at 2-8° C.

Step j: Recrystallization of sodium (R)-2-(4-(2-(4'-(tert-butyl)-[1,1'-biphenyl]-4-yl)-3-oxo-3-((2',4',6'-trimethyl-[1,1'-biphenyl]-4-yl)amino)propyl)benzamido) ethane-1-sulfonate

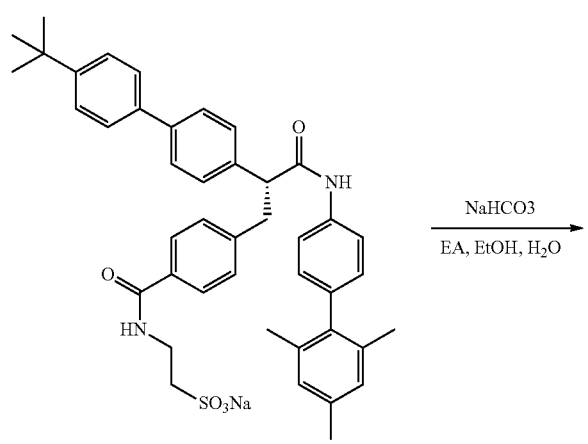

15

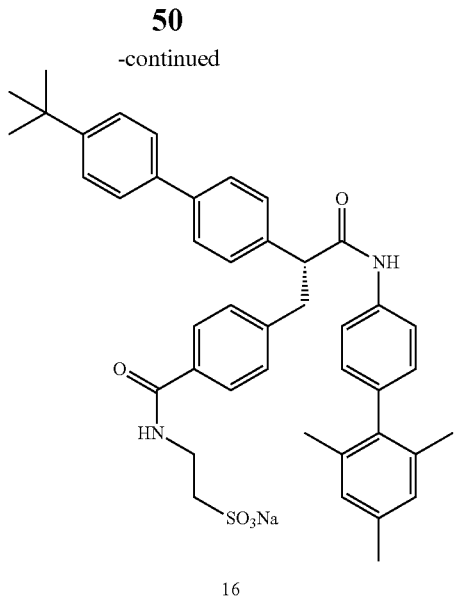

16

A reactor was purged with $N_2$. To this reactor were added compound 15 (10.2 Kg, 1.0x), ethanol (102 Kg, 8.0-10.0x), ethyl acetate (27 Kg, 2.0-2.6x), and water (19 Kg, 1.5-1.9x). The mixture was heated to 60-80° C. and stirred at that temperature for 1-3 hours. The solution was transferred to another reactor by warm filtration. The solution was concentrated to 9.0-11.0x at 70-90° C. at normal pressure. To the solution was added a solution of $NaHCO_3$ (0.10 Kg, 0.01x) in purified water (1.25 Kg, 0.12x) and EtOH (6.0 Kg, 0.6x) at 70-80° C., followed by EtOH (50 Kg, 3-5x). The solution was concentrated at normal pressure to 9.0-11.0x at 70-90° C. the solution was cooled to 65-80° C. and a sample was taken to test (KF=6.9%). The mixture then was cooled to 10-15° C. over a period of 5-7 h at a rate of 2° C. every 10 min. The resulting white slurry was stirred at 10-15° C. for 10-16 h. The solid was filtered via centrifuge and washed with Ethanol (22 Kg, 1.0-3.0x). It was dried under reduced pressure at 45-55° C. for 24-30 h and then sieved to afford desired product (6.90 Kg).

XRPD, TGA, and DSC Analysis for Kilogram Batches.

TGA/DSC analysis was performed using a Mettler-Toledo TGA/DSC3+ analyzer. Temperature and enthalpy adjustments were performed using indium, tin, and zinc, and then verified with indium. The balance was verified with calcium oxalate. The sample was placed in an open aluminum pan. The pan was hermetically sealed, the lid pierced, then inserted into the TG furnace. A weighed aluminum pan configured as the sample pan was placed on the reference platform. The furnace was heated under nitrogen at 50 mL/min. The sample was run from 25 to 350° C. at 10° C./min.

The crystalline Polymorph Form A obtained by the method above was analyzed by X-ray diffraction, TGA, and DSC with FIG. 31 depicting an XRPD pattern for unmilled crystalline polymorph Form A, FIG. 32 depicting an XRPD pattern for milled crystalline polymorph Form A, FIG. 33 depicting a TGA pattern for crystalline polymorph Form A, and FIG. 34 depicting a DSC pattern for crystalline polymorph Form A.

Example 2

Preparation of sodium (R)-2-(4-(2-(4'-(tert-butyl)-[1,1'-biphenyl]-4-yl)-3-oxo-3-((2',4',6'-trimethyl-[1,1'-biphenyl]-4-yl)amino)propyl)benzamido)ethanesulfonic acid A sodium salt of compound of Formula III (compound 15) was synthesized according to the following reaction scheme:

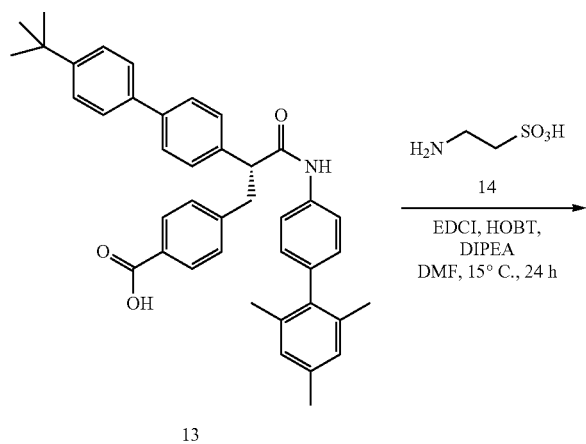

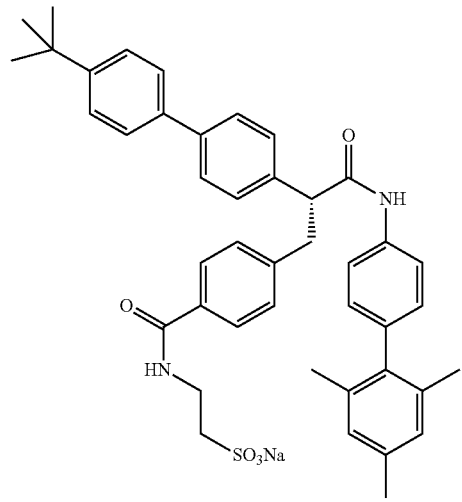

(R)-4-(2-(4'-(tert-butyl)-[1,1'-biphenyl]-4-yl)-3-oxo-3-((2',4',6'-trimethyl-[1,1'-biphenyl]-4-yl)amino)propyl)benzoic acid (intermediate 13, 1.0×) was charged into a reactor. DMF (4.75×) was charged into the reactor. HOBt (0.39×) was charged into the reactor. Taurine (reagent 14, 0.32×) was charged into the reactor. DIEA (1.09×) was added into the reactor at 10-20° C. The mixture was stirred in the reactor at 10-20° C. for 10 min. EDCI (0.39×) was charged into the reactor at 10-20° C. Then the mixture was stirred in the reactor at 15-25° C. for 18-24 hr. The reaction is monitored by HPLC until the ratio of intermediate 13 and compound 15 is less than 0.1%. Then 1N HCl (6×-7×) was added into the reaction at 5-10° C. 2-Me-THF (6.6×-8.6×) was added into the reactor. Water (4×-6×) was added into the reactor. The mixture was stirred in the reactor for 20~30 min. The organic phase was separated. The aqueous phase was extracted with 2-Me-THF (8×-9×) once. The organic layers were combined and washed with 1N HCl (6×-7×) twice. The organic layer was filtered through (3×) silica gel twice. New batch silica gel (3×) was used to filter the organic layer. The organic phase was added into the reactor and concentrated to 10-12×. 10% NaOMe solution in EtOH (1×-10×) was added to the reactor. Water (1×-2×) was added to the reactor. The resulting mixture in the reactor was concentrated to 4×-6× and was cooled to 5-20° C. EtOH (8×-10×) was added to the reactor. The mixture in the reactor was concentrated to 10×-12×. EtOH (8×-10×) was added to the reactor. Then the mixture was concentrated to 10×-12×. The mixture was cooled to 0-10° C. and stirred for 1-3 hours. Slurry appeared in the reactor and was filtered. The filter cake was washed with EtOH (2×-4×). The purity of the filter cake was more than 98.5%. Otherwise, the filter cake was suspended in 92% aqueous EtOH (9×-13×) at 65-80° C. and, if not more than 98.5% pure, the process above can be repeated until the purity meets the requirement. The filter cake was used in the next step directly. Purity: 98.0%.

Example 3

Crystallization of Sodium (R)-2-(4-(2-(4'-(tert-butyl)-[1,1'-biphenyl]-4-yl)-3-oxo-3-((2',4',6'-trimethyl-[1,1'-biphenyl]-4-yl)amino)propyl)benzamido)ethanesulfonic acid A 5-L round bottom flask (R1) was equipped with a mechanical stirrer, an addition funnel with a nitrogen inlet, a condenser, and a thermometer. R1 was purged with nitrogen. Then sodium (R)-2-(4-(2-(4'-(tert-butyl)-[1,1'-biphenyl]-4-yl)-3-oxo-3-((2',4',6'-trimethyl-[1,1'-biphenyl]-4-yl)amino)propyl)benzamido)ethanesulfonic acid (compound 15, 230 g, 1.0×) was charged into R1. To R1 was added ethanol (1820 g, 7.91×, 10.0 vol), followed by ethyl acetate (450 g, 2.0×, 2.17 vol) and water (400 g, 1.74×, 1.74 vol). The mixture was heated to 60-70° C. and stirred at 60-70° C. for 0.5 hour. The suspension was filtered to another 5-L round bottom flask (R2) at hot. The yellow solution was heated to 70-90° C. and distilled to 2000 mL at atmosphere pressure (inert temperature: 70-90° C.). To this solution was added NaOH (0.55 g, 0.0024×) in ethanol (78 g, 0.34×) and water (10 g, 0.044×) by drop wise at 70-80° C. Then the mixture was cooled to 10-15° C. over 5 h at a rate of 1° C. every 5-10 min. The mixture was stirred at 10-15° C. for 20 h, and then the mixture was filtered under nitrogen. The residue of compound 1-3 in mother liquor was checked via HPLC. R2 was rinsed with ethanol (100 g, 0.43×). The filter cake was washed with rinsed ethanol. A sample was taken for HPLC purity test and ee purity test. The wet cake was dried under vacuum at 50-55° C. over 10 h to provide Polymorph Form A.

The Polymorph Form A of sodium (R)-2-(4-(2-(4'-(tert-butyl)-[1,1'-biphenyl]-4-yl)-3-oxo-3-((2',4',6'-trimethyl-[1,1'-biphenyl]-4-yl)amino)propyl)benzamido)ethanesulfonic acid was analyzed by X-ray diffraction, with FIG. 1 depicting an X-ray diffraction pattern. Table 1 shows analytical results of Polymorph Form A.

Details of XRPD method used in the tests are summarized below:

X-ray Generator: Cu, kα1, (λ=1.54056 Å)
Tube Voltage: 40 kV, Tube Current: 40 mA
DivSlit: 1 deg.
DivH.L.Slit: 10 mm
SctSlit: 1 deg.
RecSlit: 0.15 mm
Monochromator: Fixed Monochromator
Scanning Scope: 4-40 deg.
Scanning Step: 10 deg/min Details of DSC method used in the tests are summarized below:

25-400° C. 10° C./min
Dt 1.00 s
Synchronization enabled
Reacting gas: $N_2$: 50 mL/min
Protective gas: $N_2$: 80 mL/min

TABLE 1

Analysis of Polymorph Form A

| Testing Item | Specification Limit | Result |
| --- | --- | --- |
| Color and appearance | Report Result | White powder |
| Identification by $^1$HNMR | Conforms to reference spectrum | Conforms |
| Water Content (KF) | Report Result | 2.1% |
| Purity (HPLC) | NLT 98.0% area | 99.8% |
| Impurities (HPLC) | | |
| Individual impurity | NMT 1.00% area | RRT0.46(Impurity A): 0.08% |
| | | RRT0.64(Impurity B): 0.12% |
| | | RRT1.26(C10080915-F): 0.05% |
| Total impurities | NMT 2.0% area | 0.25% |
| Assay (HPLC) | NLT 97.0% w/w | 98.8% |
| e.e. % (HPLC) | NLT 98.0% peak area | 99.9% |
| Trace metals | | |
| Sodium | Report Result | 29422 ppm |
| Pd | NMT 10 ppm | <10 ppm |
| XRPD | Report Results | 2-Theta: 4.663, 6.961, 9.278, 11.040, 11.380, 11.919, 13.762, 21.421, 23.800 |
| Residual Solvents (GC) | | |
| Ethanol | NMT 0.5% w/w | 0.4% |
| Ethyl acetate | NMT 0.5% w/w | N.D. (<0.005%) |
| 2-Methyltetrahydrofuran | NMT 0.06% w/w | N.D. (<0.0025%) |
| Dichloromethane | NMT 0.06% w/w | N.D. (<0.01%) |
| n-Heptane | NMT 0.5% w/w | N.D. (<0.001%) |
| N,N-dimethyl formamide | NMT 0.088% w/w | N.D. (<0.005%) |
| Residual on Ignition | Report Result | 9.6% |
| Heavy Metals | NMT 20 ppm | <20 ppm |
| PSD | Report Results | $D_{10}$: 4.39 um |
| | | $D_{50}$: 16.10 um |
| | | $D_{90}$: 43.18 um |
| DSC | Report Results | Peak 1: |
| | | Onset 27.99° C. |
| | | Peak: 75.08° C. |
| | | Endset: 91.51° C. |
| | | Peak 2: |
| | | Onset: 200.83° C. |
| | | Peak: 207.40° C. |
| | | Endset: 210.14° C. |
| | | Peak 3 |
| | | Onset: 225.26° C. |
| | | Peak: 233.42° C. |
| | | Endset: 236.57° C. |
| | | Peak 4: |
| | | Onset: 240.66° C. |
| | | Peak: 245.03° C. |
| | | Endset: 248.07° C. |

Example 4

Stability Data of Polymorph Form A

Stability data of Polymorph Form A are summarized in Tables 2-4.

TABLE 2

Accelerated Stability Data
Name: Polymorph Form A  Lot Size: 1260 g
Container/Closure: Double LDPE bag Fiberboard drum
Storage Condition: 40° C./75% RH

| Test Category | Specification Limit | | Time (Months) | | | | |
|---|---|---|---|---|---|---|---|
| | | | 0 | 1 | 2 | 3 | 6 |
| Appearance | Report results | | White powder | White powder | White powder | White powder | White powder |
| Assay (anhydrous w/w %) | ≥97.0 | | 101.3 | 102.0 | 103.4 | 103.4 | 103.7 |
| Purity (area %) | ≥98.0 | | 99.8 | 99.8 | 99.7 | 99.8 | 99.8 |
| Individual related substance (area %, w/w) | ≤1.0 | RRT 0.46 | 0.08 | 0.08 | 0.08 | 0.08 | 0.08 |
| | | 0.64 | 0.12 | 0.11 | 0.12 | 0.11 | 0.12 |
| | | 1.26 | 0.05 | 0.05 | 0.06 | 0.05 | 0.05 |
| Total related substances (area %, w/w) | ≤2.0 | | 0.25 | 0.24 | 0.26 | 0.24 | 0.25 |
| Chiral purity (area %) | ≥98.0 | | 99.9 | 99.8 | 99.8 | 100.0 | 100.0 |
| Water content (%) | Report results | | 2.1 | 8.1 | 9.8 | 10.0 | 10.0 |
| XRPD | Report results | | Recorded | NA | NA | Same form | Same form |

LDPE = Low-density polyethylene.
NA = Not applicable.
RH = Relative humidity.
RRT = Relative retention time.
XRPD = X-ray powder diffraction.
w/w = Weight per weight.
*Denotes change

TABLE 3

Long Term Stability Data
Name: Polymorph Form A  Lot Size: 1260 g
Container/Closure: Double-LDPE bag Fiberboard Drum
Storage Condition: 25° C./60% RH

| * Test Category | Specification Limit | | Time (Months) | | | | | | | |
|---|---|---|---|---|---|---|---|---|---|---|
| | | | 0 | 3 | 6 | 9 | 12 | 18 | 24 | * 36 |
| Appearance | Report results | | White powder | White powder | White powder | White powder | White powder | White powder | White powder | White powder |
| Assay (anhydrous w/w %) | ≥97.0 | | 101.3 | 102.5 | 101.1 | 101.1 | 101.0 | 100.9 | 101.6 | 101.4 |
| Purity (% area) | ≥98.0 | | 99.8 | 99.8 | 99.8 | 99.8 | 99.8 | 99.7 | 99.7 | 99.7 |
| * Individual related substance (area %, w/w) | ≤1.0 | RRT 0.31 | | | | | | | | 0.05 |
| | | 0.46 | 0.08 | 0.08 | 0.08 | 0.08 | 0.08 | 0.08 | 0.08 | 0.08 |
| | | 0.64 | 0.12 | 0.12 | 0.11 | 0.12 | 0.11 | 0.12 | 0.12 | 0.12 |
| | | 1.20 | 0.05 | 0.05 | 0.05 | 0.05 | 0.05 | 0.06 | 0.07 | 0.05 |
| Total related substances | ≤2.0 | | 0.25 | 0.25 | 0.24 | 0.25 | 0.24 | 0.26 | 0.27 | 0.30 |
| Chiral purity (area %) | ≥98.0 | | 99.9 | 99.8 | 99.8 | 99.6 | 99.4 | 99.5 | 100.0 | 99.8 |
| Water content (%) | Report results | | 2.1 | 6.1 | 6.5 | 6.7 | 7.0 | 6.9 | 7.4 | 7.5 |
| XRPD | Report results | | Recorded | NA | Same form | NA | Same form | NA | Same form | Same form |

LDPE = Low-density polyethylene.
NA = Not applicable.
RH = Relative humidity.
RRT = Relative retention time.
XRPD = X-ray powder diffraction.
w/w = Weight per weight.
* Denotes change.

TABLE 4

Photostability Data
Name: Polymorph Form A　　　　　　　　　　Lot Size: 1260 g
Container/Closure: Open
Storage Condition: 5000 Lux

| Test Category | Specification Limit | Time (weeks) | | |
|---|---|---|---|---|
| | | 0 | 1 | 2 |
| Appearance | Report results | White powder | White powder | White powder |
| Purity (area %) | ≥98.0 | 99.8 | 99.2 | 99.2 |
| Total related substances (area %, w/w) | ≤2.0 | 0.25 | 0.25 | 0.25 |
| XRPD | Report results | Recorded | Same form | Same form |

LDPE = Low-density polyethylene.
NA = Not applicable.
RH = Relative humidity.
RRT = Relative retention time.
XRPD = X-ray powder diffraction.
w/w = Weight per weight.

Example 5

Polymorph Form A Stability Analysis and Conclusions

Polymorph Form A was manufactured under Good Manufacturing Practices (GMP)-compliant conditions at a scale of 1.26 kg. The container closure for the batch consisted of double-lined low density polyethylene bags placed inside fiberboard drums, and the batch was on ICH stability under storage conditions of 25° C./60% relative humidity (RH) and 40° C./75% RH. The stability schedule is provided in Table 5. Long-term stability data through the 36-month interval and accelerated stability data through the 6-month interval are shown in Tables 2 and 3.

TABLE 5

Stability Protocol Lot PT-C10080915-GF12001

| Storage Condition | Test Interval (Months) | | | | | | | | | |
|---|---|---|---|---|---|---|---|---|---|---|
| | 0 | 1 | 2 | 3 | 6 | 9 | 12 | 18 | 24 | 36 |
| Long-term (25° C. ± 2° C./ 60% ± 5% RH) | C | | | C | P | P | C | P | C | C |
| Accelerated (40° C. ± 2° C./ 75% ± 5% RH) | C | P | P | C | C | | | | | |

C = appearance, assay (high-performance liquid chromatography [HPLC]), chiral purity (chiral HPLC), individual and total related substances (HPLC), water content, and X-ray powder diffraction (XRPD) pattern;
P = appearance, assay (HPLC), chiral purity (chiral HPLC), individual and total related substances (HPLC), and water content;
RH = relative humidity.

Stability samples were tested according to the protocol (Table 5) and to the same specification as the drug substance. The available stability data for samples stored at 25° C./60% RH and 40° C./75% RH are summarized.

No significant changes in assay value, total related substances, physical description, or solid state form (based on XRPD pattern) were for the drug substance stored at 25° C./60% RH and 40° C./75% RH. Total related substances have remained constant at around 0.25%, and no new impurities were detected above the limit of quantitation (LOQ) of 0.05%. The anhydrous assay value remained constant under the long-term condition through the 36-month interval at around 101% (value at release) after correction for absorption of additional moisture. The water content increased from 2.1% to 7.5% on long-term stability and appears to have stabilized at a level of approximately 10% at 40° C./75% RH after the 2-month interval, which is consistent with the hygroscopic nature of the drug substance.

Photostability

Photostability testing was conducted on Polymorph Form A at 1- and 2-week intervals under light conditions of 5000 lux with the sample held at room temperature. The samples were tested for appearance, purity (HPLC), total related substances (TRS), and XRPD. The data are summarized in Table 4. The only change observed in the photostability samples was a decrease in purity of 0.6% at the 1-week interval.

No significant changes in assay value, total related substances, physical description, or XRPD pattern were observed for the drug substance under light condition (5000 lux) for 2 weeks.

Stability Conclusion

Stability data for Polymorph Form A have met the specifications for the drug substance and for the duration of the completed phase I clinical trial.

Example 6

Preformulation of Polymorph Form A

1. Introduction

The objective of this preformulation study includes aqueous solubility, solid stability, pKa, Log P/D, intrinsic dissolution rate (IDR) and hygroscopicity of Polymorph Form A.

2. Material & Instruments 2.1 Compound: Polymorph Form A
2.2 Reagents: Acetonitrile (ACN), HPLC grade, Merck, Lot No. IH11F61419; Tetrahydrofuran (THF): AR grade, SCRC, Lot No. T20110928; Dimethyl sulfoxide (DMSO): HPLC grade, Merck, Lot No. SBOS600084; Methanol (MeOH): HPLC grade, Merck, Lot No. SC2SF62167; 1,4-Dioxane: AR grade, Jiangsu Qiangsheng Gongneng Chemical Co., Ltd. (JQGCC), Lot No. 20120201.

pH 4.0 phthalate buffer (USP): to a 100 mL volumetric flask was sequentially added with 0.2 M aq. potassium biphthalate ($C_8H_5KO_4$) solution (25 mL) and 0.2 M hydrochloric acid (HCl) solution (0.05 mL). The resulting solution was diluted with distilled water to reach a total volume of 100 mL.

pH 6.8 phosphate buffer (USP): to a 100 mL volumetric flask was sequentially added 0.2 M monobasic potassium phosphate ($KH_2PO_4$) solution (25 mL) and 0.2 M aq. sodium hydroxide (NaOH) solution (11.2 mL). The resulting solution was diluted with distilled water to reach a total volume of 100 mL.

pH 7.4 phosphate buffer (USP): to a 100 mL volumetric flask was sequentially added 0.2 M monobasic potassium phosphate (KH2PO4) solution (25 mL) and 0.2 M aq. sodium hydroxide (NaOH) solution (19.55 mL). The resulting solution was diluted with distilled water to reach a total volume of 100 mL.

pH 10.0 borate buffer (USP): to a 100 mL volumetric flask was sequentially added 0.2 M aq. Boric acid (H3BO3) and potassium chloride solution (KCl) (25 mL) and 0.2 M aq. sodium hydroxide (NaOH) solution (21.85 mL). The resulting solution was diluted with distilled water to reach a total volume of 100 mL.

SGF (pH 1.2): 2.0 g sodium chloride (NaCl) was added into distilled water (1000 mL) and the resulting solution was adjusted to pH 1.2 by adding 10 N aq. hydrochloric acid (HCl) solution.

FaSSIF (pH 6.5): Step 1 (preparation of blank FaSSIF): 1.74 g of sodium hydroxide (pellets), 19.77 g of sodium dihydrogen phosphate monohydrate or 17.19 g of anhydrous sodium dihydrogen phosphate, and 30.93 g of sodium chloride were dissolved in 5 L of purified water. The pH was adjusted to exactly 6.5 using 1 N sodium hydroxide or 1 N hydrochloric acid. Step 2 (preparation of FaSSIF): 3.3 g of sodium taurocholate was dissolved in 500 mL blank FaSSIF. 11.8 mL of a solution containing 100 mg/mL lecithin was added to methylene chloride, forming an emulsion. The methylene chloride was eliminated under vacuum at about 40° C. The vacuum was drawn for fifteen minutes at 250 mbar, followed by 15 minutes at 100 mbar. This resulted in a clear, micellar solution, having no perceptible odor of methylene chloride. After cooling to room temperature, the volume was adjusted to 2 L with blank FaSSIF.

FeSSIF (pH 5.0): Step 1 (preparation of blank FeSSIF): 20.2 g of sodium hydroxide (pellets), 43.25 g of glacial acetic acid, and 59.37 g of sodium chloride was dissolved in 5 L of purified water. The pH was adjusted to exactly 5.0 using 1 N sodium hydroxide or 1 N hydrochloric acid. Step 2 (preparation of FeSSIF): 16.5 g of sodium taurocholate was dissolved in 500 mL of blank FeSSIF. 59.08 mL of a solution containing 100 mg/mL lecithin was added to methylene chloride, forming an emulsion. The methylene chloride was eliminated under vacuum at about 40° C. A vacuum was drawn for fifteen minutes at 250 mbar, followed by 15 minutes at 100 mbar. This resulted in a clear to slightly hazy, micellar solution having no perceptible odor of methylene chloride. After cooling to room temperature, the volume was adjusted to 2 L with blank FeSSIF.

2.3 Instruments

Sartorius CP 225D Balance; Mettler-Toledo MX5 Balance; Rigaku D/MAX 2200 X-ray powder diffractometer; DVS Advantage 1; Milli-Q Direct 8 Water Purification Equipment; Agilent 1260 HPLC; Mettler Toledo SevenMulti pH meter; Sirius T3.

3. XRPD, Hygroscopicity and HPLC Methods
3.1 XRPD method

Details of XRPD method used in the tests are summarized below:

X-ray Generator: Cu, kα1, (λ=1.54056 Å)
Tube Voltage: 40 kV, Tube Current: 40 mA
DivSlit: 1 deg.
DivH.L.Slit: 10 mm
SctSlit: 1 deg.
RecSlit: 0.15 mm
Monochromator: Fixed Monochromator
Scanning Scope: 4-40 deg.
Scanning Step: 10 deg/min 3.2 Hygroscopicity Details of DVS method used in the tests are summarized below:

Test the sorption/desorption profile of testing compound at 25° C. under 0-90% relative humidity.

3.3 HPLC Method

Figure 2:
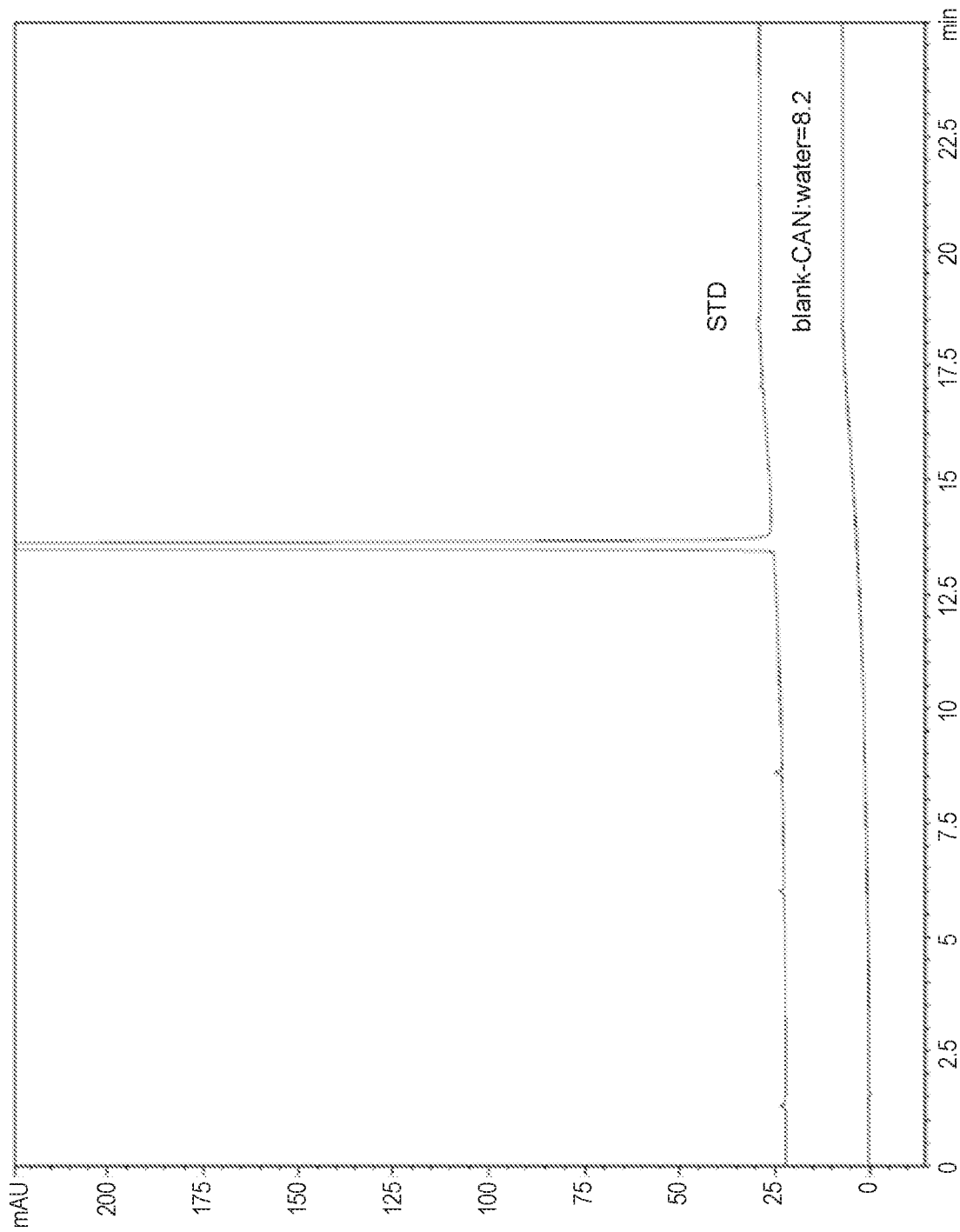
FIG. 2 is an HPLC chromatogram of Polymorph Form A.

The chromatographic conditions for HPLC are summarized in Table 6 below. The typical retention time of Polymorph Form A was 13.5 min. The chromatogram of Polymorph Form A standard solution is shown in FIG. 2.

TABLE 6

| Instrument | Agilent HPLC 1260 | | |
|---|---|---|---|
| Column | Waters XBridge C18, 4.6 * 150 mm, 3.5 μm | | |
| Column Temperature | 30° C. | | |
| Mobile Phase | A: 0.1% TFA in water (v/v) | | |
| | B: 0.1% TFA in acetonitrile (v/v) | | |
| Gradient Program | Time (min) | A % | B % |
| | 0.01 | 60 | 40 |
| | 15.00 | 5 | 95 |
| | 25.00 | 5 | 95 |
| | 25.01 | 60 | 40 |
| Run time | 25 min | | |
| Post Time | 10 min | | |
| Flow Rate | 1.0 mL/min | | |
| Detection Wavelength | 258 nm | | |
| Injection Volume | 5 μL | | |
| Diluent | ACN:water = 80:20 (v/v) | | |

4. Experimental
4.1 Aqueous Solubility
4.1.1 Experiment

The testing media: Water, pH 4.0, 6.8, 7.4, 10.0 USP buffers (50 mM), 0.1N HCl, 0.01N HCl, SGF, FaSSIF, FeSSIF.

About 10 mg of Polymorph Form A was weighed and added to a 1.5 mL vial, and then 1.0 mL of aqueous media was added into the vial. The vial was shaken for 24 hours at 25° C. After equilibration for 24 hours, the mixture was centrifuged at 14000 rpm for 10 mins. The concentration of supernatant was checked by HPLC and the residuals were checked by XRPD. The final pH of supernatant was recorded. Experiments were conducted in duplicate.

4.1.2 Result

Figure 3:
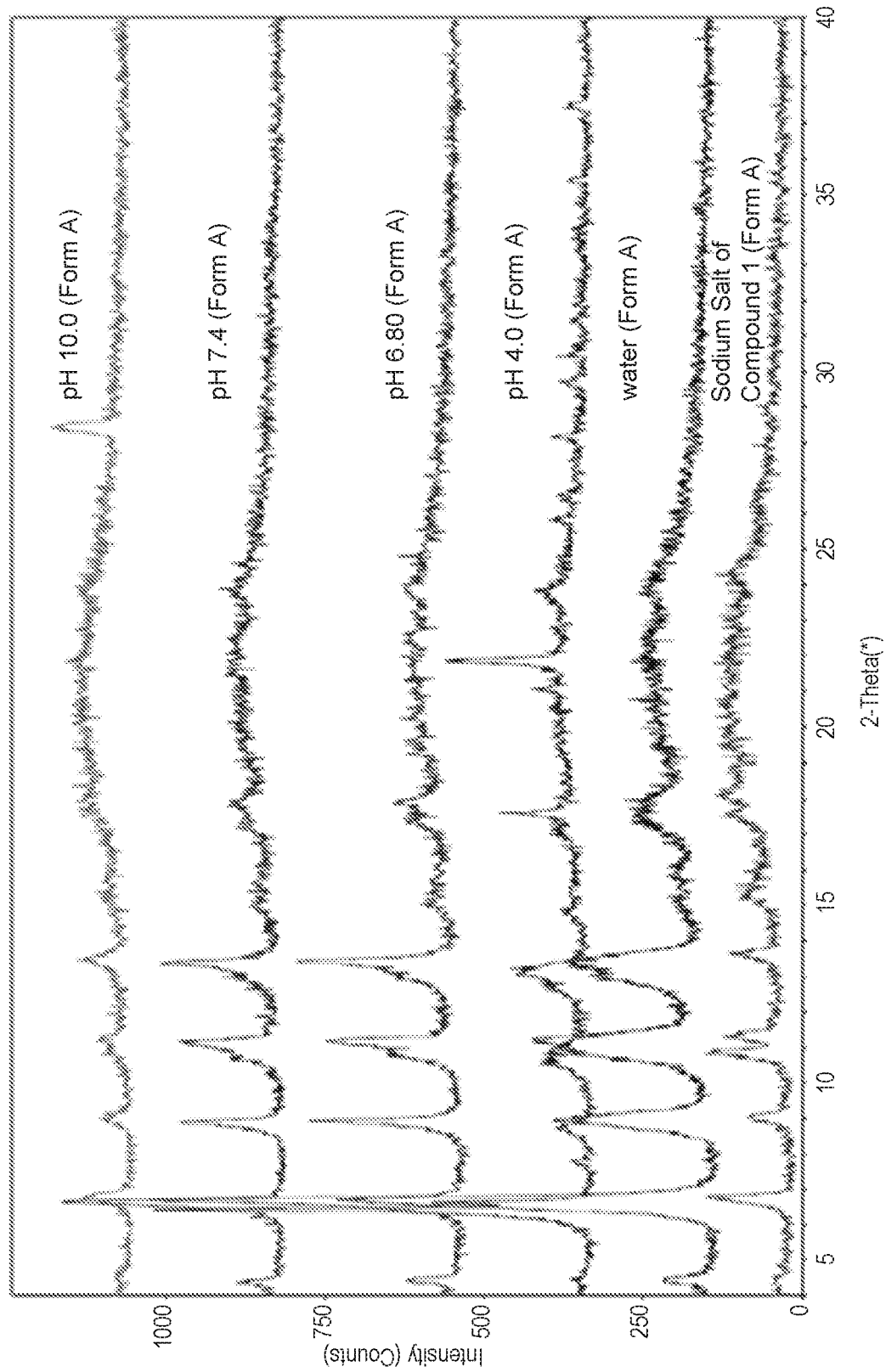
FIG. 3 is an XRPD overlay of residuals in solubility test of Polymorph Form A (part 1).
Figure 4:
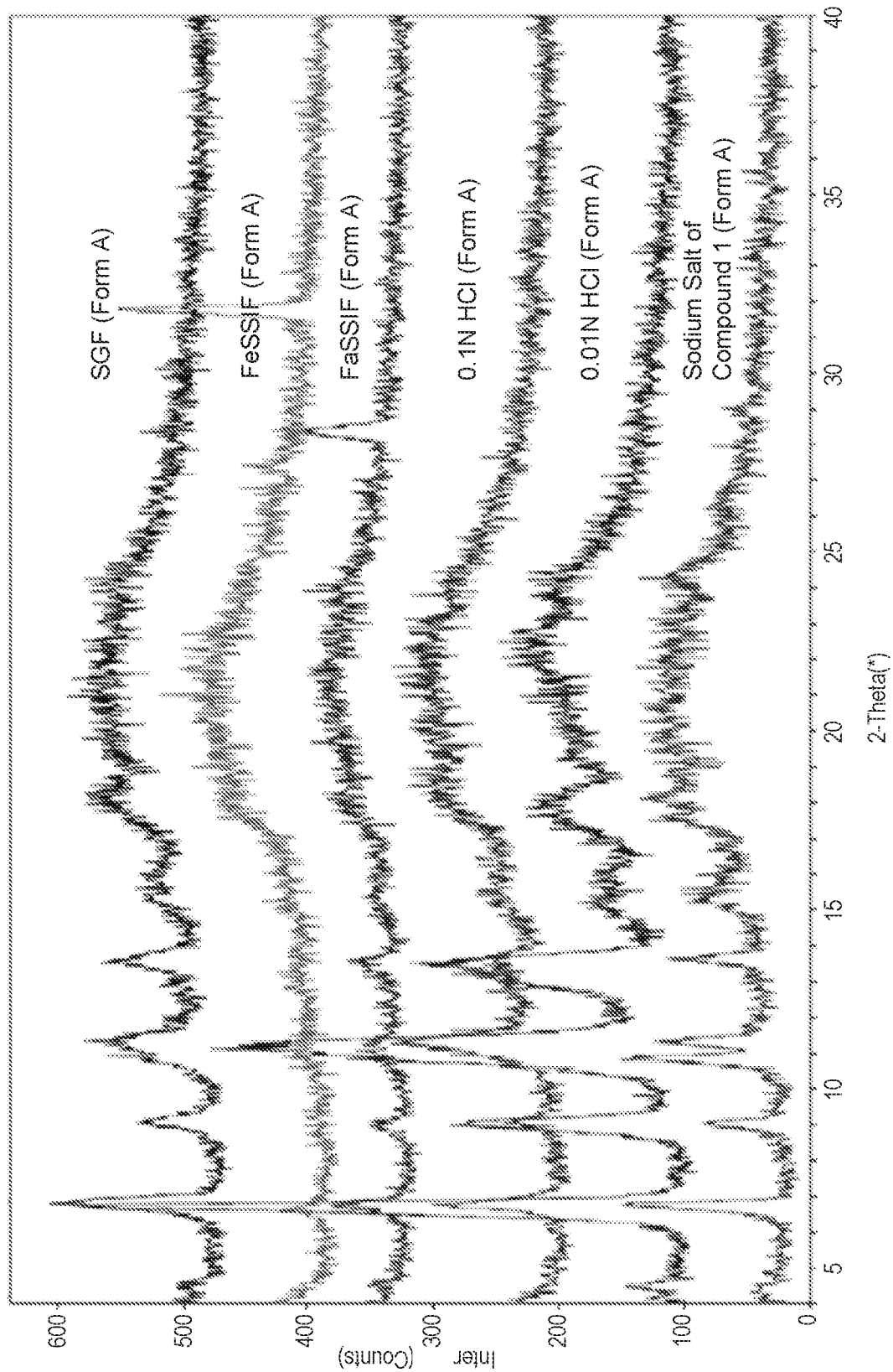
FIG. 4 is an XRPD overlay of residuals in solubility test of Polymorph Form A (part 2).

The results are shown in Table 12 and FIG. 3 to FIG. 4. As per the solubility results, Polymorph Form A was practically insoluble in pH 4.0 buffer, pH 6.8 buffer, pH 7.4 buffer, pH 10.0 buffer, 0.1N HCl, 0.01N HCl and SGF (<0.1 mg/mL), very slightly soluble in water and FaSSIF (>0.1 mg/mL, <1 mg/mL) and slightly soluble in FeSSIF (>1 mg/mL, <10 mg/mL).

For the XRPD results, no new forms were found. The extra peaks at 2θ angles of 21.9° (pH 4.0), 28.4° (pH 10 and FaSSIF) and 31.8° (FeSSIF) were caused by residual inorganic salt used for testing media.

4.2 Solid Stability
4.2.1 Experiment

About 3 mg Polymorph Form A was weighed in glass vials and samples stored under light condition (5000 lx) for 1 week and 2 weeks, separately. Another 20 mg testing compound was weighed in glass vials and the samples stored under light condition for 1 week and 2 weeks, separately. The original compound was stored at −20° C. as the control. The physical appearance, assay, total related substances (TRS) and XRPD pattern were checked at the end of the 1st week and the 2nd week.

4.2.2 Result

Figure 5:
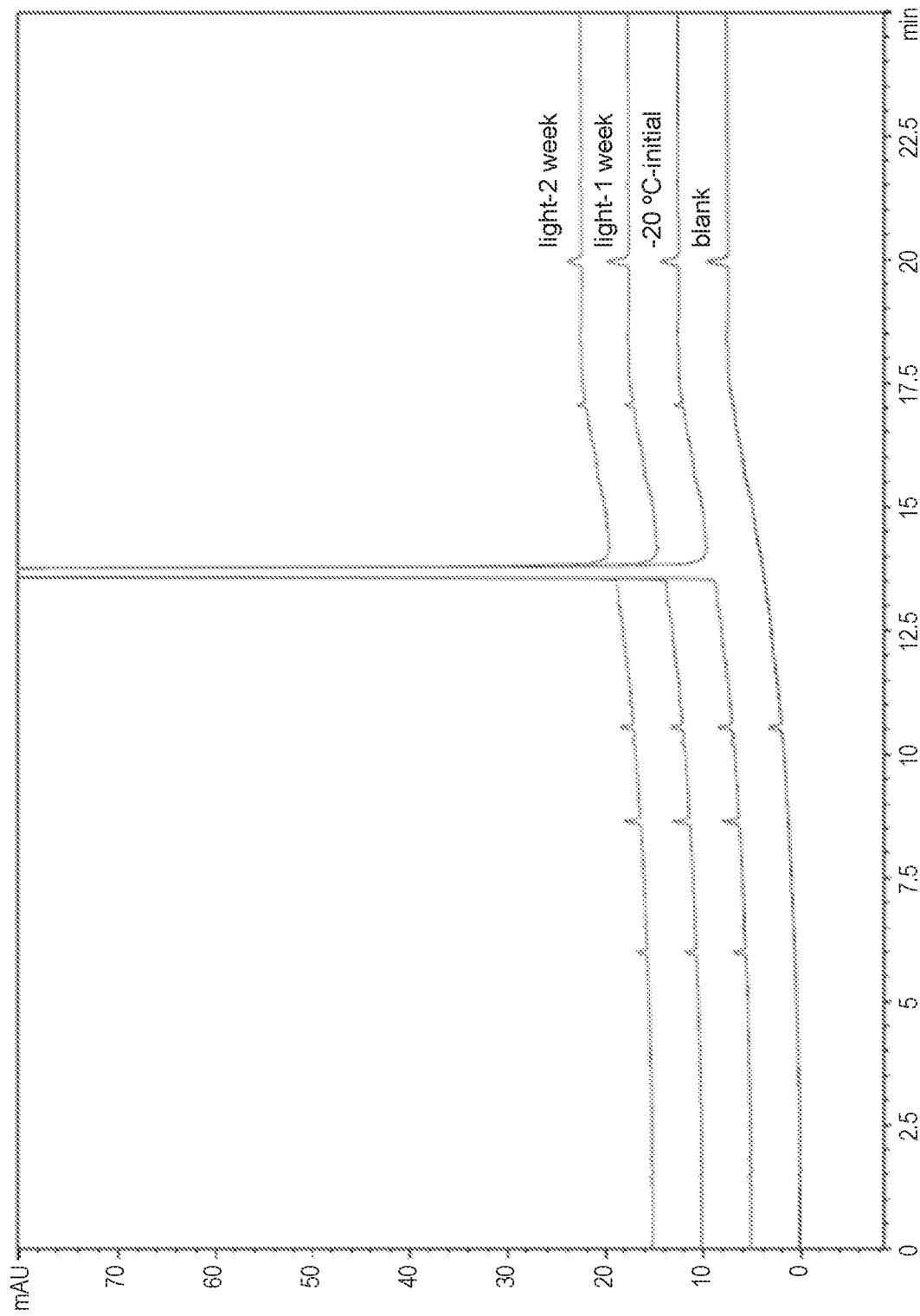
FIG. 5 is an HPLC overlay of solid stability of Polymorph Form A under light for 1 week and 2 weeks.
Figure 6:
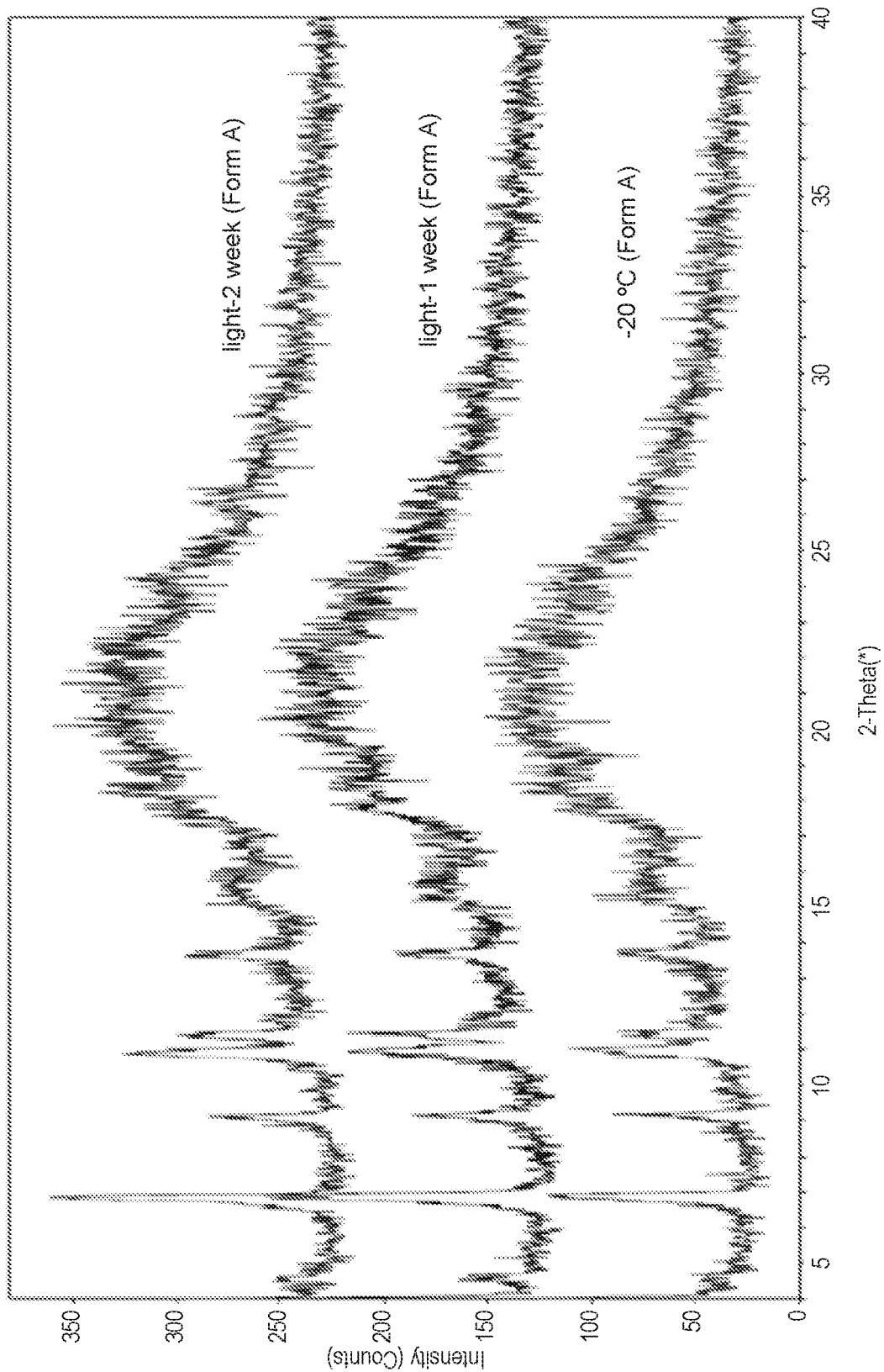
FIG. 6 is an XRPD of solid stability of Polymorph Form A under light for 1 week and 2 weeks.
Figure 7A:
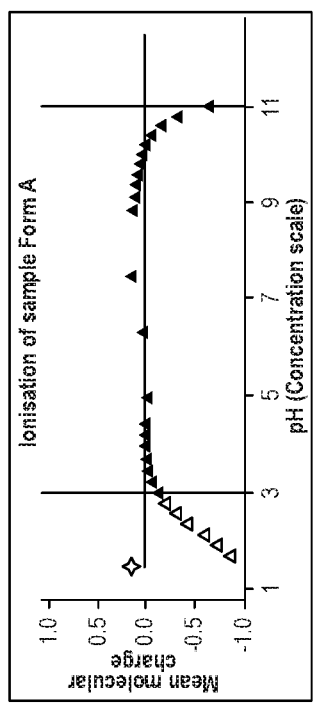
FIG. 7A shows an ionization graph for pH metric determination of Polymorph Form A with 80v % MeOH as initial cosolvent.
Figure 7B:
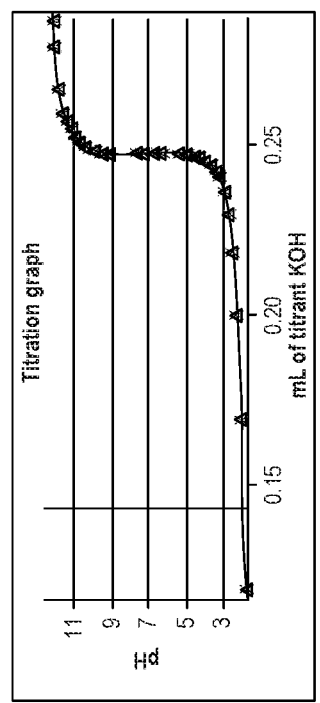
FIG. 7B shows a titration graph for pH metric determination of Polymorph Form A with 80v % MeOH as initial cosolvent.
Figure 8A:
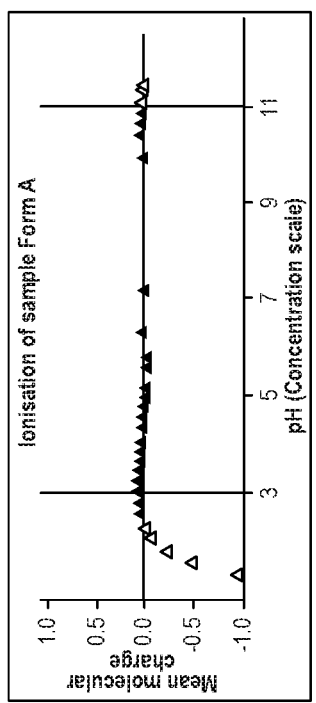
FIG. 8A shows an ionization graph for pH metric determination of Polymorph Form A with 60v % DMSO as initial cosolvent.
Figure 8B:
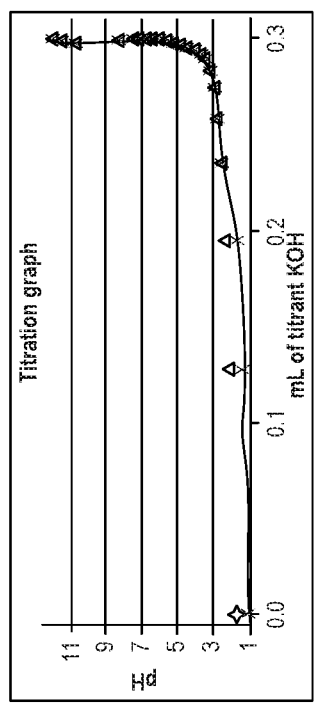
FIG. 8B shows a titration graph for pH metric determination of Polymorph Form A with 60v % DMSO as initial cosolvent.
Figure 9A:
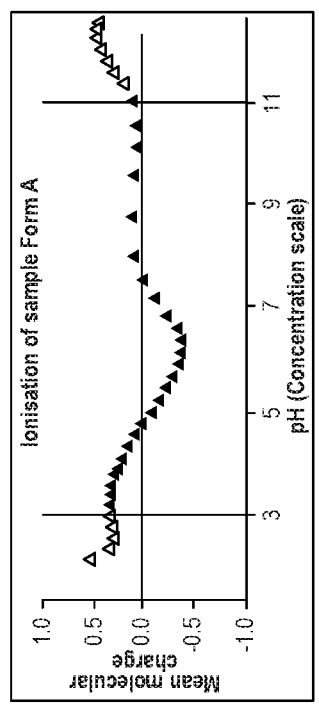
FIG. 9A shows an ionization graph for pH metric determination of Polymorph Form A with 60v % Dioxane as initial cosolvent.
Figure 9B:
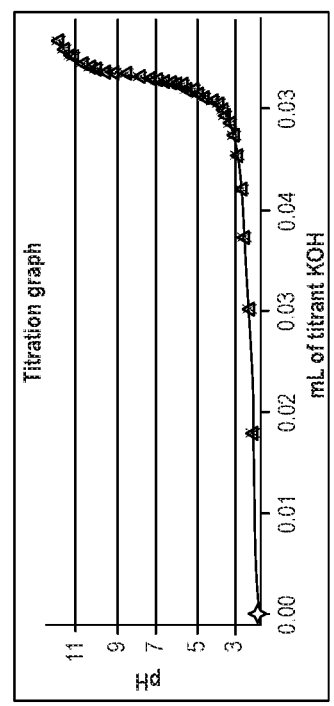
FIG. 9B shows a titration graph for pH metric determination of Polymorph Form A with 60v % Dioxane as initial cosolvent.

The results are listed in Table 13 and FIG. 4 to FIG. 5. No significant increase in TRS % or decrease in recovery % was observed when Polymorph Form A was stored under light conditions after 2 weeks and the XRPD patterns were consistent with the initial form of Polymorph Form A.

4.3 pKa Measurement
4.3.1 Principle of pKa Determination by Sirius T3Dt

There are two methods available on the Sirius T3 for pKa measurement: potentiometric titration and spectroscopic (UV) titration.

4.3.2 Potentiometric titration (pH-metric pKa)

Potentiometric Titration Method is a method which works for any ionicable compound and its standard working range is pH 3.0 to pH 11.0. It is normally restricted to compounds exhibiting sufficient aqueous solubility, typically greater than 0.5 mM. Where this cannot be achieved, the use of organic co-solvents to enhance the solubility is employed.

The pKa values are determined from an examination of the shape of the resultant titration curves and fitting a suitable theoretical model for the compound's ionization behavior onto the titration data. The theoretical model contains components to account for acidic/basic impurities in the sample, non-ideal sample purity and also the presence of dissolved carbonate (in the form of Carbonic Acid).

4.3.3 Spectrophotometric Method (UV-Metric pKa)

Its available pH range is typically between 0.5 and 13.5. A compound concentration of 50 μM is typically used, i.e., ten fold lower than the pH-metric method. Co-solvent determination may also be performed when the assayed compounds remain insoluble under all other conditions.

The pKas are determined by monitoring the change in UV absorbance with pH as the compound undergoes ionization. This information produces a 3D matrix of pH vs. Wavelength vs. Absorbance data. A mathematical technique (Target Factor Analysis) is applied to this matrix to produce molar absorption profiles for the different light absorbing species present in solution, and also a Distribution of Species plot showing how the proportion of each species varies with pH. For the UV method to be successful, the ionisable groups of the test substance must be within 5 bond lengths of a UV chromophore. For compounds that do not meet these criteria, the pH-metric approach must be used to determine the non UV-active pKa's.

When co-solvent solutions had been employed by pH-metric method or UV-metric method, the psKa values are extrapolated to zero percent organic content using the Yasuda-Shedlovsky extrapolation procedure, which yields extrapolated aqueous pKa values and slope information which can be used to ascertain the acidic/basic characteristics of the ionisable groups.

4.3.4 Yasuda-Shedlovsky Extrapolation Procedure

Sirius T3 software fits Yasuda-Shedlovsky data linearly, according to the equation.

$$Yi = C + mXi$$

Where
Yi calculated as $psKa + \log[H2O]$
  psKa represents apparent pKa values of compounds measured in water/co-solvent mixtures
  [H2O] represents co-solvent ratio (as wt. % co-solvent)
Xi calculated as $1/\varepsilon i$.
  $\varepsilon i$ represents dielectric constant of water/co-solvent mixture However, the quality of the fit depends on the quality of the experimental data.

4.3.5 Procedure for pKa Determination
4.3.5.1 pKa Determination by pH Metric Method About 1 mg of Polymorph Form A was weighed into a sample vial, about 1.5 mL of co-solvent (60v % DMSO, 80v % MeOH or 60v % Dioxane) was added into the vial manually, then titrated with acid or base to obtain a psKa value with co-solvent and water, and extrapolated to get aqueous pKa value. Tables 7-9 below and FIGS. 7A-9B provide the results of pKa determination by pH metric method.

TABLE 7

| Titration | Methonal weight % | Direction | Result type | Dielectric constant | [H₂O] | Ionic strength | Temperature |
|---|---|---|---|---|---|---|---|
| Points 61-98 | 37.77% | Up | pH-metric | 61.2 | 31.2M | 0.183M | 27.4° C. |
| Points 29-60 | 50.82% | Up | pH-metric | 55.3 | 23.9M | 0.175M | 27.2° C. |
| Points 4-28 | 65.56% | Up | pH-metric | 48.6 | 16.2M | 0.162M | 26.2° C. |

TABLE 8

| Titration | DMSO weight % | Direction | Result type | Dielectric constant | [H₂O] | Ionic strength | Temperature |
|---|---|---|---|---|---|---|---|
| Points 76-114 | 27.82% | Up | pH-metric | 76.1 | 40.9M | 0.196M | 27.8° C. |
| Point 38-75 | 35.67% | Up | pH-metric | 75.7 | 36.8M | 0.191M | 27.2° C. |
| Point 4-37 | 44.34% | Up | pH-metric | 74.8 | 32.1M | 0.180M | 27.3° C. |

TABLE 9

| Titration | Dioxane weight % | Direction | Result type | Dielectric constant | [H₂O] | Ionic strength | Temperature |
|---|---|---|---|---|---|---|---|
| Points 84-128 | 38.50% | Up | pH-metric | 43.5 | 34.4M | 0.173M | 27.9° C. |
| Point 44-83 | 48.76% | Up | pH-metric | 34.4 | 28.7M | 0.166M | 27.5° C. |
| Point 4-43 | 56.62% | Up | pH-metric | 27.8 | 24.4M | 0.157M | 26.8° C. |

4.3.5.2 pKa Determination by UV Metric Method

About 10 μL sample stock solution of 10 mmol/L in DMSO and 25 μL UV buffer was pipetted into a sample vial, about 1.50 mL of co-solvent of 60v % DMSO was added into the sample vial, and titrated three times with acid or base to extrapolate to get aqueous pKa value. Table 10 below and FIGS. 10A-10F provide the results of pKa determination by the UV metric method.

TABLE 10

| RMSD | 0.025 |
|---|---|
| Chi Squred | 0.0431 |
| PCA calculated number of pKas | 3 |
| Average ionic strength | 0.177M |
| Average temperature | 26.5° C. |
| Analyte concentration range | 28.7 μM to 24.5 μM |
| DSMO weight % | 43.8% |
| Dielectric constant | 75.1 |
| Water concentration | 32.4M |
| Number of pKas source | Predicted |
| Wavelength clipping | 250.0 nm to 450.0 nm |
| pH clipping | 3.003 to 11.002 |

4.3.6 Results

The results of pKa analysis are listed in Table 14 and FIG. 7A to FIG. 10F. Because of the low solubility of sodium salt of Compound 1 and noise interference at low pH, the pKa was not detected by the pH-metric or the UV-metric method between pH 1.0 to pH 11.0.

4.4 Log P/D 4.4.1. Procedure for Log P/D Determination

First, a sample stock solution of Polymorph Form A (100 mmol/L in DMSO) was prepared. 20 μL each of sample DMSO stock solutions was added into 4 ml-vials, then dispensed into 990 μL of 1-octanol-saturated buffer at varied pH and 990 μL of buffer-saturated 1-octanol, vortexed for 3 min and shaken for 1 hr at 880 ppm, then centrifuged at 2500 rpm for 2 min to get rid of bubbles in the solutions. Finally, buffer-layer sample and 1-octanol-layer sample were separated, and then buffer-layer sample and 1-octanol-layer sample was injected into HPLC, integrated the chromatography and calculated the sample concentrations ratio in both buffer and 1-octanol phase. The Log P/D result was obtained by following equation:

$$\text{Log } P/D = \text{Log}_{10} \frac{[\text{Sample concentration in octanol layer}]}{[\text{Sample concentration in buffer layer}]}$$

4.4.2. Log P/D Result

The Log P/D value of Polymorph Form A was acquired by shake-flask method using a HPLC system. Since the concentrations of Polymorph Form A in buffer layer are too low to analyze, based on the comparison of blank and standard solution (S/N=5), 0.05 μmol/L was used in buffer layer to calculate Log D.

The result is shown in Table 15. Polymorph Form A showed lipophilicity with Log D values more than 4.32 in pH range of 1.0 to 11.0.

4.5 Intrinsic Dissolution Rate (IDR)

4.5.1. Experiment

Testing media: water, 0.1N HCl, pH 6.8 USP buffer

About 200 mg Polymorph Form A was weighed into the intrinsic dissolution apparatus (diameter: 0.795 cm) and compressed for 1 minute with 1 ton compression force to make the material compact. The intrinsic dissolution apparatus was slid into the dissolution test chuck and tightened. The shaft in the spindle was adjusted to ensure the exposed surface of the compacted tablet was 3.8 cm from the bottom of the vessel when lowered. The temperature of chamber water was set at 37° C., the shaft rotation at 100 rpm, and the sampling time points at 2, 5, 10, 15, 20, 30, 45, 60, 90 and 120 min. 5 mL of solution was sampled at each time point, and the samples filtered with 0.45 μm filter. The concentration of the filtrates was analyzed by HPLC.

4.5.2. Result

Figure 11:
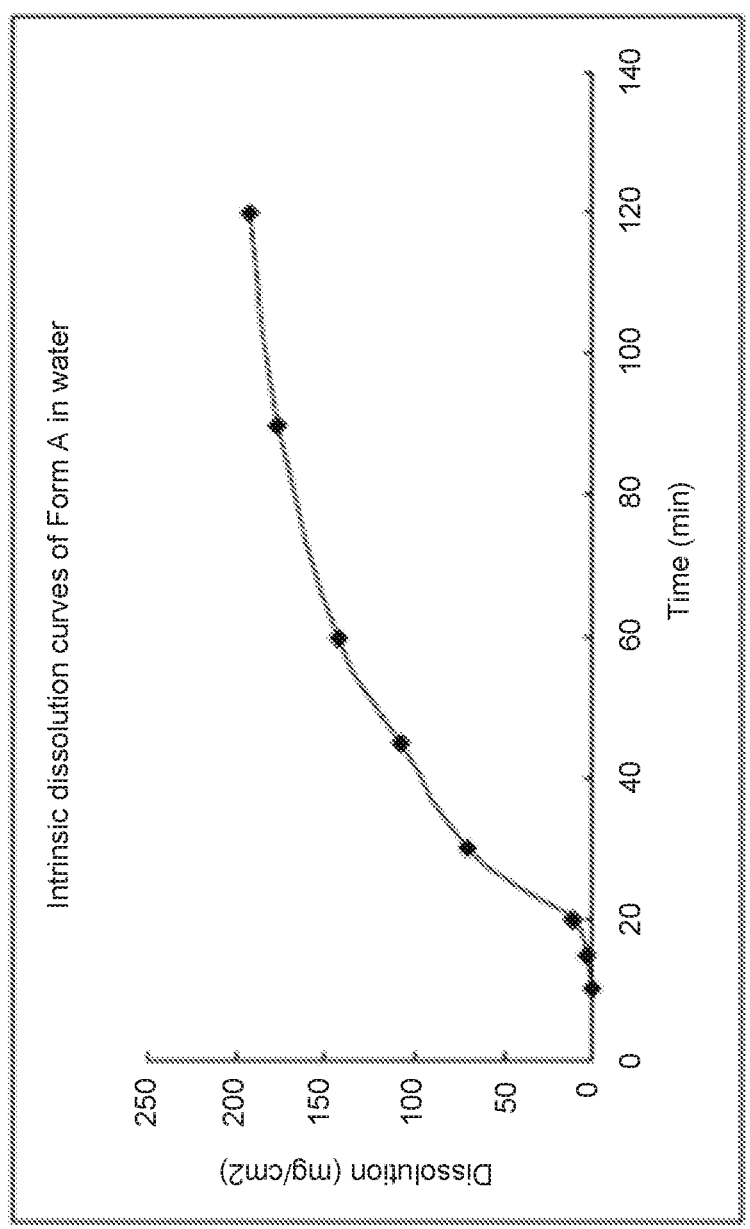
FIG. 11 shows intrinsic dissolution curves of Polymorph Form A in water.
Figure 12:
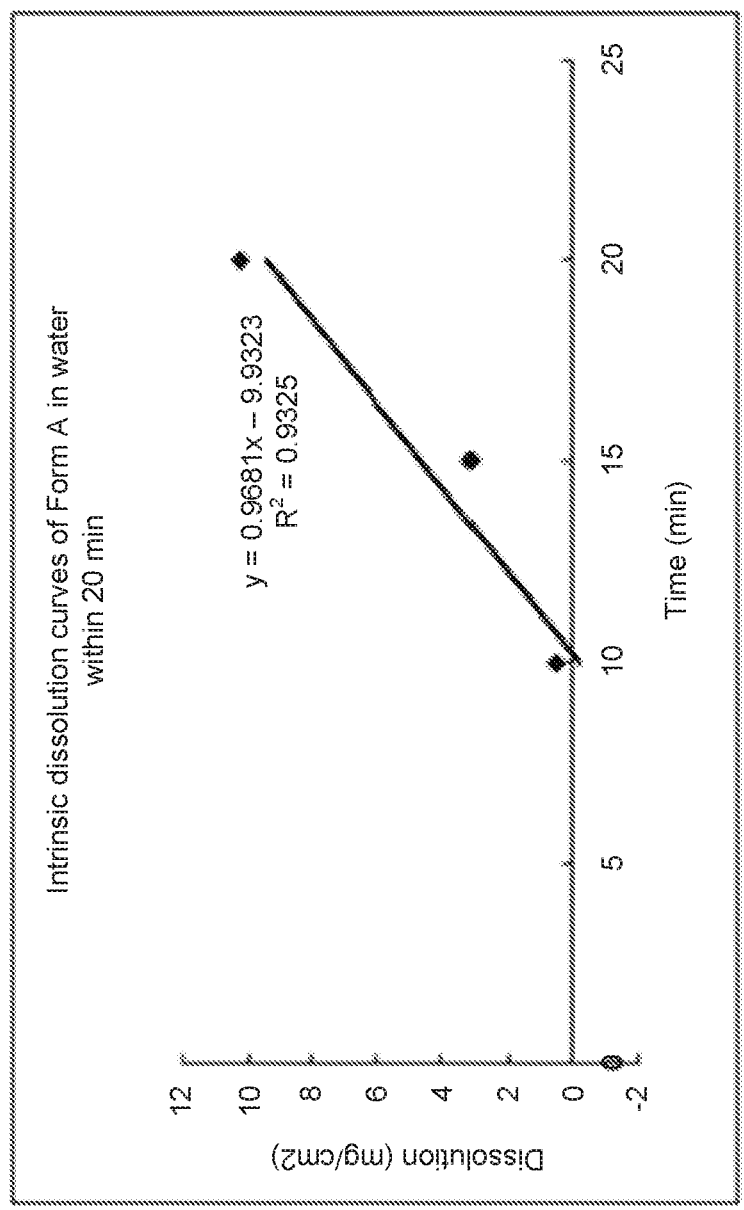
FIG. 12 shows intrinsic dissolution curves of Polymorph Form A in water within 20 mins.

The results are shown in Table 16 and FIG. 11 to FIG. 12. Polymorph Form A quickly swelled in testing media within 2 min and dropped to the bottom of the cup within 45 min. Polymorph Form A was not detected in water within 5 min (<LOQ, LOQ=305.1 ng/mL), and total 120 min in 0.1N HCl and pH 6.8 buffer because of the low solubility. The data of 10 min, 15 min, and 20 min in water were selected to calculate intrinsic dissolution rate.

4.6 Hygroscopicity 4.6.1. Experiment

About 10 mg Polymorph Form A was weighed and the sorption/desorption profiles were set at 25° C. under 0-90% relative humidity. The compound after testing was also subjected to an XRPD test to determine if any polymorph changes exist after exposure to a cycle of humidity change.

4.6.2. Result

Figures 13A, 13B:
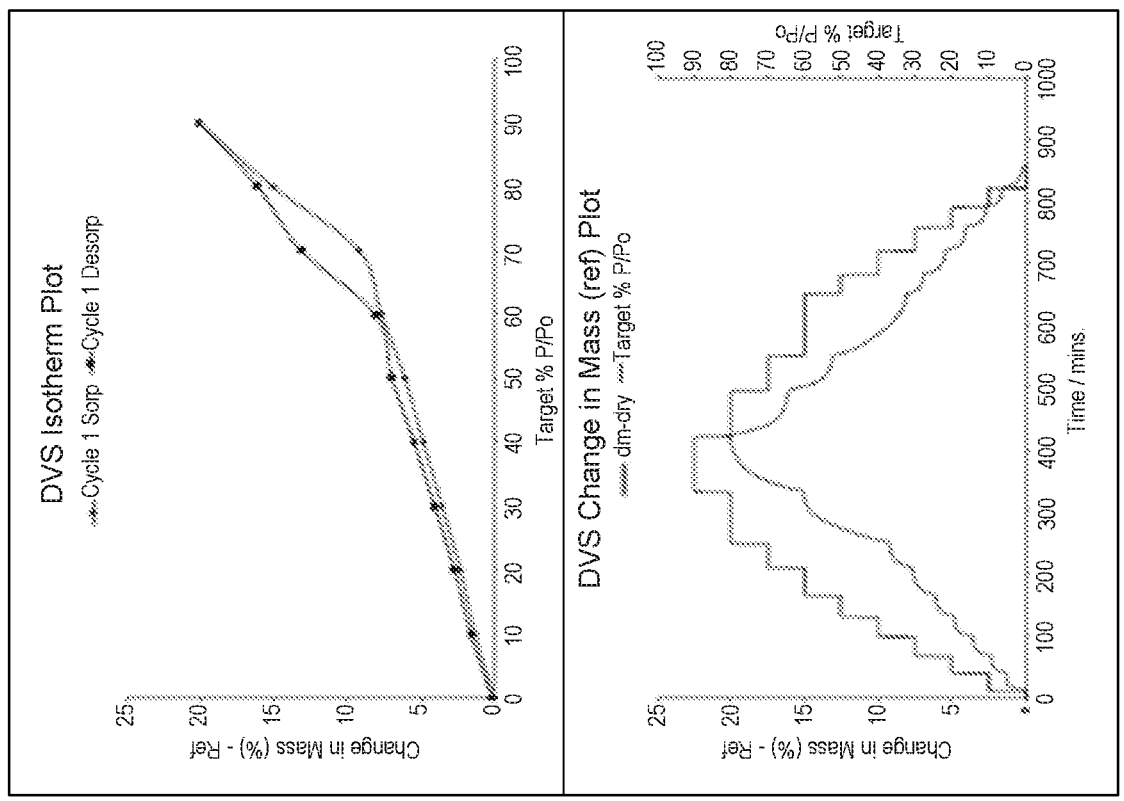
FIG. 13A shows a Dynamic Vapor Sorption ("DVS") isotherm graph for Polymorph Form A.
FIG. 13B shows changes in mass and humidity as a function of time for Polymorph Form A.
Figure 14:
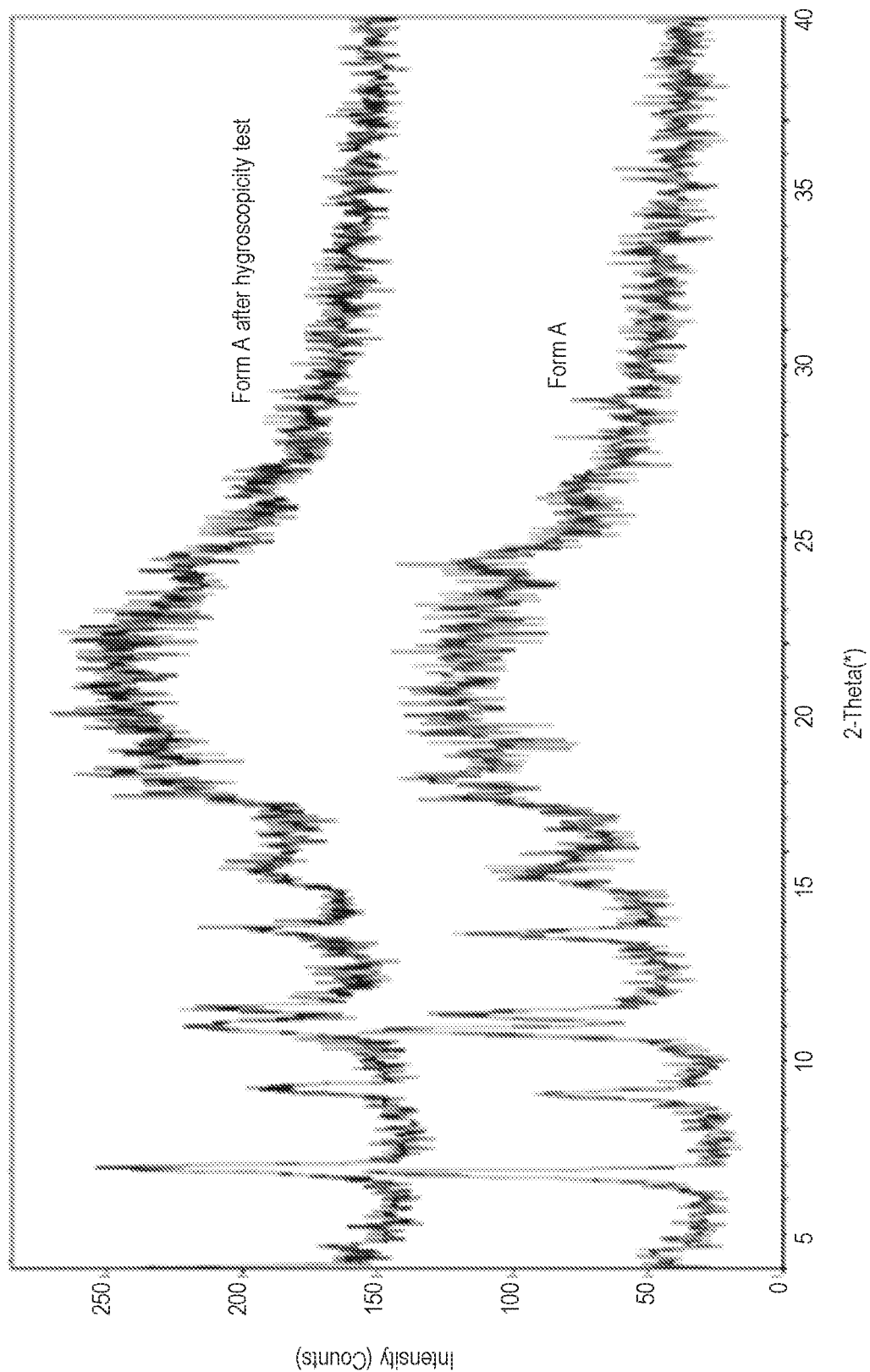
FIG. 14 is an XRPD overlay of Polymorph Form A before/after hygroscopicity test.

The results are shown in FIG. 13A, 13B, FIG. 14, and Table 11. The XRPD result showed no change of Polymorph Form A after hygroscopicity test. Table 11 is a DVS isotherm analysis report.

TABLE 11

DVS Isotherm Analysis Report

| | | Change in Mass (%)-ref | | |
|---|---|---|---|---|
| | Target % P/P₀ | Sorption | Desorption | Hysteresis |
| Cycle 1 | 0.0 | 0.00 | 0.20 | |
| | 10.0 | 1.35 | 1.64 | 0.29 |
| | 20.0 | 2.34 | 2.73 | 0.39 |

TABLE 11-continued

DVS Isotherm Analysis Report

| Target % P/P$_o$ | Change in Mass (%)-ref | | |
|---|---|---|---|
| | Sorption | Desorption | Hysteresis |
| 30.0 | 3.58 | 4.08 | 0.50 |
| 40.0 | 4.85 | 5.48 | 0.63 |
| 50.0 | 6.11 | 6.98 | 0.87 |
| 60.0 | 7.69 | 8.08 | 0.39 |
| 70.0 | 9.21 | 13.12 | 3.90 |
| 80.0 | 15.09 | 16.12 | 1.04 |
| 90.0 | 20.08 | 20.08 | |

According to the hygroscopicity result, Polymorph Form A could be classified as very hygroscopic (20.08% weight gain from 0 to 90% RH) according to the following definitions:

Deliquescent: sufficient water is absorbed to form a liquid.
Very hygroscopic: increase in mass is equal to or greater than 15 percent.
Hygroscopic: increase in mass is less than 15 percent and equal to or greater than 2 percent.
Slightly hygroscopic: increase in mass is less than 2 percent and equal to or greater than 0.2 percent.
Non-hygroscopic: increase in mass is less than 0.2 percent 5. Conclusion Polymorph Form A shows poor solubility in aqueous media, the best solubility was 6.54 mg/mL found in FeSSIF. The XRPD patterns have no change after solubility test.

For the solid stability, Polymorph Form A was relatively stable under light condition (no significant increase in TRS % or decrease in recovery %).

The pKa could not be detected because of the low solubility of Polymorph Form A and noise interference at low pH, and it shows lipophilicity with Log D values more than 4.32 in pH range of 1.0 to 11.0.

In the IDR result, Polymorph Form A could not be detected in 0.1N HCl, pH 6.8 USP buffer for 120 min. The intrinsic dissolution rate was 0.9681 mg/cm$^2$/min in water, but only the data of 10 min, 15 min and 20 min could be used because of its swelling and dropping.

Polymorph Form A is very hygroscopic (20.08% weight gain from 0 to 90% RH) as indicated by DVS graphs.

TABLE 12

Summary of Polymorph Form A solubility in different aqueous media (n = 2)

| Aqueous | Initial pH | Final pH | Appearance | Solubility (mg/mL) | Form |
|---|---|---|---|---|---|
| water | 6.34 | 6.48 | Turbid + many particles | 0.21 ± 0.01 | Form A |
| pH 4.0 buffer | 4.05 | 4.13 | Turbid + many particles | 0.05 ± 0.01 | Form A |
| pH 6.8 buffer | 6.84 | 6.87 | Turbid + many particles | 0.05 ± 0.00 | Form A |
| pH 7.4 buffer | 7.43 | 7.46 | Turbid + many particles | 0.06 ± 0.01 | Form A |
| pH 10.0 buffer | 10.02 | 10.00 | Turbid + many particles | 0.04 ± 0.00 | Form A |
| 0.1N HCl | 1.02 | 1.08 | Turbid + many particles | 0.06 ± 0.00 | Form A |
| 0.01N HCl | 1.97 | 2.24 | Turbid + many particles | 0.07 ± 0.00 | Form A |
| SGF | 1.22 | 1.37 | Turbid + many particles | 0.04 ± 0.01 | Form A |
| FaSSIF | 6.48 | 6.48 | Turbid + many particles | 0.21 ± 0.00 | Form A |
| FeSSIF | 4.98 | 5.06 | Turbid + many particles | 6.54 ± 0.19 | Form A |

TABLE 13

Solid stability of Polymorph Form A in light for 1 week and 2 weeks

| Condition | Time | Appearance | TRS % | Recovery % | XRPD pattern |
|---|---|---|---|---|---|
| −20° C. light | 0 day | white powder | 0.25 | — | Form A |
| | 1 week | white powder | 0.25 | 99.23 | Form A |
| | 2 weeks | white powder | 0.25 | 99.16 | Form A |

TABLE 14 pKa result of Polymorph Form A

| | pH metric method | | | UV metric method | |
|---|---|---|---|---|---|
| Items | (with 80 v % MeOH as initial co-solvent) | (with 60 v % DMSO as initial co-solvent) | (with 60 v % Dioxane as initial co-solvent) | (with 60 v % DMSO as initial co-solvent) | Final pKa Result |
| pKa | — | — | — | — | — |

TABLE 15

| Log D/P determined by Shake-Flask method | | | |
|---|---|---|---|
| | Log D Result | | |
| pH | Rep.1 | Rep.2 | Average |
| 1.0 | >4.32 | >4.32 | >4.32 |
| 1.5 | >4.32 | >4.32 | >4.32 |
| 2.0 | >4.32 | >4.32 | >4.32 |
| 3.0 | >4.32 | >4.32 | >4.32 |
| 4.0 | >4.32 | >4.32 | >4.32 |
| 7.4 | >4.32 | >4.32 | >4.32 |
| 11.0 | >4.32 | >4.32 | >4.32 |

TABLE 16

| Results of intrinsic dissolution rate | |
|---|---|
| Testing media | Intrinsic dissolution rate (mg/cm$^2$/min) |
| Water | 0.9681 |
| 0.1N HCl | — |
| pH 6.8 buffer | — |

Example 7

Salt Screening Study of Compound 1

I. Project Scope of Work:

A salt selection protocol contains about twenty pharmaceutically acceptable acids for crystalline salt selection of acidic compounds.

1. Salt Selection

The acid free form of Compound 1 was dissolved in a suitable solvent such that a reasonable concentration was achieved (approximately 0.1 to 0.5 M). Solutions of counter ions were prepared in a solvent that is miscible with the solvent chosen for Compound 1. The acid free form of Compound 1 and counter ion solutions were mixed to achieve expected salt stoichiometry. These mixtures were then screened against a list of solvents sequentially and the results were recorded in table format.

2. Solvents

Common organic solvents were used either as in pure form or in combination during the crystallization screening process. Other solvents can be used.

3. Physical Characteristics of Drug Candidate Salt(s):

SEM images along with its detailed solid state chemistry analysis were provided. The hygroscopic tests were also carried out as needed. Detailed hydrates and solvents can also be carried out as needed.

4. Crystallization Procedure:

A detailed process description was provided for the selected salt.

5. Process Flowchart

A process flowchart was provided for each crystal formation process.

II. Results and Discussions

In this study, a salt screen of Compound 1 was conducted under routine salt selection protocol. The protocol contained pharmaceutically acceptable bases for crystalline salt selection of acidic and diacidic compounds. The term "pharmaceutically acceptable salt form" means that the counter ion of the salt has been approved as a pharmaceutical substance by the FDA.

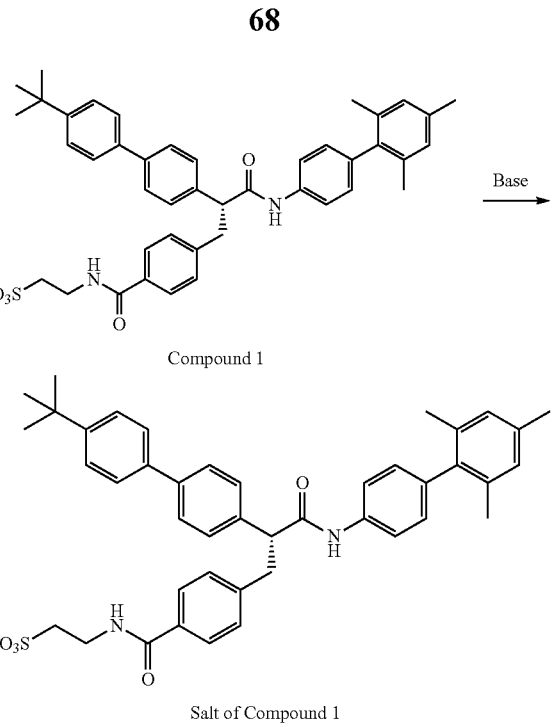

Figure 15:
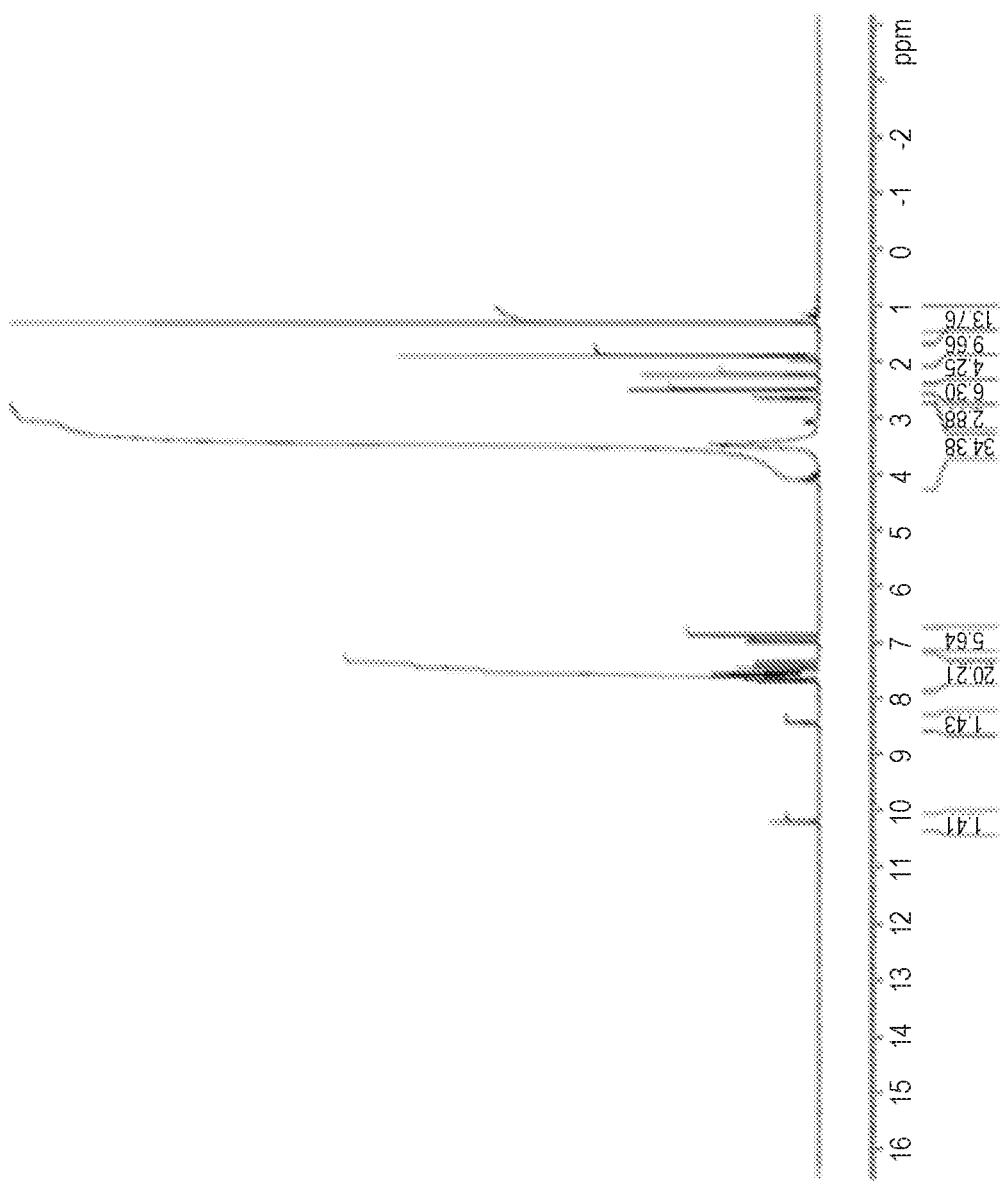
FIG. 15 is an $^1$H NMR Spectrum of Compound 1 in DMSO.

Compound 1 was synthesized by reaction of sodium salt of Compound 1 with hydrochloric acid in aqueous methanol, and the structure was characterized by $^1$H NMR (FIG. 15).

Compound 1 was amorphous based on the XRPD (FIG. 16). The salt screening results of Compound 1 are presented in Table 17. Among the pharmaceutically acceptable bases screened, sodium salt of Compound 1, potassium salt of Compound 1, and calcium salt of Compound 1 gave good solid forms and provide additional pharmaceutical candidates. The chemical purity of these compounds was analyzed by HPLC and the results were exhibited in Table 18.

TABLE 17

| The Results of Salt Screen of Compound 1 | | |
|---|---|---|
| Entry | Salt | Results |
| 1 | sodium salt of Compound 1 | Good Crystalline salt |
| 2 | calcium salt of Compound 1 | Good Crystalline salt |
| 3 | potassium salt of Compound 1 | Good Crystalline salt |

TABLE 18

| The Chemical Purity of Compound 1 and Salts of Compound 1 | |
|---|---|
| Compound Name | Purity |
| sodium salt of Compound 1 | 97.104 |
| Compound 1 | 98.335 |
| potassium salt of Compound 1 | 98.467 |
| calcium salt of Compound 1 | 99.611 |

A. Crystallization of Sodium Salt of Compound 1

Figure 18:
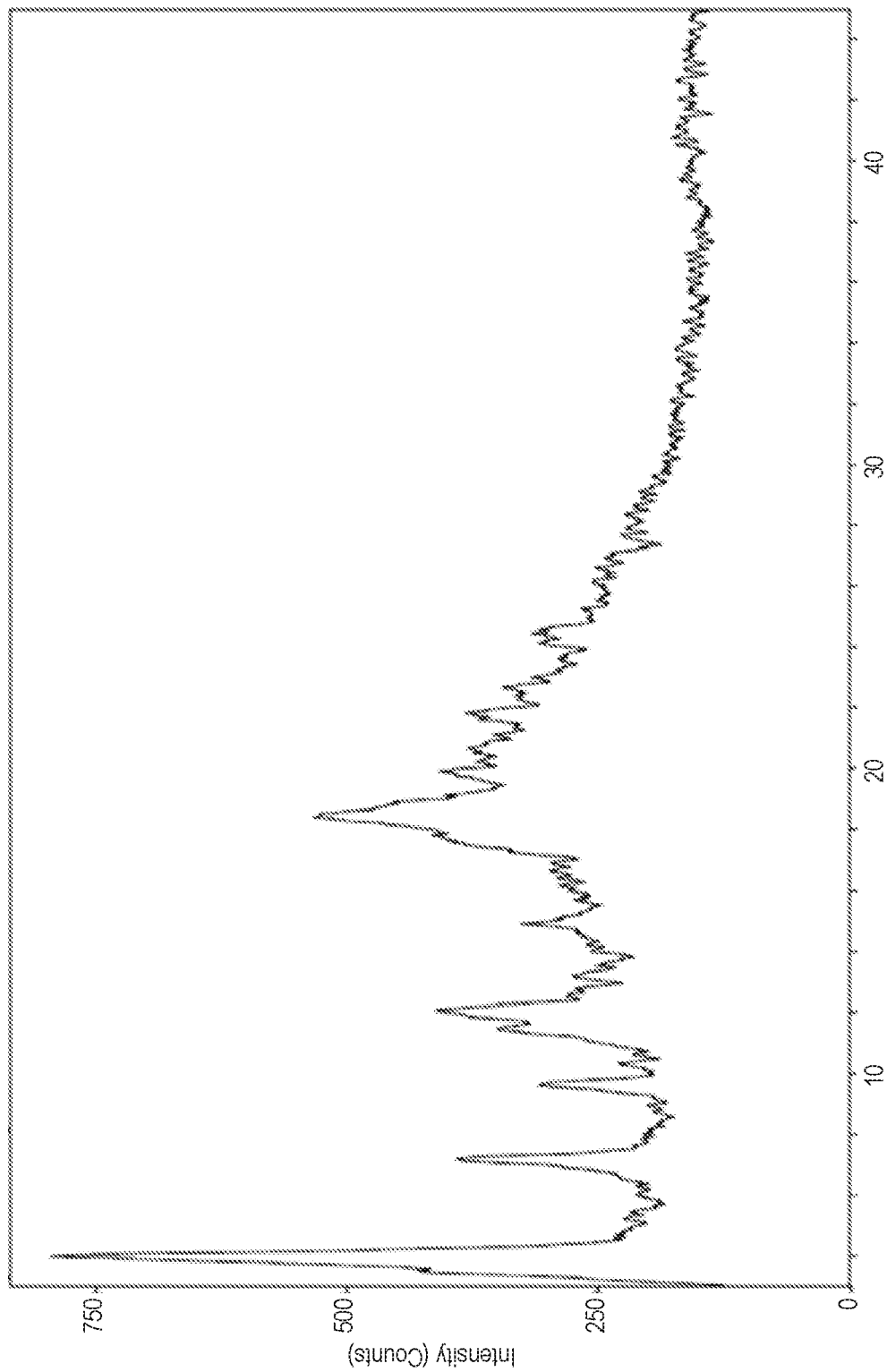
FIG. 18 is an XRPD pattern for a crystalline solid of sodium salt of Compound 1.

The Sodium salt of Compound 1 was amorphous based on the XRPD in FIG. 17. The amorphous sodium salt of Compound 1 was crystallized from methanol to give a crystalline solid. FIG. 18 depicts an XRPD pattern for this crystalline solid.

B. Crystallization of Calcium Salt of Compound 1

1. Solvent Selection

To find an optimal solvent system for the formation of Calcium salt of Compound 1, several solvents systems were screened (Table 19). Among them, methanol was identified as the best solvent for the crystallization process.

TABLE 19

Solvent Screening for Crystallization of Calcium Salt of Compound 1

| Reaction No. | Solvent | Results |
|---|---|---|
| 1 | Methanol | Good solid |
| 2 | 2-propanol | Precipitate |
| 3 | Ethanol | Precipitate |

2. Crystallization Procedures

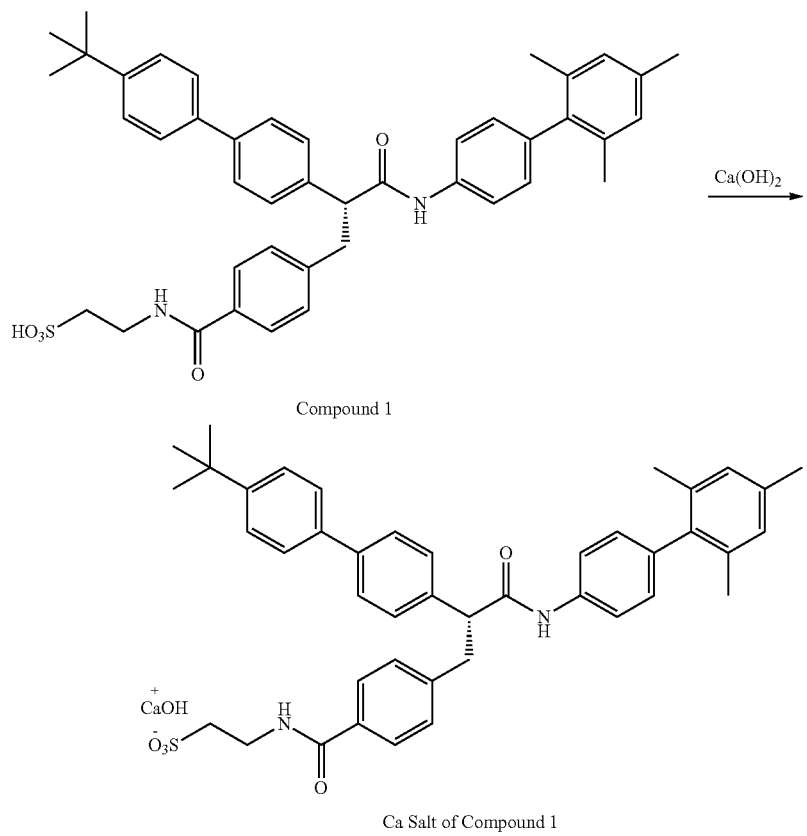

Compound 1

Ca Salt of Compound 1

Figure 35:
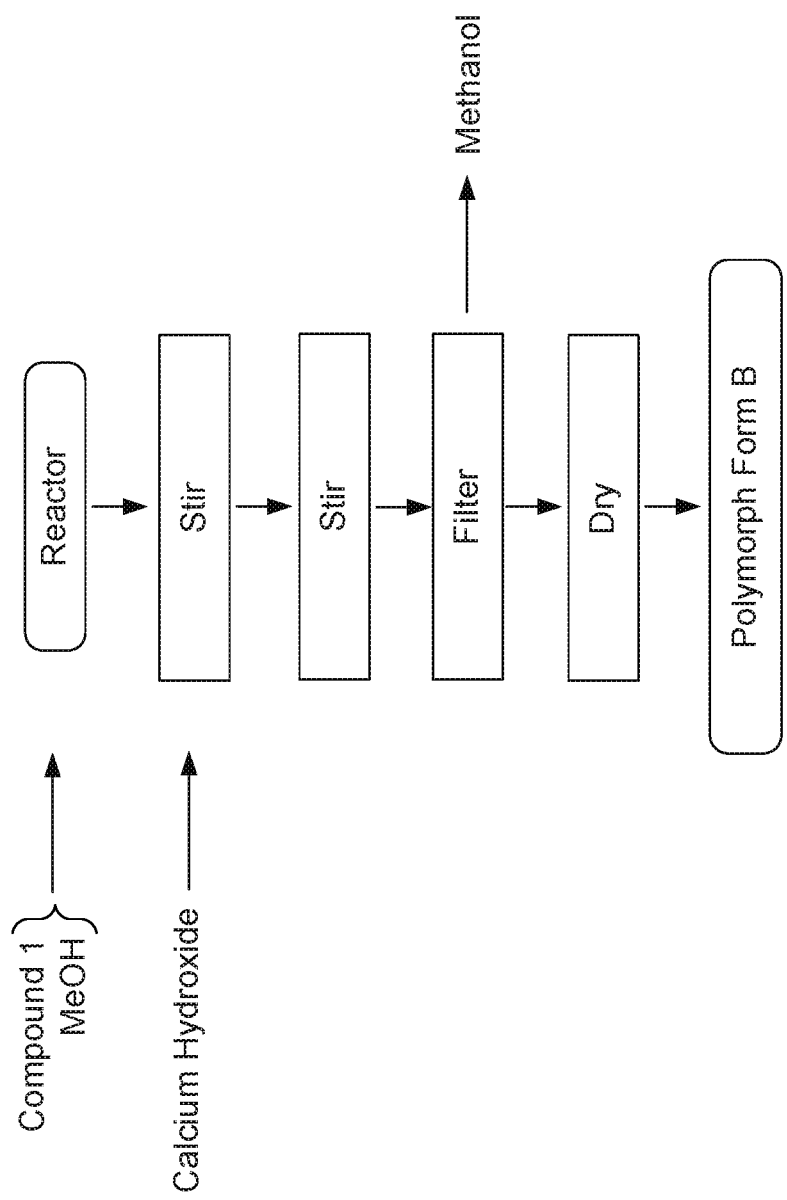
FIG. 35 shows a flowchart of the first procedure preparing Polymorph Form B.

Procedure 1:

To the solution of Compound 1 (15.5 mg, 0.022 mmol, 1 equiv) in methanol (0.3 mL) was added calcium hydroxide (2.41 mg, 0.032 mmol, 1.4 eq). The reaction mixture was stirred at 60° C. for 30 min and then at room temperature for 2 h. The slurry was filtered and dried under vacuum to constant weight to give Polymorph Form B. The procedure is illustrated in a flowchart shown in FIG. 35.

Figure 36:
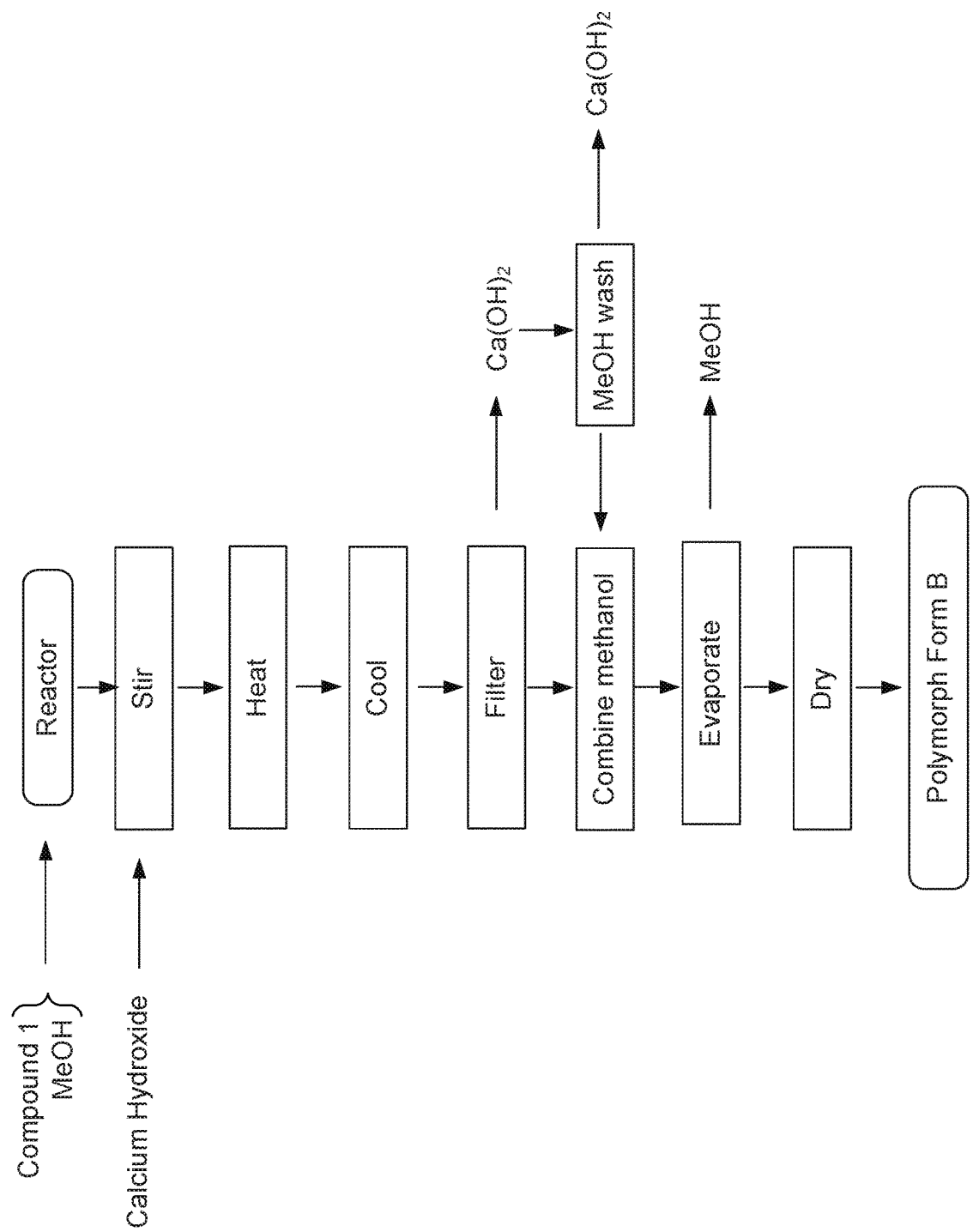
FIG. 36 shows a flowchart of the second procedure preparing Polymorph Form B.

Procedure 2:

To the solution of Compound 1 (50 mg, 0.071 mmol, 1 equiv) in methanol (2.4 mL) was added calcium hydroxide (21 mg, 0.28 mmol, 3.98 equiv). The reaction mixture was stirred at 60° C. for 30 min and then at room temperature for 2 h. The solid was filtered and washed with methanol (2*0.3 mL) twice. The combined methanol was evaporated to give a white solid, which was dried under vacuum to give 56 mg of Polymorph Form B. The procedure is illustrated in a flowchart shown in FIG. 36.

3. Physical Characterization of Polymorph Form B

Figure 22B:
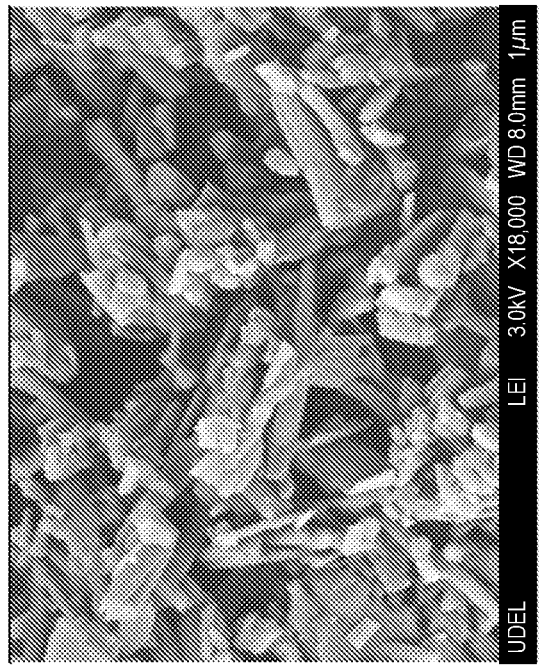
FIG. 22B shows an SEM image of Polymorph Form B with magnification of 18,000 times.
Figure 22A:
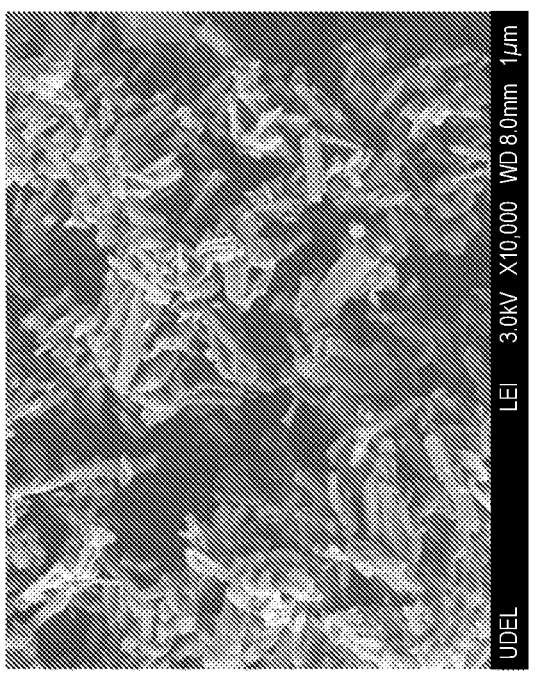
FIG. 22A shows a Scanning Electron Microscope ("SEM") image of Polymorph Form B with magnification of 10,000 times.

The stoichiometric ratio of Compound 1 to calcium was determined by elemental analysis as 1:1. Elemental Analysis: Calculated for $C_{43}H_{46}CaN_2O_6S$: Ca, 5.28. Found: Ca: 5.28. The crystallinity of the salt was confirmed by the XRPD (FIG. 19) and further supported by the DSC (FIG. 20) that indicated the Polymorph Form B with an onset temperature at 240.7° C. and a peak at 244.0° C. The TGA (FIG. 21) showed about 3.16% weight loss up to about 130° C. SEM in FIGS. 22A and 22B indicated the morphology of the salt.

4. Dynamic Vapor Sorption Study of Polymorph Form B

Figures 23A, 23B:
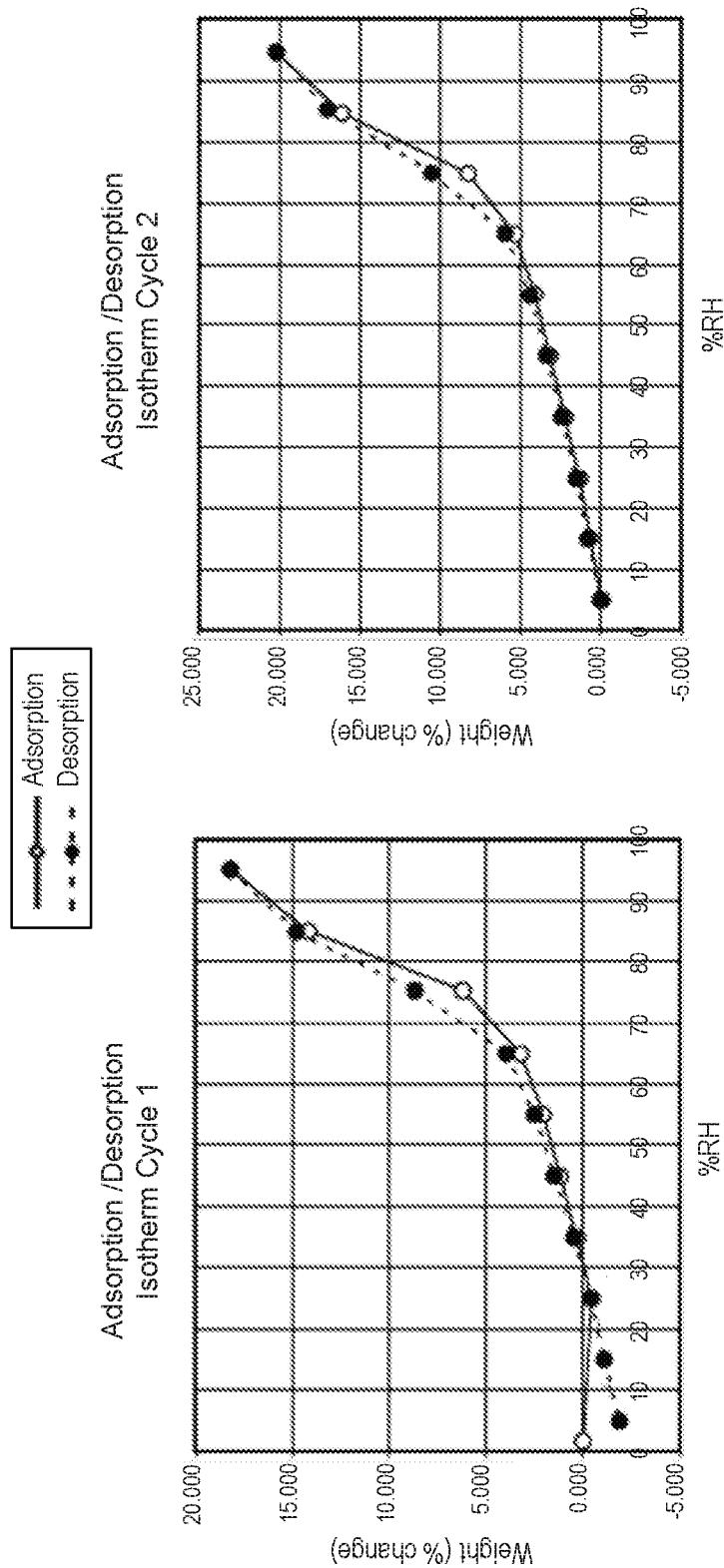
FIG. 23A shows cycle 1 of a DVS Isotherm experiment for Polymorph Form B.
FIG. 23B shows cycle 2 of a DVS Isotherm experiment for Polymorph Form B.

The moisture adsorption/desorption profiles of Polymorph Form B were studied by dynamic vapor sorption method. The results in FIGS. 23A and 23B showed that the salt could adsorb about 4% of the water at room temperature and normal humidity range, but it could adsorb water at room temperature continuously up to 20% at high humidity condition.

C. Crystallization of Potassium Salt of Compound 1

1. Solvent Selection

To find an optimal solvent system for the formation of potassium salt of Compound 1, several solvent systems were screened (Table 20). Among them, ethanol was identified as the best solvent for the crystallization process.

TABLE 20

Solvent Screening for Crystallization of Potassium Salt of Compound 1

| Reaction No. | Solvent | Results |
|---|---|---|
| 1 | Methanol/water (1:1) | Precipitate |
| 2 | 2-propanol | Precipitate |
| 3 | Ethanol | Good solid |

2. Typical Crystallization procedures

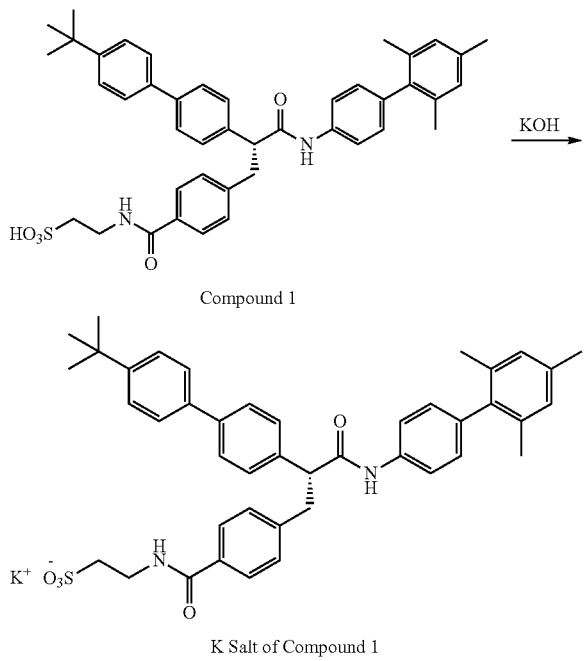

Compound 1

K Salt of Compound 1

Procedure 1

Figure 37:
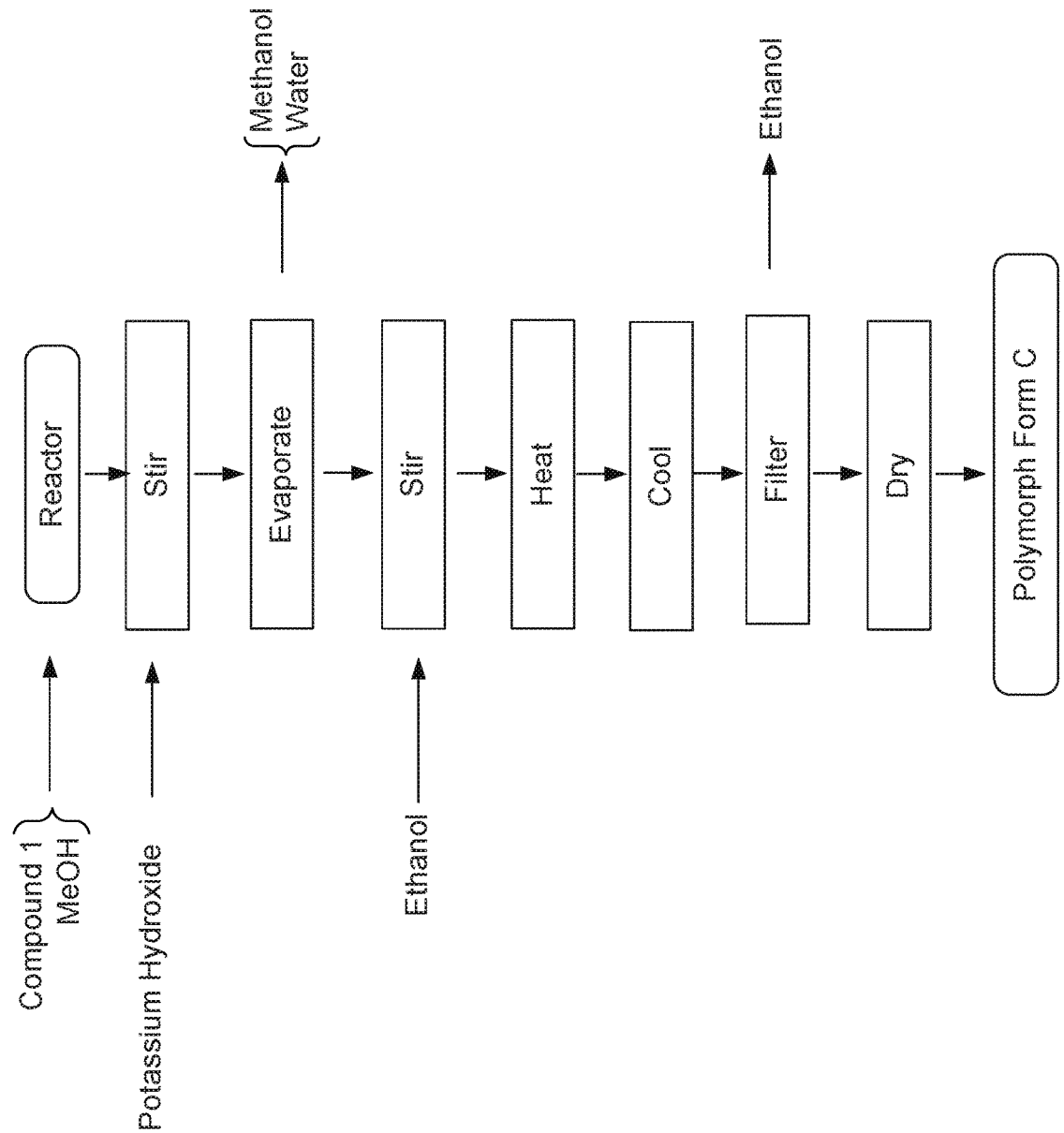
FIG. 37 shows a flowchart of the first procedure preparing Polymorph Form C.

A flask was charged Compound 1 (0.2 mL, 0.1 M, 0.020 mmol, 1 equiv) in methanol and potassium hydroxide aqueous solution (0.2 mL, 0.1 M, 0.02 mmol, 1 eq). After the slurry was stirred overnight and the solvents were evaporated, ethanol (0.4 mL) was added. The mixture was stirred at 70° C. for 40 min and then at room temperature for 2 h. The solid was collected by filtration and dried to provide Polymorph Form C as an off-white crystal. The procedure is illustrated in a flowchart shown in FIG. 37.

Procedure 2

Figure 38:
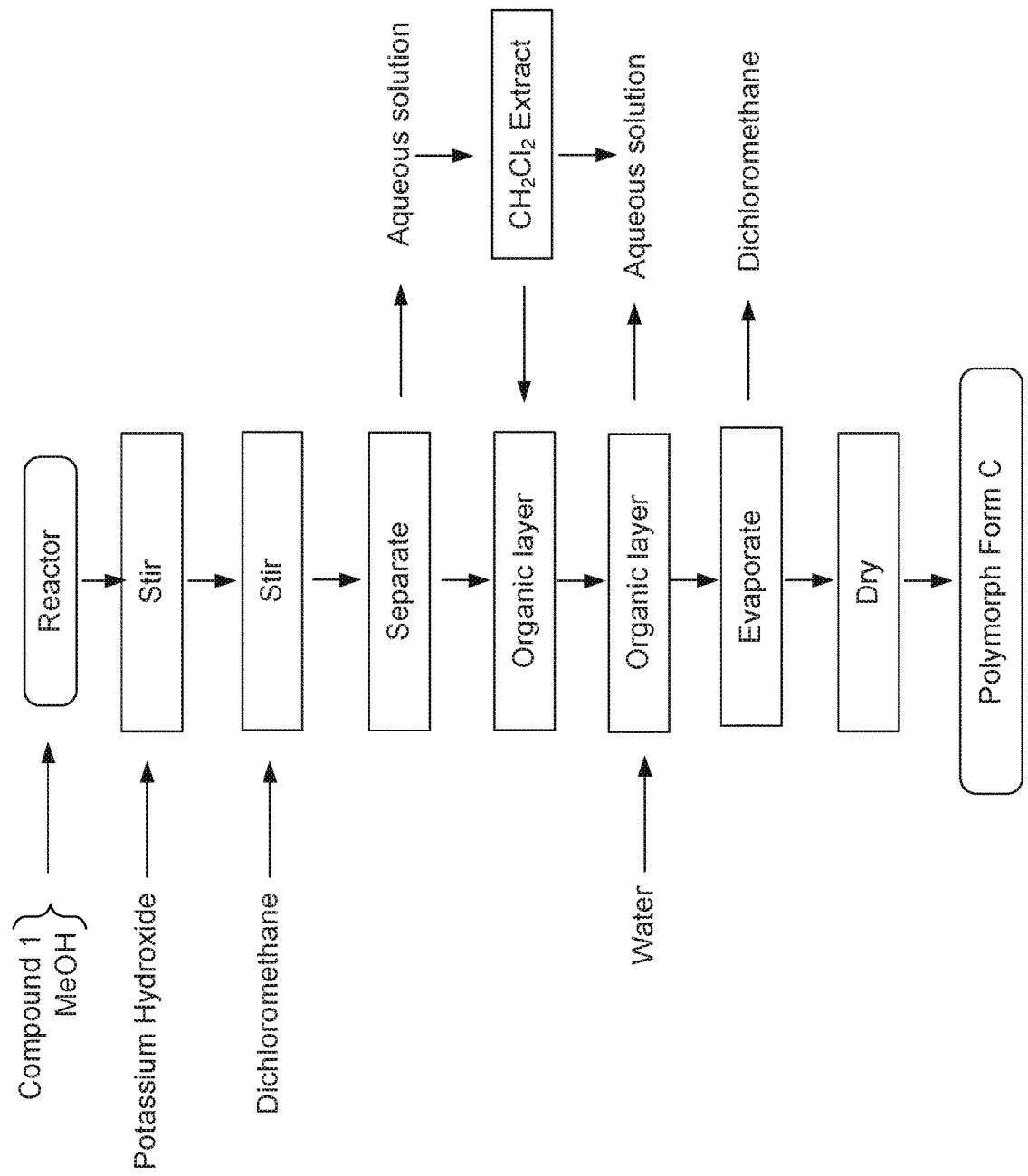
FIG. 38 shows a flowchart of the second procedure preparing Polymorph Form C.

A flask was charged with Compound 1 (75 mg, 0.107 mmol, 1 equiv) and methanol (2.5 mL) followed by an addition of potassium hydroxide aqueous solution (0.32 mL, 1 M, 0.32 mmol, 3 equiv) and water (1 mL). After the reaction mixture was stirred for 10 min, dichloromethane (1.5 mL) was added. The organic layer was separated from the aqueous layer, then, the water layer was extracted with dichloromethane twice (2*2.0 mL). The combined organic layer was washed with water (1 mL) and evaporated to give a solid. To the solid was added ethanol (2 mL). The slurry was stirred at 75° C. for 1 h and then at room temperature for 2 h. The solid was collected by filtration and dried to provide Polymorph Form C as an off-white crystal (49 mg, 62%). The procedure is illustrated in a flowchart shown in FIG. 38.

3. Physical Characterization of Polymorph Form C

Figure 27B:
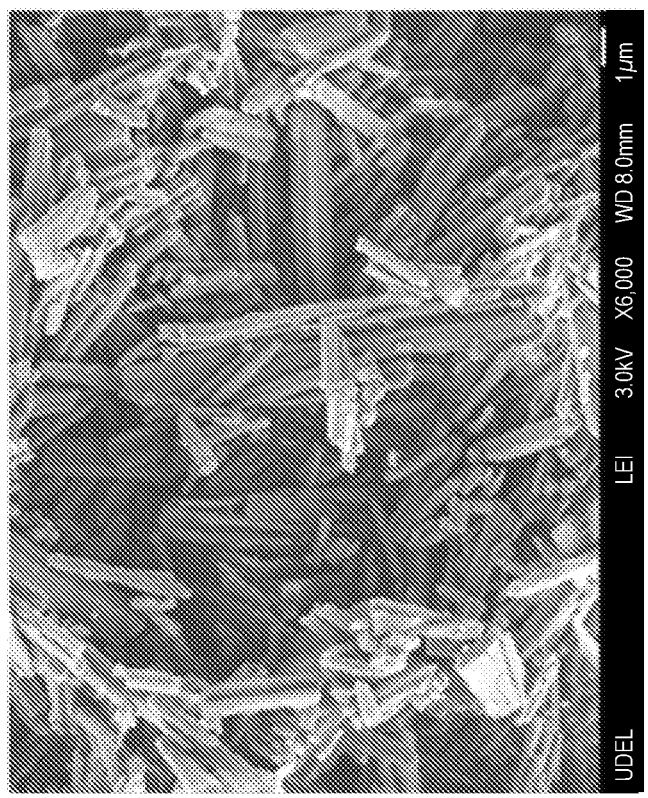
FIG. 27B shows an SEM Image of Polymorph Form C with magnification of 6,000 times.
Figure 27A:
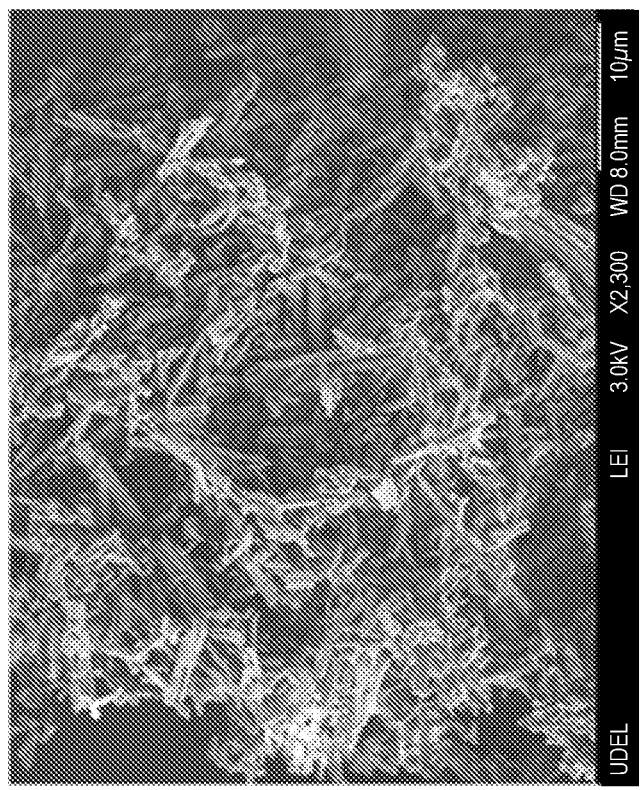
FIG. 27A shows an SEM Image of Polymorph Form C with magnification of 2,300 times.

The stoichiometric ratio of Compound 1 to Potassium was determined by elemental analysis as close to 1:1. Elemental Analysis: Calculated for $C_{43}H_{45}KN_2O_5S$: K, 5.28. Found: K, 4.70. The crystallinity of the salt was confirmed by the XRPD (FIG. 24) and further supported by the DSC (FIG. 25) that indicated the salt with an onset temperature at 194.41° C., and a peak at 202.48° C. The TGA (FIG. 26) showed about 2.23% weight loss up to about 100° C. The SEM images indicated that potassium salt of Compound 1 has a rod-like crystal shape (FIGS. 27A and 27B).

4. Dynamic Vapor Sorption Study of Polymorph Form C

Figures 28A, 28B:
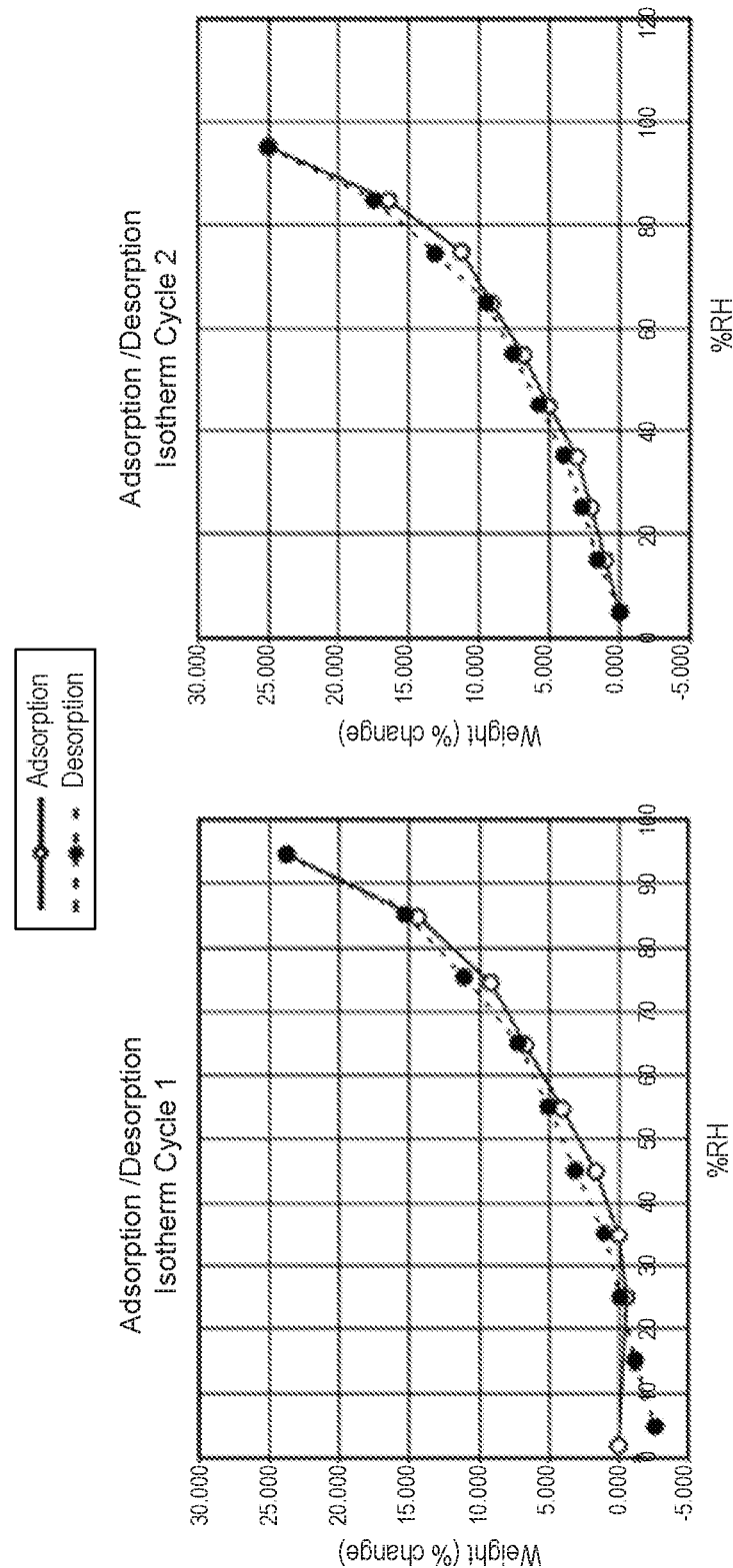
FIG. 28A shows cycle 1 of a DVS Isotherm experiment for Polymorph Form C.
FIG. 28B shows cycle 2 of a DVS Isotherm experiment for Polymorph Form C.

The moisture adsorption/desorption profiles of Polymorph Form C were studied by dynamic vapor sorption method. The results showed that the salt could adsorb about 6% of the water at room temperature and normal humidity range (FIGS. 28A and 28B), but it could adsorb water at room temperature continuously up to about 25% at high humidity condition.

The examples set forth above are provided to provide those of ordinary skill in the art with a complete disclosure and description of how to make and use the claimed embodiments, and are not intended to limit the scope of what is disclosed herein. Modifications that are obvious to persons of skill in the art are intended to be within the scope of the following claims.

All publications, patents, and patent applications cited in this specification are incorporated herein by reference in their entireties as if each such publication, patent or patent application were specifically and individually indicated to be incorporated herein by reference.

What is claimed is:

1. A crystalline form of sodium (R)-2-(4-(2-(4'-(tert-butyl)-[1,1'-biphenyl]-4-yl)-3-oxo-3-((2',4',6'-trimethyl-[1,1'-biphenyl]-4-yl)amino) propyl)benzamido) ethane-1-sulfonate characterized as Form A, wherein Form A is characterized by three or more peaks in an X-ray powder diffraction pattern, wherein the three or more peaks are selected from the group consisting of a peak at 4.7±0.2 degrees, a peak at 7.0±0.2 degrees, a peak at 9.3 degrees, a peak at 11.0±0.2 degrees, a peak at 11.4±0.2 degrees, a peak at ±0.2 11.9 degrees, a peak at 13.8±0.2 degrees, a peak at 21.4±0.2 degrees, and a peak at 23.8±0.2 degrees, when measured at room temperature with monochromatic Kα1 radiation.

2. The crystalline form of claim 1, wherein Form A is characterized by a peak at 4.7 degrees, a peak at 7.0±0.2 degrees, a peak at 9.3±0.2 degrees, a peak at 11.0±0.2 degrees, a peak at 11.4±0.2 degrees, a peak at 11.9±0.2 degrees, a peak at 13.8±0.2 degrees, a peak at 21.4±0.2 degrees, and a peak at 23.8±0.2 degrees in an X-ray powder diffraction pattern, when measured at room temperature with monochromatic Kα1 radiation.

3. The crystalline form of claim 1, wherein Form A is characterized by an X-ray powder diffraction pattern of FIG. 1.

4. The crystalline form of claim 1, wherein Form A is characterized by a DSC thermogram of FIG. 29.

5. The crystalline form of claim 1, wherein Form A is characterized by a purity of at least about 99.0%.

6. The crystalline form of claim 1, wherein Form A is characterized by the presence of no more than about 0.08% of impurity A, no more than about 0.12% of impurity B and no more than about 0.05% of impurity C.

7. The crystalline form of claim 1, wherein Form A is characterized by at least one of a $D_{10}$ of about 4.39 μm, a $D_{50}$ of about 16.10 μm, and a $D_{90}$ of about 43.18 μm.

8. The crystalline form of claim 1, comprising the following compound of Formula II:

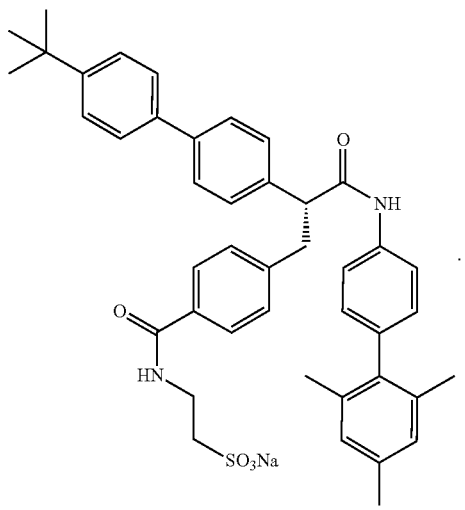

9. A pharmaceutical composition comprising the crystalline form of claim 1 in combination with one or more pharmaceutically acceptable diluents or carriers.

10. The pharmaceutical composition of claim 9, wherein the pharmaceutical composition further comprises a second therapeutic agent, wherein the second therapeutic agent is selected from the group consisting of insulin sensitizers, biguanides, metformin, PPAR agonists, triglitazone, pioglitazone, rosiglitazone, insulin and insulin mimetics, somatostatin, α-glucosidase inhibitors, voglibose, miglitol, acarbose, dipeptidyl peptidase-4 inhibitors, SGLT-2 inhibitors, liver X receptor modulators, insulin secretagogues, acetohexamide, carbutamide, chlorpropamide, glibornuride, gliclazide, glimerpiride, glipizide, gliquidine, glisoxepid, glyburide, glyhexamide, glypinamide, phenbutamide, sulfonylureas, tolazamide, tolbutamide, tolcyclamide, nateglinide, repaglinide, other glucagon receptor antagonists, GLP-1, GLP-1 mimetics, exenatide, liraglutide, DPPIV inhibitors, GLP-1 receptor agonists, GIP, GIP mimetics, GIP receptor agonists, PACAP, PACAP mimetics, PACAP receptor 3 agonists, cholesterol lowering agents, HMG-COA reductase inhibitors, statins, lovastatin, simvastatin, pravastatin, fluvastatin, atorvastatin, itavastatin, rivastatin, NK-104, itavastatin, nisvastatin, nisbastatin, ZD-4522 rosuvastatin, atavastatin, visastatin, a cholesterol absorption inhibitor ezetimibe, sequestrants, nicotinyl alcohol, nicotinic acid and salts thereof, PPAR α agonists, PPAR α/γ dual agonists, inhibitors of cholesterol absorption, acyl CoA:cholesterol acyltransferase inhibitors, anti-oxidants, PPAR δ agonists, antiobesity compounds, ileal bile acid transporter inhibitors, anti-inflammatory agents, and protein tyrosine phosphatase-1B (PTP-1B) inhibitors.

11. A method of treating, or ameliorating a condition, disorder, or disease responsive to the modulation of a glucagon receptor, or one or more symptoms thereof, comprising administering a therapeutically effective amount of the crystalline form of claim 1 to a subject in need thereof.

12. A method of treating, or ameliorating a condition, disorder, or disease responsive to the modulation of a glucagon receptor, or one or more symptoms thereof, comprising administering a therapeutically effective amount of the pharmaceutical composition of claim 9 to a subject in need thereof.

13. A method of treating, or ameliorating a condition, disorder, or disease responsive to a decrease in the hepatic glucose production or in the blood glucose level, or one or more symptoms thereof, comprising administering a therapeutically effective amount of the crystalline form of claim 1 to a subject in need thereof.

14. A method of treating, or ameliorating a condition, disorder, or disease responsive to a decrease in the hepatic glucose production or in the blood glucose level, or one or more symptoms thereof, comprising administering a therapeutically effective amount of the pharmaceutical composition of claim 9 to a subject in need thereof.

15. A method of treating, or ameliorating at least one condition, disorder, or disease, or one or more symptoms thereof, selected from the group consisting of type 1 diabetes, type 2 diabetes, gestational diabetes, ketoacidosis, ketosis, nonketotic hyperosmolar coma, nonketotic hyperglycemia, impaired glucose tolerance (IGT), insulin resistance syndromes, syndrome X, low HDL levels, high LDL levels, hyperglycemia, hyperinsulinemia, hyperlipidemia, hypertriglyceridemia, hyperlipoproteinemia, hypercholesterolemia, dyslipidemia, arteriosclerosis, atherosclerosis, glucagonomas, acute pancreatitis, cardiovascular diseases, hypertension, cardiac hypertrophy, gastrointestinal disorders, obesity, vascular restenosis, pancreatitis, neurodegenerative disease, retinopathy, nephropathy, neuropathy, accelerated gluconeogenesis, excessive or greater than normal levels of hepatic glucose output, and lipid disorders, comprising administering a therapeutically effective amount of the crystalline form of claim 1 to a subject in need thereof.

16. A method of treating, or ameliorating at least one condition, disorder, or disease, or one or more symptoms thereof, selected from the group consisting of type 1 diabetes, type 2 diabetes, gestational diabetes, ketoacidosis, ketosis, nonketotic hyperosmolar coma, nonketotic hyperglycemia, impaired glucose tolerance (IGT), insulin resistance syndromes, syndrome X, low HDL levels, high LDL levels, hyperglycemia, hyperinsulinemia, hyperlipidemia, hypertriglyceridemia, hyperlipoproteinemia, hypercholesterolemia, dyslipidemia, arteriosclerosis, atherosclerosis, glucagonomas, acute pancreatitis, cardiovascular diseases, hypertension, cardiac hypertrophy, gastrointestinal disorders, obesity, vascular restenosis, pancreatitis, neurodegenerative disease, retinopathy, nephropathy, neuropathy, accelerated gluconeogenesis, excessive or greater than normal levels of hepatic glucose output, and lipid disorders, comprising administering a therapeutically effective amount of the pharmaceutical composition of claim 9 to a subject in need thereof.

17. The method of claim 11, wherein the condition, disorder, or disease is diabetes.

18. The method of claim 11, wherein the condition, disorder, or disease is ketoacidosis.

19. The method of claim 11, wherein the subject is a mammal.

20. The method of claim 11, wherein the subject is human.

* * * * *

UNITED STATES PATENT AND TRADEMARK OFFICE
CERTIFICATE OF CORRECTION

PATENT NO. : 12,208,071 B2
APPLICATION NO. : 16/969521
DATED : January 28, 2025
INVENTOR(S) : Lin Zhi It is certified that error appears in the above-identified patent and that said Letters Patent is hereby corrected as shown below:

On the Title Page

Column 2, Page 2, item [56], Line 22-23, delete "Oxalyl Chloridel Dimethylformarnide," Synth." and insert -- Oxalyl Chloride Dimethylformamide," Synth. --.

Column 2, Page 2, item [56], Line 25, delete "using Iodotrimethylsilanc," J." and insert -- using Iodotrimethylsilane," J. --.

Column 2, Page 2, item [56], Line 35, delete "N-Dimethylformmids: eine" and insert -- N-Dimethylformamids: eine --.

Column 1, Page 3, item [56], Line 23, delete "of Alkenols and" and insert -- of Alkenes and --.

Column 1, Page 3, item [56], Line 26, delete ""Thermolysis ofbis[2-[(trimethylsilyl)oxy]prop-2-yl]" and insert -- "Thermolysis of bis[2-[(trimethylsilyl)oxy]prop-2-yl] --.

Column 1, Page 3, item [56], Line 36, delete "Derivatives of3′ -Acido-2′ 3′″" and insert -- Derivatives of 3′ -Acido-2′ 3′ --.

Column 1, Page 3, item [56], Line 58, delete "for Acyloxmethyl Esters" and insert -- for Acyloxymethyl Esters --.

Column 2, Page 3, item [56], Line 11, delete "Mixed Anydride and" and insert -- Mixed Anhydride and --.

Column 2, Page 3, item [56], Line 15, delete "Glucagon, Insulan, Dibutyrl Cyclic Adenosine" and insert -- Glucagon, Insulin, Dibutyryl Cyclic Adenosine --.

Signed and Sealed this
Fourth Day of November, 2025

John A. Squires
*Director of the United States Patent and Trademark Office*

CERTIFICATE OF CORRECTION (continued)
U.S. Pat. No. 12,208,071 B2

Column 2, Page 3, item [56], Line 21, delete "Non-Qqueous Solvent,"" and insert -- Non-Aqueous Solvent," --.

Column 2, Page 3, item [56], Line 36, delete "of 2-Hydroxymethy-1," and insert -- of 2-Hydroxymethyl-1, --.

Column 2, Page 3, item [56], Line 41, delete "et al., Transcstcrification ofDiphenyl Phosphonates" and insert -- et al., Transesterification of Diphenyl Phosphonates --.

Column 2, Page 3, item [56], Line 42, delete "O-Nonatlation and" and insert -- O- Notation and --.

Column 2, Page 3, item [56], Line 54, delete "by bromotrimethylsilanc," Tetrahedron" and insert -- by bromotrimethylsilane," Tetrahedron --.

Column 2, Page 3, item [56], Line 62, delete "and Phosphonacetate," J." and insert -- and Phosphonoacetate," J. --.

Column 1, Page 4, item [56], Line 19, delete "Dialkyl Mthylphosphnates and" and insert -- DialkylMethylPhosphonate and --.

Column 1, Page 4, item [56], Line 22, delete "pure allylarnines," Tetrahedron" and insert -- pure allylamines," Tetrahedron --.

Column 1, Page 4, item [56], Line 27, delete "delivery ofnucleoside monophosphates" and insert -- delivery of nucleoside monophosphates --.

Column 1, Page 4, item [56], Line 30, delete "von Methylphosphonsaure-dichlorid," Synthesis" and insert -- von MethylPhosphorus-dichloride," Synthesis --.

Column 1, Page 4, item [56], Line 33, delete "Mild Ilydrolytic Route,"" and insert -- Mild Hydrolytic Route," --.

Column 1, Page 4, item [56], Line 43, delete "Drug Deliver Technology," and insert -- Drug Delivery Technology, --.

Column 1, Page 4, item [56], Line 47, delete "Wilkins, Philadephia, PA," and insert -- Wilkins, Philadelphia, PA, --.

Column 1, Page 4, item [56], Line 57, delete "a-Carboxyl Delection, and" and insert -- a-Carboxyl Detection, and --.

Column 1, Page 4, item [56], Line 61, delete "the Merican Pharmaceutical" and insert -- the American Pharmaceutical --.

Column 1, Page 4, item [56], Line 66, delete "2 Diatests," Diabetes" and insert -- 2 Diabetes," Diabetes --.

Column 2, Page 4, item [56], Line 23, delete "of Epihatidine as" and insert -- of Epibatidine as --.

Column 2, Page 4, item [56], Line 25, delete "al., "Systhesis and" and insert -- al., "Synthesis and --.

Column 2, Page 4, item [56], Line 34, delete "the hormer-emmons" and insert -- the horner-emmons --.

Column 2, Page 4, item [56], Line 38, delete "Dichlorides: Applicationt to" and insert -- Dichlorides: Application to --.

Column 2, Page 4, item [56], Line 41, delete "Transesterification ofp-Nitrophenyl" and insert -- Transesterification of p-Nitrophenyl --.

Column 2, Page 4, item [56], Line 50, delete "Diabetes, Obestity and" and insert -- Diabetes, Obesity and --.

Column 2, Page 4, item [56], Line 55, delete ""An Enantioselective Synthesis" and insert -- "An Enantioselective Synthesis --.

Column 2, Page 4, item [56], Line 56, delete "Rationalization oflts Structure" and insert -- Rationalization of its Structure --.

Column 1, Page 5, item [56], Line 7, delete "Acid (Bio)|sosteres in" and insert -- Acid (Bio)Isosteres in --.

Column 1, Page 5, item [56], Line 12, delete "of bilogically relevant" and insert -- of biologically relevant --.

Column 1, Page 5, item [56], Line 17, delete "Molecular Modificaion and" and insert -- Molecular Modification and --.

Column 2, Page 5, item [56], Line 9, delete "al., "Chamical Society Reviews", Facts and fictgions about" and insert -- al., "Chemical Society Reviews", Facts and fictions about --.

In the Specification

Column 5, Line 18, delete "diastereomers thereof a" and insert -- diastereomers thereof; a --.

Column 5, Line 19, delete "prodrug thereof in" and insert -- prodrug thereof; in --.

CERTIFICATE OF CORRECTION (continued)
U.S. Pat. No. 12,208,071 B2

Column 5, Line 41, delete "prodrug thereof or" and insert -- prodrug thereof; or --.

Column 5, Line 51, delete "prodrug thereof or" and insert -- prodrug thereof; or --.

Column 5, Line 60, delete "prodrug thereof or" and insert -- prodrug thereof; or --.

Column 5, Line 66, delete "prodrug thereof or" and insert -- prodrug thereof; or --.

Column 7, Line 6, delete "Scanning calorimetry ("DSC")" and insert -- Scanning Calorimetry ("DSC") --.

Column 9, Line 50, delete "WO07015999A2, US20070203186A 1, US20080108620A1," and insert -- WO07015999A2, US20070203186A1, US20080108620A1 --.

Column 9, Line 54, delete "WO07047177A1, US20070088071A 1, WO07111864A2," and insert -- WO07047177A1, US20070088071A1, WO07111864A2, --.

Column 11, Line 61, delete "and (3-hydroxybutyrate. Three" and insert -- and β-hydroxybutyrate. Three --.

Column 11, Line 67, delete "substantially decreased" and insert -- substantially decreased. --.

Column 28, Line 7, delete "Drug Deliver Technology," and insert -- Drug Delivery Technology, --.

Column 29, Line 49, delete "and polymorphorism of" and insert -- and polymorphism of --.

Column 31, Line 51, delete "prodrug thereof or" and insert -- prodrug thereof; or --.

Column 31, Line 52, delete "composition thereof or" and insert -- composition thereof; or --.

Column 32, Line 25, delete "(e.g., triglitazone, pioglitazone," and insert -- (e.g., troglitazone, pioglitazone, --.

Column 32, Line 31, delete "gliclazide, glimerpiride, glipizide, gliquidine," and insert -- gliclazide, glimepiride, glipizide, gliquidone, --.

Column 32, Line 32, delete "glisoxepid, glyburide, glyhexamide, glypinamide, phenbutamide," and insert -- glisoxepide, glyburide, glyhexamide, glycinamide, phenbutamide, --.

Column 43, Line 65, delete "at <30° C." and insert -- at ≤30° C. --.

Column 44, Line 57, delete "at <30° C." and insert -- at ≤30° C. --.

CERTIFICATE OF CORRECTION (continued)
U.S. Pat. No. 12,208,071 B2

Column 44, Line 67, delete "at <30° C." and insert -- at ≤30° C. --.

Column 46, Line 53, delete "at <25° C." and insert -- at ≤25° C. --.

Column 46, Line 56, delete "at <25° C." and insert -- at ≤25° C. --.

Column 47, Line 49, delete "[1,1'-biphenyl]-4-O-3-oxo" and insert -- [1,1'-biphenyl]-4-yl)-3-oxo --.

Column 58, Line 58, delete "No. IH11F61419; Tetrahydrofuran" and insert -- No. IH1IF61419; Tetrahydrofuran --.

Column 58, Line 60, delete "No. SBOS600084; Methanol" and insert -- No. SB0S600084; Methanol --.

Column 60, Line 65, delete "at 20 angles" and insert -- at 2θ angles --.

Column 61, Line 25, delete "any ionicable compound" and insert -- any ionizable compound --.

Column 63, Line 24, TABLE 10, delete "Chi Squred" and insert -- Chi Squared --.

In the Claims

Column 71, Line 39, Claim 1, delete "at 9.3 degrees," and insert -- at 9.3±0.2 degrees, --.

Column 72, Line 39, Claim 1, delete "at ±0.2 11.9 degrees," and insert -- at 11.9±0.2 degrees, --.

Column 73, Line 29, Claim 10, delete "agonists, triglitazone, pioglitazone," and insert -- agonists, troglitazone, pioglitazone, --.

Column 73, Line 35, Claim 10, delete "gliclazide, glimerpiride, glipizide, gliquidine, glisoxepid, glyburide," and insert -- gliclazide, glimepiride, glipizide, gliquidone, glisoxepide, glyburide, --.

Column 73, Line 35, Claim 10, delete "glyhexamide, glypinamide, phenbutamide," and insert -- glyhexamide, glycinamide, phenbutamide, --.

Column 73, Line 42, Claim 42, delete "agents, HMG-COA reductase" and insert -- agents, HMG-CoA reductase --.